United States Patent
Goodnow, Jr. et al.

(10) Patent No.: US 7,371,869 B2
(45) Date of Patent: *May 13, 2008

(54) SUBSTITUTED HYDANTOINS

(75) Inventors: Robert Alan Goodnow, Jr., Gillette, NJ (US); Nicholas J. S. Huby, Scotch Plains, NJ (US); Norman Kong, West Caldwell, NJ (US); Lee Apostle McDermott, Parlin, NJ (US); John Anthony Moliterni, Bloomfield, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/225,950

(22) Filed: Sep. 14, 2005

(65) Prior Publication Data
US 2006/0063814 A1    Mar. 23, 2006

Related U.S. Application Data

(60) Provisional application No. 60/610,655, filed on Sep. 17, 2004.

(51) Int. Cl.
*A61K 31/427* (2006.01)
*C07D 409/12* (2006.01)

(52) U.S. Cl. .................... 548/195; 514/371

(58) Field of Classification Search ............ 548/195
See application file for complete search history.

(56) References Cited

FOREIGN PATENT DOCUMENTS

| WO | WO 99/01426 | 1/1999 |
| WO | WO 99/05117 A1 | 2/1999 |
| WO | WO 01/83478 | 11/2001 |

OTHER PUBLICATIONS

Golub et al., Science, vol. 286, Oct. 15, 1999, pp. 531-537.*
J. M. English et al., *Trends in Pharm. Sci.* 2002, 23(1), 40.
J. L. Bos, *Cancer Res.* 1989, 49, 4682.
A. Bonni et al., *Science* 1999, 286, 1358.
H. Davies et al., *Nature* 2002, 417, 949.
R. Herrera et al., *Trends Mol. Med.* 2002, 8(4, Suppl.), S27.
C. F. Zheng et al., *J. Biol. Chem.* 1993, 268, 11435.
S. Cowley et al., *Cell* 1994, 77, 841.
R. Seger et al., *J. Biol. Chem.* 1992, 267, 14373.

* cited by examiner

*Primary Examiner*—Laura L. Stockton
(74) *Attorney, Agent, or Firm*—George W. Johnston; Patricia S. Rocha-Tramaloni

(57) ABSTRACT

The present invention relates to compounds of the formula

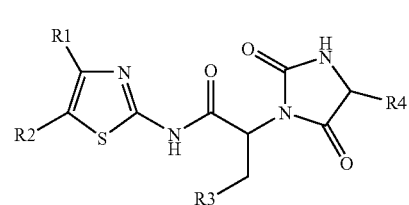

which are useful in treating diseases characterized by the hyperactivity of MEK. Accordingly the compounds are useful in the treatment of diseases, such as, cancer, cognative and CNS disorders and inflammatory/autoimmune diseases.

5 Claims, No Drawings

SUBSTITUTED HYDANTOINS

PRIORITY TO RELATED APPLICATIONS

This application claims the benefit of U.S. Provisional Application No. 60/610,655, filed Sep. 17, 2004, which is hereby incorporated by reference in its entirety.

FIELD OF THE INVENTION

The present invention relates to hydantoin derivatives of the formula

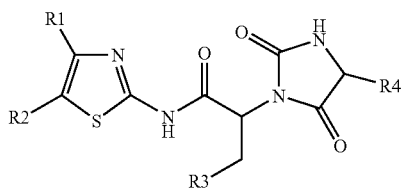

wherein $R^1$, $R^2$, $R^3$ and $R^4$ are defined hereafter.

The compounds have activity as inhibitors of the two protein kinases commonly known as MEK1 and MEK2 for the treatment of human diseases such as cancer. MEK is a commonly used abbreviation for MAP kinase/ERK kinase which is in turn an abbreviation for mitogen activated protein/extracellular signal regulated kinase kinase. MEK is also sometimes referred to as MAPK kinase or MAP kinase kinase.

BACKGROUND OF THE INVENTION

Cancer is a disease characterized by the proliferation of malignant cells and tumors which have the potential for unlimited growth, local expansion and systemic metastasis. This uncontrolled growth is derived from abnormalities in the signal transduction pathways and the response to various growth factors, which differ from those found in normal cells. The abnormalities include changes in the intrinsic activity or in the cellular concentration of one or more signaling proteins in the signaling cascade. These changes are frequently caused by genetic mutations or over expression of intracellular signaling proteins which can lead to spurious mitogenic signals within the cells.

The mitogen activated protein (MAP) kinase pathway represents one of the best characterized signaling pathways involved in the development and progression of human cancers (J. M. English et al., *Trends in Pharm. Sci.* 2002, 23(1), 40). This pathway, via the Ras/Raf/MEK/ERK signal cascade, is responsible for transmitting and amplifying mitogenic signals from the cell surface to the nucleus where activated transcription factors regulate gene expression and determine cell fate. The constitutive activation of this pathway is sufficient to induce cellular transformation. Dysregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers (J. L. Bos, *Cancer Res.* 1989, 49, 4682). The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2) which in turn phosphorylate ERK1 and ERK2 (extracellular signal-regulated kinases 1 and 2) on both tyrosine-185 and threonine-183. Activated ERK1 and ERK2 translocate and accumulate in the nucleus, where they can phosphorylate a variety of substrates, including transcription factors that control cellular growth and survival (A. Bonni et al., *Science* 1999, 286, 1358). Recently, B-Raf somatic mutations in the kinase domain were also found in 66% of malignant melanomas, and at a lower frequency in a wider range of human cancers (H. Davies et al., *Nature* 2002, 417, 949). Like mutated Ras, constitutively active mutated Raf can transform cells in vitro and induce malignancies in a variety of animal models (H. Davies et al., *Nature* 2002, 417, 949). Given the importance of the Ras/Raf/MEK/ERK pathway in the development of human cancers, the kinase components of this signaling cascade are emerging as potentially important targets for the modulation of disease progression in cancer and other proliferative diseases (R. Herrera et al., *Trends Mol. Med.* 2002, 8(4, Suppl.), S27).

MEK1 and MEK2 are members of a larger family of dual-specificity kinase (MEK1-7) that phosphorylate threonine and tyrosine residues of various MAP kinases. MEK1 and MEK2 are encoded by distinct genes, but they share high homology (80%) both within the C-terminal catalytic kinase domains and most of the N-terminal regulatory region (C. F. Zheng et al., *J. Biol. Chem.* 1993, 268, 11435). Oncogenic forms of MEK1 and 2 have not been found in human cancers. However, constitutive activation of MEK has been shown to result in cellular transformation (S. Cowley et al., *Cell* 1994, 77, 841). In addition to Raf, MEK can also be activated by other oncogenes as well. So far, the only known substrates of MEK1 and 2 are ERK1 and 2 (R. Seger et al., *J. Biol. Chem.* 1992, 267, 14373). This unusual substrate specificity in addition to the unique ability to phosphorylate both tyrosine and threonine residues places MEK1 and 2 at a critical point in the signal transduction cascade which allows it to integrate many extracellular signals into the MAPK pathway.

Previously reported studies with the MEK inhibitor 2-(2-chloro-4-iodo-phenylamino)-N-cyclopropylmethoxy-3,4-difluoro-benzamide, also known as CI-1040 (Pfizer Inc., described in PCT publication No. WO 99/01426) provides further evidence that MEK1 and 2 represent an attractive target for pharmacological intervention in cancer or other human diseases characterized by the hyperactivity of MEK and diseases regulated by the MAPK pathway.

Compounds related to the compounds of the present invention have previously been reported as glucokinase activators (F. Hoffmann-La Roche A G, PCT publication No. WO 01/83478). The compounds which have been previously reported were defined as containing a methylene spacer ($CH_2$ group) between the hydantoin ring and additional substituents which included an unsubstituted or a substituted aryl ring amongst other defined substituents. The compounds claimed in the present invention are defined to include compounds where there is no methylene spacer between the hydantoin ring and substituted or unsubstituted aryl or substituted or unsubstituted heteroaryl group rings.

SUMMARY OF THE INVENTION

There are provided compounds of the formula

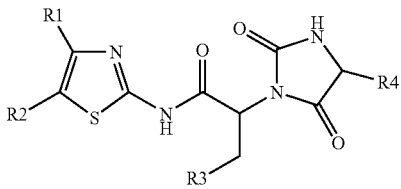

I wherein
$R^1$ is $COR^5$;
$R^2$ is hydrogen;
$R^3$ is selected from the group consisting of substituted or unsubstituted alkyl, alkenyl or alkynyl, cycloalkyl and substituted or unsubstituted heterocycle, aryl or heteroaryl;
$R^4$ is selected from the group consisting of substituted or unsubstituted aryl or heteroaryl;
$R^5$ is selected the group consisting of lower alkyl, lower alkoxy or amine substituted by hydrogen, lower alkyl or lower alkoxy;

and the pharmaceutically acceptable salts, esters or prodrugs thereof.

"Alkyl" denotes a straight-chained, branched or cyclic saturated aliphatic hydrocarbon. Preferably, alkyl denotes a lower alkyl group i.e., a C1-C6 alkyl group and includes methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl. Examples of cycloalkyl groups are moieties having 3 to 10, preferably 3 to 7 carbon atoms including cyclopropyl, cyclopentyl and cyclohexyl groups. As mono-, di- or tri-substituents on the $R^3$ alkyl, alkenyl or alkynyl one can include thioalkyl groups, alkyl sulfones,e.g.,methylsulfonyl, halo, alkoxy, hydroxyl, aldehyde groups, carboxylic amides, nitrile, ketones and carboxylic acids and esters.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrollidin-3-yl; imidazol4-yl; pyrazol-3-yl; morpholin4-yl and the like.

As mono-, di- or tri- substituents on the aryl or heteroaryl rings one can include hydroxyl, alkoxy, hydroxyl alkoxy, halogen, alkylamines, alkoxyamines, sulfonamides, acetamides and methanesulfonyl. Other substituents include alkyl or substituted alkyl having substituents as noted above. In the case of multiple substituents they can also form a second ring fused to the original aryl or heteroaryl ring.

"Alkoxy or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable ester" refers to a conventionally esterified compound of formula I having a carboxyl group, esters of which retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard, Hans ed. (Elsevier, 1985). See also, Ansel et al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp.152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount" means an amount of at least one designated compound, which significantly inhibits proliferation and/or prevents differentiation of a human tumor cell, including human tumor cell lines.

The compounds of the present invention are useful in the treatment or control of cell proliferative disorders such as inflammatory/autoimmune disorders, e.g., restenosis, cognative disorders, e.g., dementia and Alzeheimer's disease, CNS disorders, e.g., neuropathic pain and, in particular, oncological disorders. These compounds and formulations containing said compounds may be useful in the treatment or control of solid tumors, such as, for example, breast, colon, lung and prostate tumors.

The compounds of formula I as well as their salts have at least one asymmetric carbon atom and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or by parenteral administration; it may be given as continuous infusion.

DETAILED DESCRIPTION OF THE INVENTION

The present invention relates to compounds of the formula

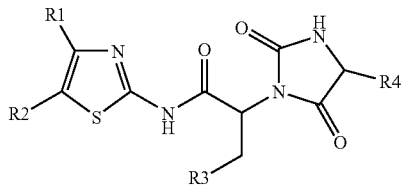

I wherein $R^1$ is $COR^5$;

$R^2$ is hydrogen;

$R^3$ is selected from the group consisting of substituted or unsubstituted alkyl, alkenyl or alkynyl, cycloalkyl and substituted or unsubstituted heterocycle, aryl or heteroaryl;

$R^4$ is selected from the group consisting of substituted or unsubstituted aryl or heteroaryl;

$R^5$ is selected the group consisting of lower alkyl, lower alkoxy or amine substituted by hydrogen, lower alkyl or lower alkoxy;

and the pharmaceutically acceptable salts, esters or prodrugs thereof.

Preferred among the compounds of formula I are those wherein $R^1$ is $COR^5$ where $R^5$ is lower alkoxy, especially, methoxy;

$R^2$ is hydrogen;

$R^3$ is substituted aryl or substituted heteroaryl;

$R^4$ is substituted aryl or substituted heteroaryl.

Especially preferred are compounds of the formula:

2-[(S)-2-((S)-2,5-dioxo-4-phenyl-imidazolidin-1-yl)-4-methyl-pentanoylamino]-thiazole-4-carboxylic acid methyl ester;

2-[(S)-3-cyclohexyl-2-((S)-2,5-dioxo-4-phenyl-imidazolidin-1-yl)-propionylamino]-thiazole-4-carboxylic acid methyl ester;

2-[(S)-2-((S)-2,5-dioxo-4-phenyl-imidazolidin-1-yl)-hexanoylamino]-thiazole-4-carboxylic acid methyl ester;

2-[(S)-2-((S)-2,5-dioxo-4-phenyl-imidazolidin-1-yl)-2-phenyl-acetylamino]-thiazole-4-carboxylic acid methyl ester;

2-[(R)-2-((S)-2,5-dioxo-4-phenyl-imidazolidin-1-yl)-3-(4-hydroxy-phenyl)-propionylamino]-thiazole-4-carboxylic acid methyl ester;

2-[(S)-2-((S)-2,5-dioxo-4-phenyl-imidazolidin-1-yl)-4-methylsulfanyl-butyrylamino]-thiazole-4-carboxylic acid methyl ester;

2-[(S)-2-((S)-2,5-dioxo-4-phenyl-imidazolidin-1-yl)-3-thiophen-2-yl-propionylamino]-thiazole-4-carboxylic acid methyl ester;

2-[(S)-2-((S)-2,5-dioxo-4-phenyl-imidazolidin-1-yl)-4-phenyl-butyrylamino]-thiazole-4-carboxylic acid methyl ester;

2-[(R)-2-((S)-2,5-dioxo-4-phenyl-imidazolidin-1-yl)-pentanoylamino]-thiazole-4-carboxylic acid methyl ester;

2-[(R)-2-((S)-2,5-dioxo-4-phenyl-imidazolidin-1-yl)-4-methyl-pentanoylamino]-thiazole-4-carboxylic acid methyl ester;

2-[(S)-2-((S)-2,5-dioxo-4-phenyl-imidazolidin-1-yl)-3-phenyl-propionylamino]-thiazole-4-carboxylic acid methyl ester;

2-[(S)-2-((R)-2,5-dioxo-4-phenyl-imidazolidin-1-yl)-4-methyl-pentanoylamino]-thiazole-4-carboxylic acid methyl ester;

2-[(S)-2-((S)-2,5-dioxo-4-phenyl-imidazolidin-1-yl)-3-naphthalen-2-yl-propionylamino]-thiazole-4-carboxylic acid methyl ester;

2-[(S)-3-biphenyl-4-yl-2-((S)-2,5-dioxo-4-phenyl-imidazolidin-1-yl)-propionylamino]-thiazole-4-carboxylic acid methyl ester;

2-[(S)-2-(2,5-dioxo-4-(2-methyl-phenyl)-imidazolidin-1-yl)-4-methyl-pentanoylamino]-thiazole-4-carboxylic acid methyl ester;

2-[(S)-2-(4-furan-2-yl-2,5-dioxo-imidazolidin-1-yl)-3-phenyl-propionylamino]-thiazole-4-carboxylic acid methyl ester;

2-[(S)-2-(4-naphthalen-2-yl-2,5-dioxo-imidazolidin-1-yl)-3-phenyl-propionylamino]-thiazole-4-carboxylic acid methyl ester;

2-{(S)-2-[4-(4-hydroxy-phenyl)-2,5-dioxo-imidazolidin-1-yl]-3-phenyl-propionylamino}-thiazole-4-carboxylic acid methyl ester;

2-{(S)-2-[4-(3-hydroxy-phenyl)-2,5-dioxo-imidazolidin-1-yl]-3-phenyl-propionylamino}-thiazole-4-carboxylic acid methyl este;

2-{(S)-2-[2,5-dioxo-4-(4-trifluoromethyl-phenyl)-imidazolidin-1-yl]-3-phenyl-propionylamino}-thiazole-4-carboxylic acid methyl ester;

2-{(S)-2-[4-(2-chloro-phenyl)-2,5-dioxo-imidazolidin-1-yl]-3-phenyl-propionylamino}-thiazole-4-carboxylic acid methyl este;

2-{(S)-2-[4-(3-methoxy-phenyl)-2,5-dioxo-imidazolidin-1-yl]-3-phenyl-propionylamino}-thiazole-4-carboxylic acid methyl ester;

2-[(S)-2-(2,5-dioxo-4-(3-methyl-phenyl)-imidazolidin-1-yl)-3-phenyl-propionylamino]-thiazole-4-carboxylic acid methyl ester;

2-[(S)-2-(2,5-dioxo-4-(4-methyl-phenyl)-imidazolidin-1-yl)-4-methyl-pentanoylamino]-thiazole-4-carboxylic acid methyl ester;

2-{(S)-2-[4-(4-isopropyl-phenyl)-2,5-dioxo-imidazolidin-1-yl]-4-methyl-pentanoylamino}-thiazole-4-carboxylic acid methyl ester;

2-{(S)-2-[4-(4-chloro-phenyl)-2,5-dioxo-imidazolidin-1-yl]-4-methyl-pentanoylamino}-thiazole-4-carboxylic acid methyl ester;

2-{(S)-2-[4-(4-methoxy-phenyl)-2,5-dioxo-imidazolidin-1-yl]-4-methyl-pentanoylamino}-thiazole-4-carboxylic acid methyl ester;

2-[(S)-2-(4-furan-2-yl-2,5-dioxo-imidazolidin-1-yl)-4-methyl-pentanoylamino]-thiazole-4-carboxylic acid methyl ester;

2-[(S)-4-methyl-2-(4-naphthalen-2-yl-2,5-dioxo-imidazolidin-1-yl)-pentanoylamino]-thiazole-4-carboxylic acid methyl ester;

2-[(S)-2-(2,5-dioxo-4-thiophen-3-yl-imidazolidin-1-yl)-4-methyl-pentanoylamino]-thiazole-4-carboxylic acid methyl ester;

2-{(S)-2-[4-(4-fluoro-phenyl)-2,5-dioxo-imidazolidin-1-yl]-4-methyl-pentanoylamino}-thiazole-4-carboxylic acid methyl ester;

2-[(S)-2-(4-benzo[1,3]dioxol-5-yl-2,5-dioxo-imidazolidin-1-yl)-4-methyl-pentanoylamino]-thiazole-4-carboxylic acid methyl ester;

2-{(S)-2-[4-(3-iodo-phenyl)-2,5-dioxo-imidazolidin-1-yl]-4-methyl-pentanoylamino}-thiazole-4-carboxylic acid methyl ester;

2-{(S)-2-[4-(4-hydroxy-phenyl)-2,5-dioxo-imidazolidin-1-yl]-4-methyl-pentanoylamino}-thiazole-4-carboxylic acid methyl ester;

2-{(S)-2-[4-(3-hydroxy-phenyl)-2,5-dioxo-imidazolidin-1-yl]-4-methyl-pentanoylamino}-thiazole-4-carboxylic acid methyl ester;

2-{(S)-2-[2,5-dioxo-4-(3-trifluoromethyl-phenyl)-imidazolidin-1-yl]-4-methyl-pentanoylamino}-thiazole-4-carboxylic acid methyl ester;

2-{(S)-2-[4-(2-methoxy-phenyl)-2,5-dioxo-imidazolidin-1-yl]-4-methyl-pentanoylamino}-thiazole-4-carboxylic acid methyl ester;

2-{(S)-2-[4-(2-chloro-phenyl)-2,5-dioxo-imidazolidin-1-yl]-4-methyl-pentanoylamino}-thiazole-4-carboxylic acid methyl ester;

2-{(S)-2-[4-(2-fluoro-phenyl)-2,5-dioxo-imidazolidin-1-yl]-4-methyl-pentanoylamino}-thiazole-4-carboxylic acid methyl ester;

2-{(S)-2-[4-(3-fluoro-phenyl)-2,5-dioxo-imidazolidin-1-yl]-4-methyl-pentanoylamino}-thiazole-4-carboxylic acid methyl ester;

2-{(S)-2-[4-(3-methoxy-phenyl)-2,5-dioxo-imidazolidin-1-yl]-4-methyl-pentanoylamino}-thiazole-4-carboxylic acid methyl ester;

2-[(S)-2-(2,5-dioxo-4-(3-methyl-phenyl)-imidazolidin-1-yl)-4-methyl-pentanoylamino]-thiazole-4-carboxylic acid methyl ester;

2-[(S)-2-(2,5-dioxo-4-(4-methyl-phenyl)-imidazolidin-1-yl)-3-phenyl-propionylamino]-thiazole-4-carboxylic acid methyl ester;

2-[2-(2,5-dioxo-4-thiophen-3-yl-imidazolidin-1-yl)-3-phenyl-propionylamino]-thiazole-4-carboxylic acid methyl ester;

2-{(S)-2-[4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[4-(2,3-dihydro-benzo[1,4]dioxin-6-yl)-2,5-dioxo-imidazolidin-1-yl]-3-phenyl-propionylamino}-thiazole-4-carboxylic acid methyl ester;

2-{(S)-2-[4-(2,3-dihydro-benzo[1,4]dioxin-5-yl)-2,5-dioxo-imidazolidin-1-yl]-3-phenyl-propionylamino}-thiazole-4-carboxylic acid methyl ester;

2-{(S)-2-[4-(2,3-dihydro-benzofuran-5-yl)-2,5-dioxo-imidazolidin-1-yl]-3-phenyl-propionylamino}-thiazole-4-carboxylic acid methyl ester;

2-{(S)-2-[4-(3,4-dimethoxy-phenyl)-2,5-dioxo-imidazolidin-1-yl]-3-phenyl-propionylamino}-thiazole-4-carboxylic acid methyl ester;

2-{(S)-2-[4-(2,3-difluoro-phenyl)-2,5-dioxo-imidazolidin-1-yl]-3-phenyl-propionylamino}-thiazole-4-carboxylic acid methyl ester;

2-{(S)-2-[4-(2,4-difluoro-phenyl)-2,5-dioxo-imidazolidin-1-yl]-3-phenyl-propionylamino}-thiazole-4-carboxylic acid methyl ester;

2-{(S)-2-[4-(3-chloro 4-methoxy-phenyl)-2,5-dioxo-imidazolidin-1-yl]-3-phenyl-propionylamino}-thiazole-4-carboxylic acid methyl ester;

2-{(S)-2-[4-(3,5-difluoro-phenyl)-2,5-dioxo-imidazolidin-1-yl]-3-phenyl-propionylamino}-thiazole-4-carboxylic acid methyl ester;

2-{(S)-2-[4-(2,6-difluoro-phenyl)-2,5-dioxo-imidazolidin-1-yl]-3-phenyl-propionylamino}-thiazole-4-carboxylic acid methyl ester;

2-{(S)-2-[4-(5-fluoro-2-methoxy-phenyl)-2,5-dioxo-imidazolidin-1-yl]-3-phenyl-propionylamino}-thiazole-4-carboxylic acid methyl ester;

2-{(S)-2-[4-(2-fluoro-4-methoxy-phenyl)-2,5-dioxo-imidazolidin-1-yl]-3-phenyl-propionylamino}-thiazole-4-carboxylic acid methyl ester;

2-{(S)-2-[4-(4-dimethylamino-phenyl)-2,5-dioxo-imidazolidin-1-yl]-3-phenyl-propionylamino}-thiazole-4-carboxylic acid methyl ester;

2-[2-(4-benzo[1,3]dioxol-5-yl-2,5-dioxo-imidazolidin-1-yl)-3-(4-cyano-phenyl)-propionylamino]-thiazole-4-carboxylic acid methyl ester;

2-[(S)-2-(4-benzo[1,3]dioxol-5-yl-2,5-dioxo-imidazolidin-1-yl)-3-(4-carbamoyl-phenyl)-propionylamino]-thiazole-4-carboxylic acid methyl ester;

2-((S)-2-{2,5-dioxo-4-[4-(2-pyrrolidin-1-yl-ethoxy)-phenyl]-imidazolidin-1-yl}-3-phenyl-propionylamino)-thiazole-4-carboxylic acid methyl ester;

2-((S)-2-{(R)-4-[4-(3-methoxy-propoxy)-phenyl]-2,5-dioxo-imidazolidin-1-yl}-3-phenyl-propionylamino)-thiazole-4-carboxylic acid methyl ester;

2-{(S)-2-[4-(1-methyl-1H-benzoimidazol-5-yl)-2,5-dioxo-imidazolidin-1-yl]-3-phenyl-propionylamino}-thiazole-4-carboxylic acid methyl ester;

2-[(S)-2-(4-benzo[1,3]dioxol-5-yl-2,5-dioxo-imidazolidin-1-yl)-3-(2-trifluoromethyl-phenyl)-propionylamino]-thiazole-4-carboxylic acid methyl ester;

2-[(S)-2-[4-(4-methylsulfanyl-phenyl)-2,5-dioxo-imidazolidin-1-yl]-3-(2-trifluoromethyl-phenyl)-propionylamino]-thiazole-4-carboxylic acid methyl ester;

2-[(S)-2-[4-(4-methanesulfinyl-phenyl)-2,5-dioxo-imidazolidin-1-yl]-3-(2-trifluoromethyl-phenyl)-propionylamino]-thiazole-4-carboxylic acid methyl ester;

2-[(S)-2-(2,5-dioxo-4-thiophen-2-yl-imidazolidin-1-yl)-3-phenyl-propionylamino]-thiazole-4-carboxylic acid methyl ester;

2-[(S)-2-[4-(2,3-dihydro-benzo[1,4]dioxin-6-yl)-2,5-dioxo-imidazolidin-1-yl]-3-(1H-indol-3-yl)-propionylamino]-thiazole-4-carboxylic acid methyl ester;

2-{(S)-2-[4-(2,2-difluoro-benzo[1,3]dioxol-5-yl)-2,5-dioxo-imidazolidin-1-yl]-3-phenyl-propionylamino}-thiazole-4-carboxylic acid methyl ester;

2-{(S)-2-[4-(3,5-dimethoxy-phenyl)-2,5-dioxo-imidazolidin-1-yl]-3-phenyl-propionylamino}-thiazole-4-carboxylic acid methyl ester;

2-[(S)-2-(4-benzo[1,3]dioxol-5-yl-2,5-dioxo-imidazolidin-1-yl)-3-pyridin-3-yl-propionylamino]-thiazole-4-carboxylic acid methyl ester;

2-[2-(4-benzo[1,3]dioxol-5-yl-2,5-dioxo-imidazolidin-1-yl)-3-(tetrahydro-pyran-4-yl)-propionylamino]-thiazole-4-carboxylic acid methyl ester;

2-[(S)-2-(4-benzo[1,3]dioxol-5-yl-2,5-dioxo-imidazolidin-1-yl)-3-(1-methyl-1H-imidazol-4-yl)-propionylamino]-thiazole-4-carboxylic acid methyl ester;

2-[(S)-2-[4-(2,3-dihydro-benzo[1,4]dioxin-6-yl)-2,5-dioxo-imidazolidin-1-yl]-3-(4-methanesulfonylamino-phenyl)-propionylamino]-thiazole-4-carboxylic acid methyl ester;

2-[(S)-2-(4-benzo[1,3]dioxol-5-yl-2,5-dioxo-imidazolidin-1-yl)-3-phenyl-propionylamino]-thiazole-4-carboxylic acid methyl ester;

2-{(S)-2-[4-(2-fluoro-4-methoxy-phenyl)-2,5-dioxo-imidazolidin-1-yl]-4-methyl-pentanoylamino}-thiazole-4-carboxylic acid methyl ester;

2-{(S)-2-[4-(2,3-difluoro-phenyl)-2,5-dioxo-imidazolidin-1-yl]-4-methyl-pentanoylamino}-thiazole-4-carboxylic acid methyl ester;

2-{(S)-2-[4-(2-fluoro-4-methoxy-phenyl)-2,5-dioxo-imidazolidin-1-yl]-4-methyl-pentanoylamino}-thiazole-4-carboxylic acid methyl ester;

2-{3-cyclopentyl-(S)-2-[4-(3-fluoro-4-methoxy-phenyl)-2,5-dioxo-imidazolidin-1-yl]propionylamino}-thiazole-4-carboxylic acid methyl ester;

(S)-2-[2-(4-benzo[1,3]dioxol-5-yl-2,5-dioxo-imidazolidin-1-yl)-3-cyclopentyl-propionylamino]-thiazole-4-carboxylic acid methyl ester;

(S)-2-[2-(4-benzo[1,3]dioxol-5-yl-2,5-dioxo-imidazolidin-1-yl)-3-cyclopropyl-propionylamino]-thiazole-4-carboxylic acid methyl ester;

(S)-2-[2-(4-benzo[1,3]dioxol-5-yl-2,5-dioxo-imidazolidin-1-yl)-4-methanesulfonyl-butyrylamino]-thiazole-4-carboxylic acid methyl ester;

2-[(S)-2-(4-benzo[1,3]dioxol-5-yl-2,5-dioxo-imidazolidin-1-yl)-3-(3-chloro-phenyl)-propionylamino]-thiazole-4-carboxylic acid methyl ester;

2-[(S)-2-(4-benzo[1,3]dioxol-5-yl-2,5-dioxo-imidazolidin-1-yl)-3-(2-chloro-phenyl)-propionylamino]-thiazole-4-carboxylic acid methyl ester;

2-[(S)-2-[4-(2,3-dihydro-benzo[1,4]dioxin-6-yl)-2,5-dioxo-imidazolidin-1-yl]-3-(2-methoxy-phenyl)-propionylamino]-thiazole-4-carboxylic acid methyl ester;

2-[(S)-2-(4-benzo[1,3]dioxol-5-yl-2,5-dioxo-imidazolidin-1-yl)-3-(3-methoxy-phenyl)propionylamino]-thiazole-4-carboxylic acid methyl ester;

2-[(S)-2-[4-(3-fluoro-4-methoxy-phenyl)-2,5-dioxo-imidazolidin-1-yl]-3-(2-methoxy-phenyl)-propionylamino]-thiazole-4-carboxylic acid methyl ester;

2-[(S)-2-(4-benzo[1,3]dioxol-5-yl-2,5-dioxo-imidazolidin-1-yl)-3-(4-methoxy-phenyl)propionylamino]-thiazole-4-carboxylic acid methyl ester;

2-[(S)-2-(4-benzo[1,3]dioxol-5-yl-2,5-dioxo-imidazolidin-1-yl)-3-o-tolyl-propionylamino]-thiazole-4-carboxylic acid methyl ester;

2-{2-[4-(2,3-dihydro-benzo[1,4]dioxin-6-yl)-2,5-dioxo-imidazolidin-1-yl]-3-indan-1yl-propionylamino}-thiazole-4-carboxylic acid methyl ester;

2-[(S)-2-[4-(2,3-dihydro-benzo[1,4]dioxin-6-yl)-2,5-dioxo-imidazolidin-1-yl]-3-(2-fluoro-phenyl)-propionylamino]-thiazole-4-carboxylic acid methyl ester;

2-[(S)-2-[4-(2,3-dihydro-benzo[1,4]dioxin-6-yl)-2,5-dioxo-imidazolidin-1-yl]-3-(3,4-dimethoxy-phenyl)-propionylamino]-thiazole-4-carboxylic acid methyl ester;

2-[(2-[4-(2,3-dihydro-benzo[1,4]dioxin-6-yl)-2,5-dioxo-imidazolidin-1-yl]-3-(3-methoxycarbonylmethoxy-phenyl)-propionylamino]-thiazole-4-carboxylic acid methyl ester;

2-{(S)-3-benzooxazol-5-yl-2-[4-(2,3-dihydro-benzo[1,4]dioxin-6-yl)-2,5-dioxo-imidazolidin-1-yl]-propionylamino}-thiazole-4-carboxylic acid methyl ester, isomer 1;

2-{(S)-3-benzooxazol-5-yl-2-[4-(2,3-dihydro-benzo[1,4]dioxin-6-yl)-2,5-dioxo-imidazolidin-1-yl]-propionylamino}-thiazole-4-carboxylic acid methyl ester, isomer 2;

2-[(S)-2-[4-(2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester, isomer 1;

2-[(S)-2-[4-(2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester, isomer 2;

2-{(S)-2-[4-(3-fluoro-4-methoxy-phenyl)-2,5-dioxo-imidazolidin-1-yl]-3-thiazol-4-ylpropionylamino}-thiazole-4-carboxylic acid methyl ester;

2-[(S)-2-(4-benzo[1,3]dioxol-5-yl-2,5-dioxo-imidazolidin-1-yl)-3-thiazol-4-yl-propionylamino]-thiazole-4-carboxylic acid methyl ester;

2-{(S)-2-[4-(2,3-dihydro-benzo[1,4]dioxin-6-yl)-2,5-dioxo-imidazolidin-1-yl]-3-thiazol-4-yl-propionylamino}-thiazole-4-carboxylic acid methyl ester;

2-{(S)-2-[4-(3-fluoro-4-methoxy-phenyl)-2,5-dioxo-imidazolidin-1-yl]-3-furan-2-yl-propionylamino}-thiazole-4-carboxylic acid methyl ester;

2-[(S)-2-(4-benzo[1,3]dioxol-5-yl-2,5-dioxo-imidazolidin-1-yl)-3-(3-methyl-3H-imidazol-4-yl)-propionylamino]-thiazole-4-carboxylic acid methyl ester;

2-{(S)-2-[4-(2,3-dihydro-benzo[1,4]dioxin-6-yl)-2,5-dioxo-imidazolidin-1-yl]-3-pyridin-3-yl-propionylamino}-thiazole-4-carboxylic acid methyl ester;

2-{(S)-2-[(R)-4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[(S)-4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[(R)-4-(3-chloro-4-methoxy-phenyl)-2,5-dioxo-imidazolidin-1-yl]-3-phenyl-propionylamino}-thiazole-4-carboxylic acid methyl ester;

2-{(S)-2-[(R)-4-benzo[1,3]dioxol-5-yl-2,5-dioxo-imidazolidin-1-yl]-3-phenyl-propionylamino}-thiazole-4-carboxylic acid methyl ester;

2-{(S)-2-[(R)-4-(3,5-difluoro-phenyl)-2,5-dioxo-imidazolidin-1-yl]-3-phenyl-propionylamino}-thiazole-4-carboxylic acid methyl ester;

2-{(S)-2-[(R)-4-(3-fluoro-4-methoxy-phenyl)-2,5-dioxo-imidazolidin-1-yl]-3-(2-methoxy-phenyl)-propionylamino}-thiazole-4-carboxylic acid methyl ester;

2-[(S)-2-((R)-4-benzo[1,3]dioxol-5-yl-2,5-dioxo-imidazolidin-1-yl)-3-cyclopropyl-propionylamino]-thiazole-4-carboxylic acid methyl ester;

2-[(S)-2-((R)-4-benzo[1,3]dioxol-5-yl-2,5-dioxo-imidazolidin-1-yl)-3-cyclopentyl-propionylamino]-thiazole-4-carboxylic acid methyl ester;

2-{3-cyclopentyl-(S)-2-[(R)-4-(3-fluoro-4-methoxy-phenyl)-2,5-dioxo-imidazolidin-1-yl]-propionylamino}-thiazole-4-carboxylic acid methyl ester;

2-[(S)-2-((S)-2,5-dioxo-4-thiophen-3-yl-imidazolidin-1-yl)-3-phenyl-propionylamino]-thiazole-4-carboxylic acid methyl ester;

2-{(S)-2-[(R)-4-(4-methoxy-phenyl)-2,5-dioxo-imidazolidin-1-yl]-3-thiazol-2-yl-propionylamino}-thiazole-4-carboxylic acid methyl ester;

2-{(S)-2-[(R)-4-(2-fluoro-4-methoxy-phenyl)-2,5-dioxo-imidazolidin-1-yl]-3-phenyl-propionylamino}-thiazole-4-carboxylic acid methyl ester;

2-[(S)-2-(2,5-dioxo-(R)-4-phenyl-imidazolidin-1-yl)-3-phenyl-propionylamino]-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-phenyl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-(4-fluoro-phenyl)-propionylamino}-thiazole-4-carboxylic acid methyl ester;

2-{3-(3,5-difluoro-phenyl)-(S)-2-[(R)-4-(2,3-dihydro-benzo[1,4]dioxin-6-yl)-2,5-dioxo-imidazolidin-1-yl]-propionylamino}-thiazole-4-carboxylic acid methyl ester;

2-[(S)-2-[(R)-4-(2,3-dihydro-benzo[1,4]dioxin-6-yl)-2,5-dioxo-imidazolidin-1-yl]-3-(2-fluoro-phenyl)-propionylamino]-thiazole-4-carboxylic acid methyl ester;

2-{(S)-2-[(R)-4-(4-methoxy-phenyl)-2,5-dioxo-imidazolidin-1-yl]-3-phenyl-propionylamino}-thiazole-4-carboxylic acid methyl ester;

2-{3-(2-methoxy-phenyl)-(S)-2-[(R)-4-(4-methoxy-phenyl)-2,5-dioxo-imidazolidin-1-yl]-propionylamino}-thiazole-4-carboxylic acid methyl ester;

2-[(S)-2-[(R)-4-(2,3-dihydro-benzo[1,4]dioxin-6-yl)-2,5-dioxo-imidazolidin-1-yl]-3-(3-fluoro-phenyl)-propionylamino]-thiazole-4-carboxylic acid methyl ester;

2-{3-(3,4-difluoro-phenyl)-(S)-2-[(R)4-(2,3-dihydro-benzo[1,4]dioxin-6-yl)-2,5-dioxo-imidazolidin-1-yl]-propionylamino}-thiazole-4-carboxylic acid methyl ester;

2-((S)-2-{(R)-4-[4-(2-hydroxy-ethoxy)-phenyl]-2,5-dioxo-imidazolidin-1-yl}-3-phenyl-propionylamino)-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiophen-2-yl-propionylamino}-thiazole-4-carboxylic acid methyl ester;

2-{(S)-2-[(R)-4-(4-methoxy-phenyl)-2,5-dioxo-imidazolidin-1-yl]-3-thiazol-4-yl-propionylamino}-thiazole-4-carboxylic acid methyl ester;

2-{(S)-2-[(R)-4-(4-methoxy-phenyl)-2,5-dioxo-imidazolidin-1-yl]-3-thiazol-2-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiazol-4-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiophen-3-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-pyrazol-1-yl-propionylamino}-thiazole-4-carboxylic acid methyl ester;

2-{(R)-2-[(R)-4-(4-methoxy-phenyl)-2,5-dioxo-imidazolidin-1-yl]-3-phenyl-propionylamino}-thiazole-4-carboxylic acid methyl ester;

2-{(S)-2-[(S)-4-(4-methoxy-phenyl)-2,5-dioxo-imidazolidin-1-yl]-3-phenyl-propionylamino}-thiazole-4-carboxylic acid methyl ester;

2-((S)-2-{(R)-4-[4-(2-methoxy-ethoxy)-phenyl]-2,5-dioxo-imidazolidin-1-yl}-3-phenyl-propionylamino)-thiazole-4-carboxylic acid methyl ester;

2-[2-[(R)-4-(4-methoxy-phenyl)-2,5-dioxo-imidazolidin-1-yl]-3-(3-nitro-phenyl)-propionylamino]-thiazole-4-carboxylic acid methyl ester;

2-[(S)-2-[(R)-4-(4-methoxy-phenyl)-2,5-dioxo-imidazolidin-1-yl]-3-(4-nitro-phenyl)-propionylamino]-thiazole-4-carboxylic acid methyl ester;

2-{(S)-3-(4-amino-phenyl)-2-[(R)-4-(4-methoxy-phenyl)-2,5-dioxo-imidazolidin-1-yl]-propionylamino}-thiazole-4-carboxylic acid methyl ester;

2-{(S)-3-(4-dimethylamino-phenyl)-2-[(R)-4-(4-methoxy-phenyl)-2,5-dioxo-imidazolidin-1-yl]-propionylamino}-thiazole-4-carboxylic acid methyl ester;

2-[(S)-2-{4-[4-(2-methoxy-ethoxy)-phenyl]-2,5-dioxo-imidazolidin-1-yl}-3-(2-methoxy-phenyl)-propionylamino]-thiazole-4-carboxylic acid methyl ester;

2-{(S)-3-(2-cyano-phenyl)-2-[(R)-4-(4-methoxy-phenyl)-2,5-dioxo-imidazolidin-1-yl]-propionylamino}-thiazole-4-carboxylic acid methyl ester;

2-((S)-3-(2-cyano-phenyl)-2-{4-[(R)-4-(2-methoxy-ethoxy)-phenyl]-2,5-dioxo-imidazolidin-1-yl}-propionylamino)-thiazole-4-carboxylic acid methyl ester;

2-{(S)-2-[4-((R)-(4-ethoxy-phenyl))-2,5-dioxo-imidazolidin-1-yl]-3-phenyl-propionylamino}-thiazole-4-carboxylic acid methyl ester;

2-((S)-2-{(R)-4-[4-((R)-2,3-dihydroxy-propoxy)-phenyl]-2,5-dioxo-imidazolidin-1-yl}-3-phenyl-propionylamino)-thiazole-4-carboxylic acid methyl ester;

2-{(S)-2-[4-(4-methoxy-3-methyl-phenyl)-2,5-dioxo-imidazolidin-1-yl]-3-phenyl-propionylamino}-thiazole-4-carboxylic acid methyl ester;

2-{(S)-2-[4-(3-isopropyl-4-methoxy-phenyl)-2,5-dioxo-imidazolidin-1-yl]-3-phenyl-propionylamino}-thiazole-4-carboxylic acid methyl ester;

2-{(S)-2-[4-(3-ethyl4-methoxy-phenyl)-2,5-dioxo-imidazolidin-1-yl]-3-phenyl-propionylamino}-thiazole-4-carboxylic acid methyl ester;

2-{(S)-2-[(R)-4-(4-methoxy-phenyl)-2,5-dioxo-imidazolidin-1-yl]-3-phenyl-propionylamino}-thiazole-4-carboxylic acid methoxy-methyl-amide;

(S)-(4-acetyl-thiazol-2-yl)-2-(2,5-dioxo-4-phenyl-imidazolidin-1-yl)-3-phenyl-propionamide;

2-[(S)-2-(2,5-dioxo-4-phenyl-imidazolidin-1-yl)-3-phenyl-propionylamino]-thiazole-4-carboxylic acid amide and 2-[(S)-2-(2,5-dioxo-4-phenyl-imidazolidin-1-yl)-3-phenyl-propionylamino]-thiazole-4-carboxylic acid dimethylamide.

The compounds claimed in the present invention may be prepared using either solid phase synthetic methods or using solution phase reaction conditions. The methods employed for the solid phase synthesis of the claimed compounds are outlined in reaction schemes 1 and 2. The methods employed for the solution phase synthesis of the claimed compounds are outlined in schemes 3 to 8 inclusive.

Several of the steps in the synthesis of the compounds of the present invention involve the connection of amino acid containing fragments, one at a time in succession and in the desired sequence to another amino acid or residue thereof, or by a procedure whereby peptide fragments with the desired amino acid sequence are first synthesized conventionally and then condensed to provide the desired compound. Synthesis of the compounds of the present invention can be carried out by sequentially incorporating the desired amino acid residues one at a time into a growing peptide chain according to the general principles of solid phase methods [Merrifield, R. B., *J. Am. Chem. Soc.* 1963, 85, 2149-2154; Barany et al., The Peptides, Analysis, Synthesis and Biology, Vol. 2, Gross, E. and Meienhofer, J., Eds. Academic Press 1-284 (1980); Bunin, B., Combinatorial Index, Academic Press (1998)].

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group of an amino acid or fragment while that entity reacts at the carboxyl group, followed by the selective removal of the alpha amino protecting group and allow a subsequent reaction to take place at that site. While specific protecting groups are mentioned below in regard to the solid phase synthesis method, it should be noted that each amino acid can be protected by any protective group conventionally used for the respective amino acid in solution phase synthesis.

For example, alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as tert-butyloxycarbonyl (Boc), diisopropylmethoxycarbonyl, isopropoxycarbonyl, and allyloxycarbonyl. In the present case, Fmoc is the most preferred for alpha amino protection. Guanidino groups may be protected by a suitable protecting group selected from nitro, p-toluenesulfonyl (Tos), Z, pentamethylchromanesulfonyl (Pmc), adamantyloxycarbonyl, and Boc. Pmc is the most preferred for arginine (Arg).

Compounds of this invention may be prepared using solid phase synthesis following the principles and general methods described by Merrifield or by Bunin (referenced above), although other equivalent chemical synthesis techniques known in the art could be used as previously mentioned. Solid phase synthesis is commenced from the C-terminal end of the peptide by coupling a N-protected amino acid to a suitable resin. Such a starting material can be prepared by attaching a N-protected amino acid by an ester linkage to a p-benzyloxybenzyl alcohol (Wang) resin, or by an amide bond between an Fmoc-Linker, such as p-[(R,S)-α-[1-(9H-fluoren-9-yl)-methoxyformamido]-2,4-dimethyloxybenzyl]-phenoxyacetic acid (Rink linker) to a benzhydrylamine (BHA) resin. Preparation of the hydroxymethyl resin is well known in the art. Wang resin supports are commercially available and generally used when the desired peptide being synthesized has an ester or a substituted amide at the C-terminus. To form the starting resin bound amino acid, a Fmoc N-protected amino acid is activated by the formation of a mixed anhydride which in turn couples with the hydroxymethyl resin though an ester bond. Several reagents are used to form mixed anhydrides in which the carbonyl group originating from the C-terminal amino acid is preferentially activated to nucleophilic attack by the hydroxymethyl residues in the Wang resin, through either electronic or steric effects. For example, appropriate compounds used in the formation of the mixed anhydrides are trimethylacetyl chloride, 2,6-dichlorobenzoyl chloride and 2,4,6-trichlorobenzoyl chloride, preferably 2,6-dichlorobenzoyl chloride.

Subsequently, the amino acids or mimetics are then coupled onto the Wang resin using the Fmoc protected form of the amino acid or mimetic, with 2-5 equivalents of amino acid and a suitable coupling reagent. After each coupling, the resin may be washed and dried under vacuum. Loading of the amino acid onto the resin may be determined by amino acid analysis of an aliquot of deprotected amino acid or peptide still bound to the resin or by determination of Fmoc groups by specroscopic methods e.g. UV analysis.

The resins are carried through one or two cycles to add amino acids sequentially. In each cycle, the N-terminal Fmoc protecting group is removed under basic conditions from the resin bound amino acid. A secondary amine base such as piperidine, piperazine or morpholine, preferably piperidine (20-40% v/v) in an inert solvent, for example, N,N-dimethylformamide is particularly useful for this purpose. Following the removal of the alpha amino protecting group, the subsequent protected amino acids are coupled stepwise in the desired order to obtain an N-Fmoc protected peptide-resin. The activating reagents used for coupling of the amino acids in the solid phase synthesis of the peptides are well known in the art. For example, appropriate coupling reagents for such syntheses are [(benzotriazol-1-yl)oxy]tris (dimethylamino) phosphonium hexafluorophosphate (BOP), [(benzotriazol-1-yl)oxy]tris(pyrrolidino)-phosphonium hexafluorophosphate. (PyBOP), O-(1H-benzotriazole-1-yl)-N,N,N',N'-tetramethyluronium hexafluorophosphate (HBTU), and diisopropylcarbodiimide (DIC), preferably HBTU and DIC. Other activating agents as described by Barany and Merrifield [The Peptides, Vol. 2, J. Meienhofer, ed., Academic Press, 1979, pp 1-284] may be utilized. The couplings are conveniently carried out in an inert solvent, such as N,N-dimethylformamide or N-methylpyrrolidinone, preferably N-methylpyrrolidinone, optionally in the presence of a substance that minimizes racemization and inreases the rate of reaction. Among such substances are 1-hydroxybenzotriazole (HOBT), 3,4-dihydro-3-hydroxy-4-oxo-1,2,3-benzotriazine (HOOBT), 1-hydroxy-7-azabenzotriazole (HOAT), and N-hydroxysuccinimide (HOSu). In the present instance, HOBT is preferred.

The protocol for a typical coupling cycle is as follows (Method A):

| Step | Reagent | Time |
| --- | --- | --- |
| 1 | 20% piperidine/N,N-dimethylformamide | 30 minutes |
| 2 | N,N-dimethylformamide | 3 × 30 seconds |
| 3 | methanol | 3 × 30 seconds |
| 4 | dichloromethane | 3 × 30 seconds |
| 5 | coupling | overnight |
| 6 | N,N-dimethylformamide | 3 × 30 seconds |
| 7 | methanol | 3 × 30 seconds |
| 8 | dichloromethane | 3 × 30 seconds |

Solvents for all washings and couplings may be measured to volumes of, for example, 10-20 ml/g resins. Coupling reactions throughout the synthesis may be monitored by assays, such as the Kaiser ninhydrin test, to determine extent of completion [Kaiser et at. *Anal. Biochem.* 1970, 34, 595-598].

When the requisite number of amino acid units have been assembled on the resin, the N-terminal Fmoc group may be cleaved using Steps 1-4 of Method A and the deprotected amine is reacted with phosgene or a phosgene equivalent to form an isocyanate. The reagent of choice in this transformation is trichloromethyl chloroformate (diphosgene). The reaction is carried out in an inert solvent, for example dichloromethane, in the presence of a proton acceptor. When a suspension of the resin bound isocyanate is heated, cyclization occurs wherein the isocyanate moiety condenses with the nitrogen of the neighboring amide group to form a 2,5-dioxoimidazolidine ring.

The compounds may be cleaved from the resin by the following procedure, conditions which also remove other protecting groups if they are present. The peptide-resins are shaken in a mixture (1:1) of trifluoroacetic acid in dichloromethane, optionally in the presence of a cation scavanger, for example ethanedithiol, dimethylsulfide, anisole or triethylsilane, at room temperature for 60 minutes The cleavage solution may be filtered free from the resin, concentrated to dryness, and the product then used per se in subsequent transformations.

By application of the typical solid phase reaction procedures described above compounds of general formula 1a can be prepared as outlined in scheme 1, wherein R3 and R4 are as previously described, R5 is lower alkoxy and $PG_1$, $PG_2$ and $PG_3$ are amine protecting groups which may or may not be equivalent, that are removable under conditions compatible with the Linker-O bond.

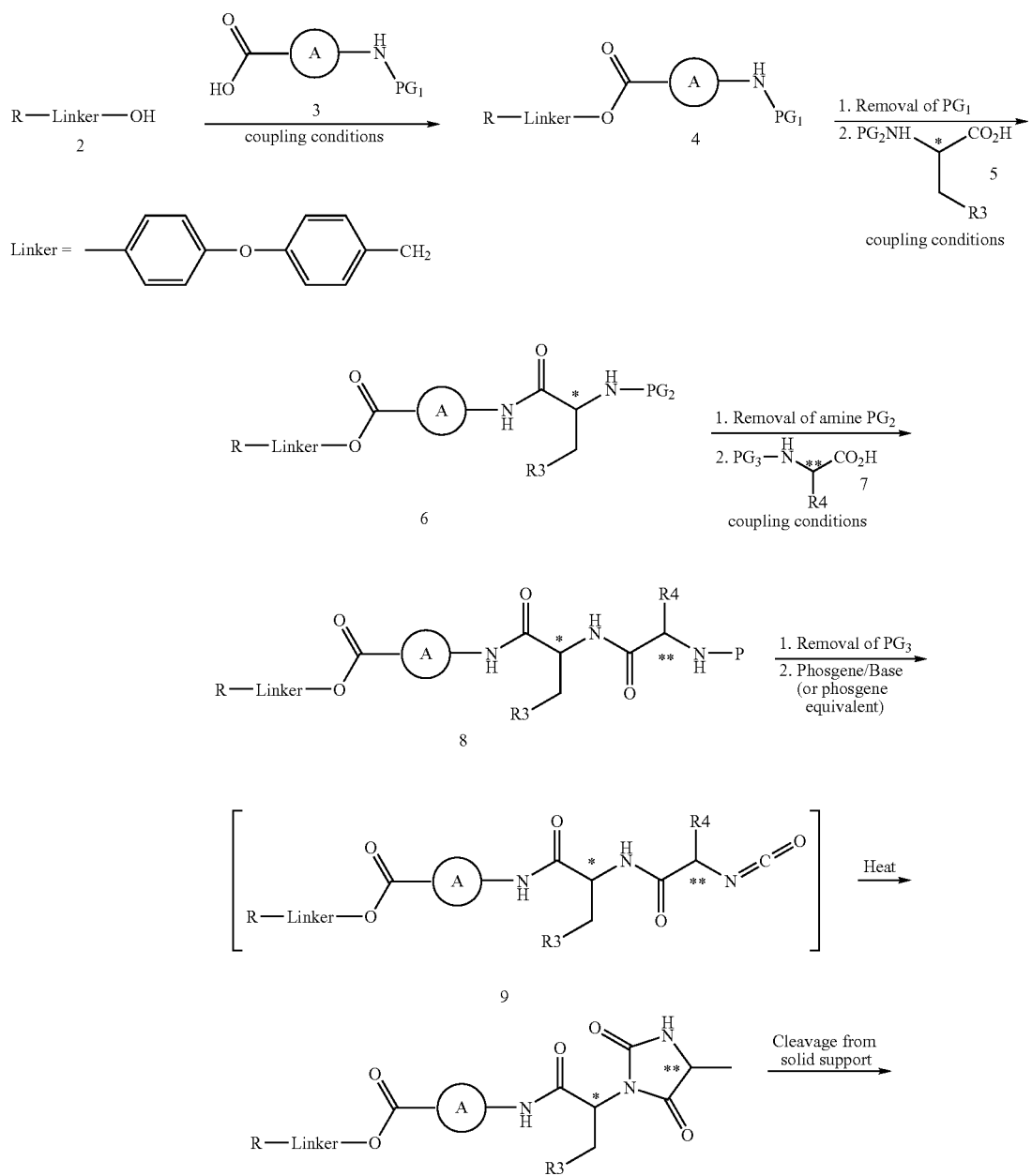

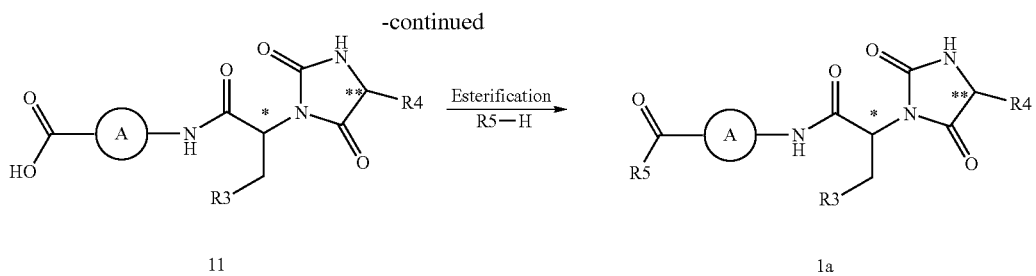

In scheme 1, an N-protected-amino acid 3 is converted to a mixed anhydride on treatment with 2,6-dichlorobenzoyl chloride in the presence of Wang resin 2 and a proton acceptor, such as triethylamine, diisopropylethylamine or pyridine, preferably pyridine to give the resin bound amino acid of structure 4. The reaction is conveniently carried out in an inert solvent for example N,N-dimethylformamide or N-methylpyrrolidinone, preferably N-methylpyrrolidinone at from 0° C. to room temperature, most conveniently at room temperature.

The conversion of 4 to the resin bound compound of structure 6 can be achieved by using the protocol outlined in Method A. Thus after N-deprotection of the resin bound amino acid of structure 4 (with piperidine in N,N-dimethylformamide when $PG_1$ is Fmoc), the product is then acylated with the N-protected α-amino acid of structure 5 in the presence of diisopropylcarbodiimide and HOBT in N-methylpyrrolidinone. The deprotection and N-acylation is carried out at a temperature between about 0° C. and about room temperature, preferably at about room temperature. By using the coupling cycle described above for the conversion of compounds of general formula 4 to compounds of general formula 6 the N-protected α-amino acid of general formula 5 is incorporated into the resin bound compound of general structure 6. By iterative use of this reaction sequence compounds of general structure 6 are converted into compounds of general structure 8 by deprotection and coupling with N-protected α-amino acid of general structure 7.

The N-terminal protecting group $PG_3$ in compounds of general formula 8 was removed and the free amine thus liberated then reacted with phosgene or a phosgene equivalent reagent, to ultimately yield in a two step sequence, the 2,5-dioxoimidazolidines of general structure 10. The reaction to give the intermediate isocyanate 9 is conveniently carried out using trichloromethyl chloroformate (diphosgene) in an inert solvent, for example, a halogenated hydrocarbon in the presence of a proton acceptor, for example, pyridine, triethylamine or diisopropylethylamine, preferably diisopropylethylamine at a temperature between about 0° C. and about room temperature, preferably at about room temperature. The thermally induced cyclization of the intermediate isocyanates is performed by heating a suspension of the resin bound isocyanates of general structure 9 in an inert solvent, for example toluene, at a temperature of from between 50° C. and the reflux temperature of the mixture, preferably at about 70° C. to give the resin bound compounds of general structure 10.

Cleavage of the assembled peptidic residues of general structure 10 from the solid support to give the carboxylic acids of general structure 11 is achieved by shaking a suspension of compound of general formula 10 in a strong acid, for example methanesulfonic acid, hydrofluoric acid or trifluoroacetic acid, preferably trifluoroacetic acid optionally in the presence of a cation scavenger and an inert co-solvent, for example dichloromethane. The reaction is conveniently run at a temperature between about 0° C. and about room temperature, preferably at about room temperature.

To complete the synthesis, the carboxylic acids of general structure 11 are reacted with an alcohol (R5-H, R5=lower alkoxy) to form the esters of general formula. The esterification can be accomplished using many of the methods well known to those of average skill in the field of organic chemistry. The conversion is conveniently carried out using a coupling reagent, for example one of the many useful carbodiimides, preferably the water soluble 1-(3-dimethylaminopropyl)-3-ethylcarbodiimide, optionally using R5-H (R5=lower alkoxy) or a mixture of R5-H and an inert co-solvent, e.g., dichloromethane, as the reaction medium. The reaction is run at a temperature between about 0° C. and about room temperature, preferably at about room temperature.

In the case where the N-protected α-amino acids of general formulae 5 and 7 coritain a chiral center at the positions labeled * and ** respectively, the chirality at these positions will be carried through into subsequent derivatives in the absence of any isomerization occurring at either or both chiral centers during the reaction sequence or compound isolation. Any isomerization which occurs at either or both chiral centers will decrease the stereochemical purity at the chiral center involved and may result in complete racemization of te center involved. Therefore, the desired configuration for the labeled centers in intermediates of general formula 6, 8, 9, 10 and 11 and in final compounds of general formula 1a is determined by the choice of configuration of amino acids 5 and 7.

In the case where the group A in compounds of general formulae 3, 4, 6, 8, 9, 10, 11 and 1a in scheme 1 is a thiazole with an amine substituent at the 2-position of the ring, the final product of the synthetic scheme, compounds of general formula 1a, are equivalent with compounds of general formula I (R5=lower alkoxy). The preparation of N-Fmoc-aminothiazole-4-carboxylic acid 15, for use in place of compound 3 in scheme 1, is summarized in scheme 2 and has been reported by Le, K. et al., *Sym. Commun.* 2004, 34(10), 1891.

derivatives of general formula 18 are prepared in a form suitable for solution phase synthesis of compounds of general formula I.

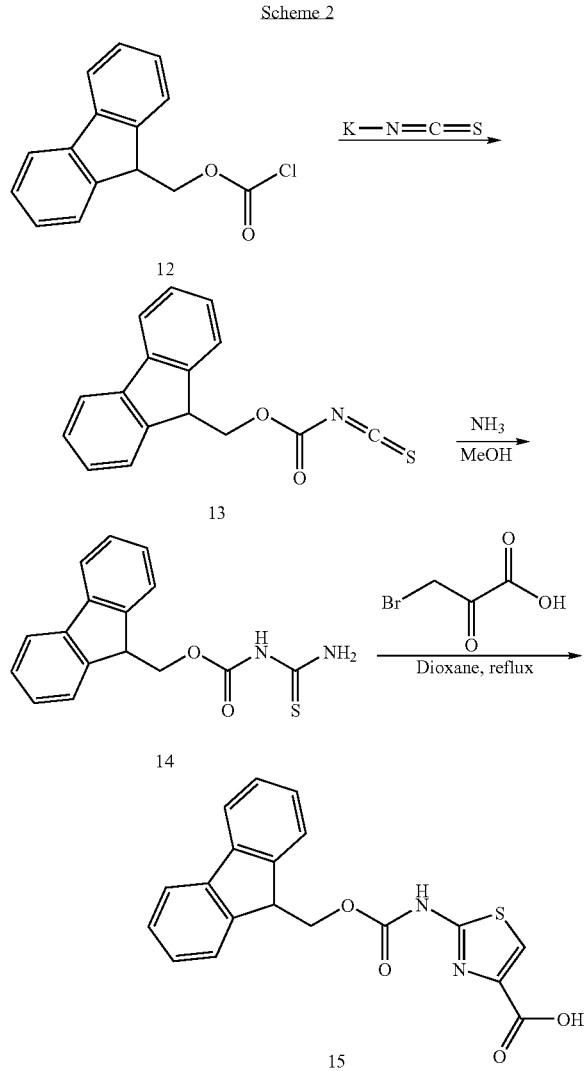

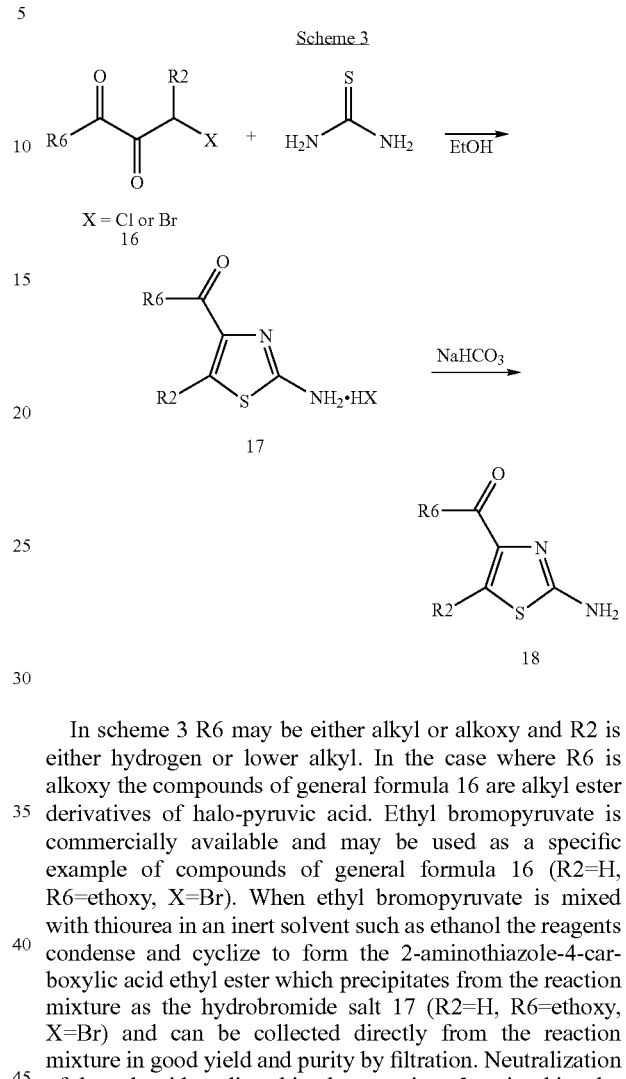

Initially 9-fluorenylmethoxycarbonyl chloride (Fmoc chloride) 12 is reacted with potassium thiocyanate in an inert solvent, preferably ethyl acetate at a temperature of between 0 and 5° C. Then the reaction is allowed to proceed at a temperature of from 0 to 40° C., preferably at room temperature to furnish N-Fmoc-thiocyanate 13. Treatment of 13 with a solution of ammonia in an inert solvent, for example methanol or ethanol, preferably methanol at a temperature of from 0° C. to room temperature, preferably 0° C., afforded N-Fmoc-thiourea 14. In the final step of scheme 2, the thiourea 14 is then reacted with bromopyruvic acid to form the thiazole of structure 15. The reaction is conveniently carried out in an inert solvent, such as a cyclic ether, for example tetrahydrofuran or dioxane, preferably dioxane at a temperature of from 40° C. to the reflux temperature of the mixture preferably at about 70° C.

The compounds claimed in the present invention may also be prepared using solution phase methods which are closely analogous to those described above for the solid phase synthesis. As shown in scheme 3, the 2-aminothiazole In scheme 3 R6 may be either alkyl or alkoxy and R2 is either hydrogen or lower alkyl. In the case where R6 is alkoxy the compounds of general formula 16 are alkyl ester derivatives of halo-pyruvic acid. Ethyl bromopyruvate is commercially available and may be used as a specific example of compounds of general formula 16 (R2=H, R6=ethoxy, X=Br). When ethyl bromopyruvate is mixed with thiourea in an inert solvent such as ethanol the reagents condense and cyclize to form the 2-aminothiazole-4-carboxylic acid ethyl ester which precipitates from the reaction mixture as the hydrobromide salt 17 (R2=H, R6=ethoxy, X=Br) and can be collected directly from the reaction mixture in good yield and purity by filtration. Neutralization of the salt with sodium bicarbonate gives 2-aminothiazole-4-carboxylic acid ethyl ester as the free base 18 (R6=ethoxy) which can then be functionalized further at the reactive primary amino group as described herein.

In compounds of general formula 18 the R6 substituent taken together with the carbonyl group to which it is attached is equivalent to substituent R1 shown in compounds of general formula I and the R6 substituent is equivalent with R5 as previously described. The same correlation is also true for derivatives prepared from compounds of general formula 18.

When the desired R6 group in compounds of general formula 18 is an alkoxy group other than ethoxy these compounds may be obtained by effecting a trans-esterification reaction between compounds of general formula 18 and the appropriate alcohol using typical procedures known to one skilled in the art. In the specific case where the desired R6 group is methoxy, the trans-esterification is most conveniently performed under basic conditions e.g. using sodium methoxide.

In the specific case where R6 is methyl, compound 16 (X=Cl) may be prepared from butan-2,3-dione and sulfuryl chloride according to the procedure of Bonnema, J. et al., *Recl. Trav. Chim. Pays-Bas* 1960, 79, 1137.

In the more general case where R6 is alkyl, compounds of general formula 18 can be prepared via the Weinreb amide of general formula 21 as shown in scheme 4.

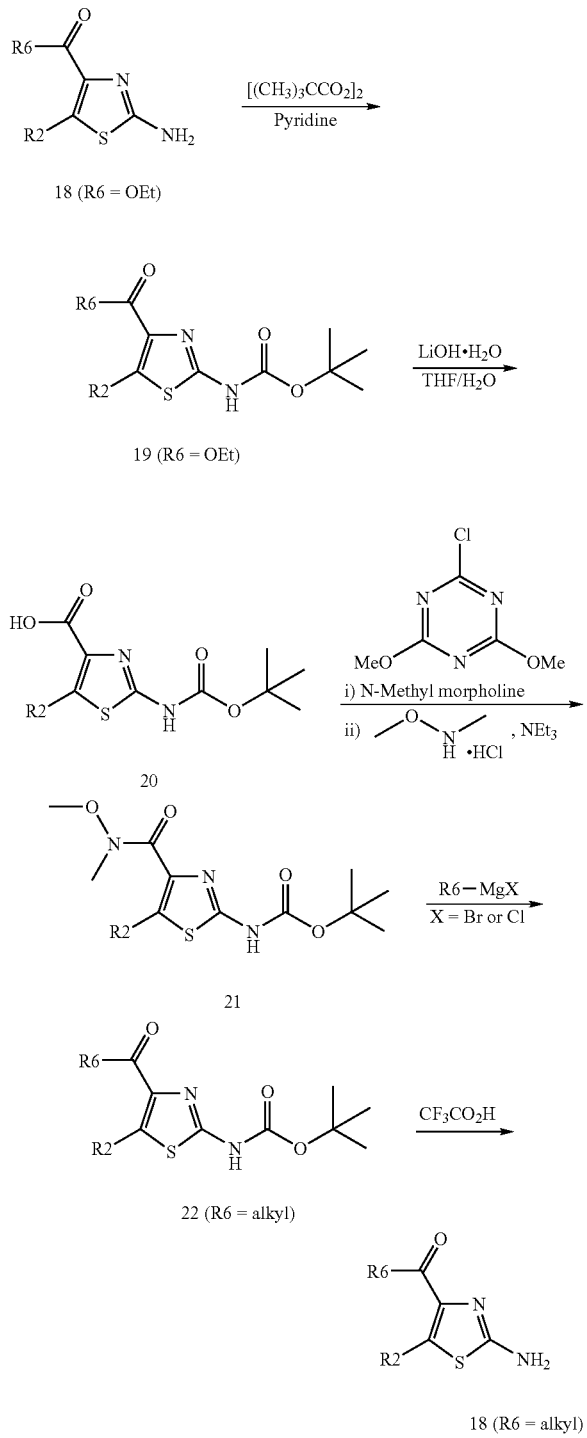

As set forth in scheme 4, 2-aminothiazole-4-carboxylic acid ethyl ester 18 (R6=OEt) when treated with di-tert-butyl dicarbonate in refluxing pyridine gave compound 19 (R6=OEt). Compound 19 (R6=OEt) was then hydrolyzed with lithium hydroxide in a mixture of tetrahydrofuran and water to give the corresponding carboxylic acid 20. Compound 20 was first reacted with 2-chloro-4,5-dimethoxy-1,3,5-triazine and N-methylmorpholine in tetrahydrofuran, then with the N,O-dimethylhydroxylamine hydrochloride and triethylamine to give the compound with formula 21. Compound 21 can be converted to ketones of general formula 22 using alkyl magnesium chloride or bromide salts (Grignard reagents) in ethereal solvents. Compounds of general formula 18 (R6=alkyl) are then obtained after treatment of compounds of general formula 22 with acid to effect removal of the tert-butyloxycarbonyl group e.g trifluoroacetic acid.

When compounds of general formula 18 are desired in which R6=alkoxyalkyl substituted amine they may be prepared by methods analogous to that used for the preparation of the Weinreb amide 21 followed by removal of the tert-butyloxycarbonyl protecting group under typical conditions e.g. trifluoroacetic acid.

When compounds of general formula 18 are desired in which R6=amine or substituted amine they may be prepared either by direct condensation of the appropriate amine with the ester of general formula 19 (R=OEt) with concomitant elimination of ethanol or by coupling of the carboxylic acid of general formula 20 with the appropriate amine using either a peptide coupling reagent as previously described or by preactivation of the carboxylic acid e.g. conversion to the acid chloride derivative of the carboxylic acid.

The 2-aminothiazole derivatives of general formula 18 prepared as shown in schemes 3 or 4 can then be incorporated into the solution phase synthetic sequence outlined in scheme 5.

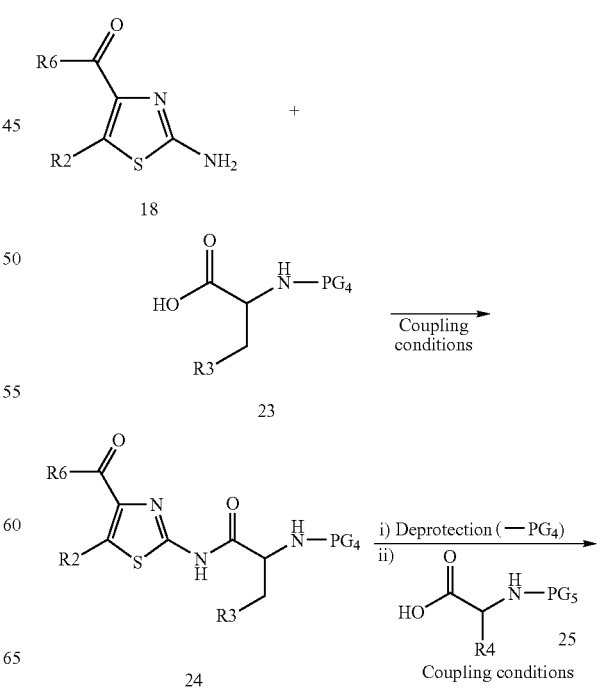

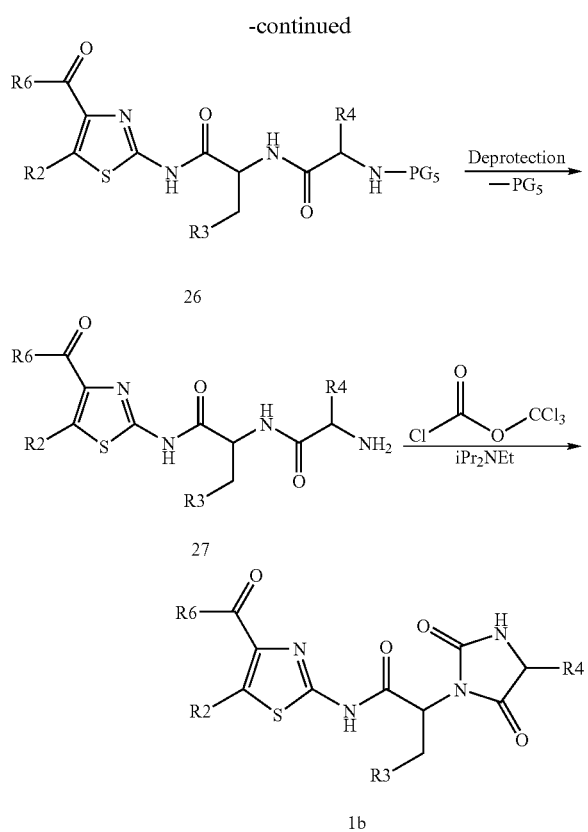

by a procedure whereby peptide fragments with the desired amino acid sequence are first synthesized conventionally and then condensed to provide the desired compound.

2-Aminothiazole derivatives of general formula 18 may be coupled with suitably protected amino acid derivatives of general formula 23 using a variety of standard amino acid coupling conditions which are known in the art. R3 can be selected from the group consisting of alkyl, cycloalkyl, heterocycle, aryl or heteroaryl, and substituted heterocycle, heteroaryl and aryl. In the case where R3 contains a functional group which is incompatible with the reaction conditions employed in subsequent steps of reaction scheme 5 it may be necessary to protect the functional group present in R3 with a group which is stable to the conditions employed in subsequent steps of scheme 5 but which may be removed using conditions which do not effect the rest of the molecule. Removal of the protecting group can be done at the end of the synthetic sequence i.e. on molecules of general formula 1b, or at an earlier stage of the synthesis when there are no subsequent steps to perform where the now liberated functional group present in R3 will interfer with reactions still to be performed. Appropriate protecting groups are as have been described previously for the solid phase synthetic approach shown in scheme 1 and additionally as described in Protecting Groups in Organic Synthesis, 3$^{rd}$ Edition, T. W. Greene and P. G. M. Wuts, Wiley-Interscience. Preferred protecting groups for the α-amino group (PG$_4$ in scheme 5) are tert-butyloxycarbonyl (Boc) and 9-fluorenylmethoxycarbonyl (Fmoc).

Typical coupling conditions which may be employed for the coupling of compounds of general formula 18 with compounds of general formula 23 to give compounds of general formula 24 are as have been described previously for the solid phase synthetic approach shown in scheme 1, preferred coupling conditions are 1-hydroxybenzotriazole (HOBT), O-benzotriazol-1-yl-N,N,N',N'-tetramethyluroniumhexaflurorophosphate (HBTU), a stoichiometric amount of base such as diisopropylethylamine in an inert solvent such as N,N-dimethylformamide or using 1-(3-dimethylaminopropyl)-3-ethylcarbodiimide hydrochloride (EDCI) in an inert solvent such as dichloromethane. Alternatively the coupling may be performed by derivatizing compounds of general formula 23 so that they are reactive acylating agents e.g. by formation of the acyl fluoride derivative. Reaction of acylating agents prepared from compounds of general formula 23 with 2-aminothiazole derivatives of general formula 18 may be performed at room temperature or by heating e.g. using a standard heating bath, heating mantle or by microwave irradiation.

Removal of protecting group PG$_4$ from compounds of general formula 24 liberates a primary amine which can be condensed with a protected amino acid derivative 25 to give compounds of general formula 26. In the case where PG$_4$=Boc in compounds of general formula 24 the deprotection can be performed under acidic conditions e.g. trifluoroactic acid either neat or in an inert solvent such as dichloromethane, and in the case where PG$_4$=Fmoc in compounds of general formula 24 the deprotection can be performed under basic conditions e.g. piperidine in N,N-dimethylformamide. Preferred embodiments for protecting group PG$_5$ in compounds of general formula 25 are the same as for protecting group PG$_4$ described previously i.e. Boc and Fmoc. Preferred coupling conditions are either 1-hydroxybenzotriazole (HOBT), O-benzotriazol-1-yl-N,N,N', N'-tetramethyluroniumhexaflurorophosphate (HBTU), a stoichiometric amount of base such as diisopropylethylamine in an inert solvent such as N,N-dimethylformamide or 1-(3-dimethylaminopropyl)-3-ethylcarbodiimide hydrochloride (EDCI) in an inert solvent such as dichloromethane.

Primary amine containing compounds of general formula 27 are obtained by removal of protecting group PG$_5$ from compounds of general formula 26. Preferred embodiments of PG$_5$ and methods of deprotection are the same as previously described for PG$_4$. Compounds of general formula 27 can be cyclized to give compounds of general formula 1b using phosgene or reagents equivalent to phosgene in the presence of sufficient base to sequester any acid formed as the reaction proceeds, preferred are diphosgene (trichloromethyl chloroformate) and diisopropylethylamine. The reaction to form compounds of general formula 1b is best performed in an inert solvent such as dichloromethane, tetrahydrofuran or a mixture of tetrahydrofuran and toluene.

As shown in scheme 5 the formation of the precyclization intermediate of general formula 27 is accomplished by sequential incorporation of the 2α-amino acids of general formulae 23 and 25. An alternative to this strategy is to attach a pre-formed dipeptide to the 2-aminothiazole of general formula 18. Appropriate dipeptide fragments can be prepared using protecting group strategies and coupling conditions already described and known to one skilled in the art of organic synthesis.

The protected α-amino acids of general formulae 23 and 25 used in scheme 5 may be either compounds which are commercially available, compounds which are known in the literature, compounds which may be prepared in manners which are closely analogous to methods known in the literature or as reported herein. In the case of compounds of general formula 25 R4 is chosen from the group consisting of aryl, heteroaryl, substituted aryl and substituted heteroaryl. Compounds of general formula 25 can be prepared as shown in schemes 6, 7 or 8.

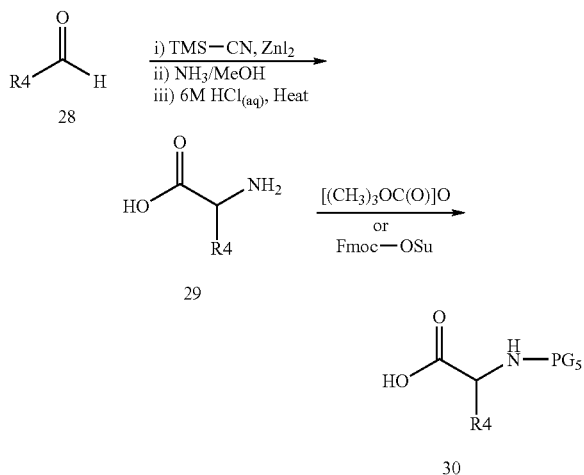

The conversion of aldehydes of general structure 28 into Boc-protected amino acids of general formula 30 is based on the modified Strecker procedure reported by K. Mai et al. *Tetrahedron Lett.* 1984, 25(41), 4583 and illustrated in scheme 6. An aldehyde of general formula 28 is reacted with trimethylsilyl cyanide in the presence of a catalytic amount of zinc iodide to form an α-cyano silanol which is then immediately converted in to an α-amino nitrile with ammonia in methanol. Hydrolysis of the nitrile under acidic conditions yields α-amino acids of general formula 29 which may be protected on either the acid or amine functional group before use in furher synthetic transformations. As shown in scheme 6 compounds of general formula 29 can be protected as either the tert-butyl or 9-fluorenylmethyl carbamates of general formula 30 ($PG_5$=Boc of Fmoc respectively) but choice of alternative protecting groups may be appropriate depending on the subsequent reaction chemistries to be employed.

Compounds of general formula 30 in scheme 6 are equivalent with compounds of general formula 25 in scheme 5.

In the case when the chosen R4 is chemically unstable towards the conditions employed in scheme 6 it may be necessary to either modify the reactions conditions employed to effect the desired transformation without causing chemical modification to R4 or to use R4 which contains labile chemical functionality in a protected form. Deprotection of R4 can be accomplished at any step in the synthetic sequence following the step which causes undesirable chemical modification to occur to R4. The modification of reaction conditions to avoid undesired side reactions and the use of protecting groups are known in the art and to, practitioners knowledgable in the field. In addition R4 shown in scheme 6 may contain one or more reactive chemical groups which are amenable to further chemical modification. Chemical modification of reactive chemical grouping present in R4 may be performed at any appropriate point in the synthetic sequence after the introduction of the R4 group.

The preferred choice for R4 in scheme 6 is from the group of aryl, heteroaryl, substituted aryl and substituted heteroaryl. Compounds of general formula 30 contain a chiral center at the α-carbon to which the R4 group is attached. Using the conditions outlined in scheme 6 there is no control over the absolute stereochemistry of the α-carbon, that is to say that compounds of general formula 30 are obtained as a racemic mixture. Resolution of compounds of general formula 30 or compounds prepared from compounds of general formula 30 may be possible after compounds of general formula 30 have been chemically combined with other enantiomerically enriched chiral molecules. Such chemical combination may be in the form of reversible formation of diastereomeric salts with enantiomerically enriched acids or bases. Such chemical combination may also take the form of covalent bond formation to a molecule containing an enantiomerically enriched chiral center. In addition to the specific resolution procedures described in this invention specific examples have been reported in the literature and the general principles for resolution of racemic compounds containing ionizable groups, either acidic or basic, are within the scope and knowledge of one skilled in the art.

Substituted phenylglycine derivatives may also be prepared by electrophilic addition to sufficiently electron rich aromatic rings as shown in scheme 7 in a manner similar to that reported by E. Bohme et al., *J. Med. Chem.* 1980, 23, 405.

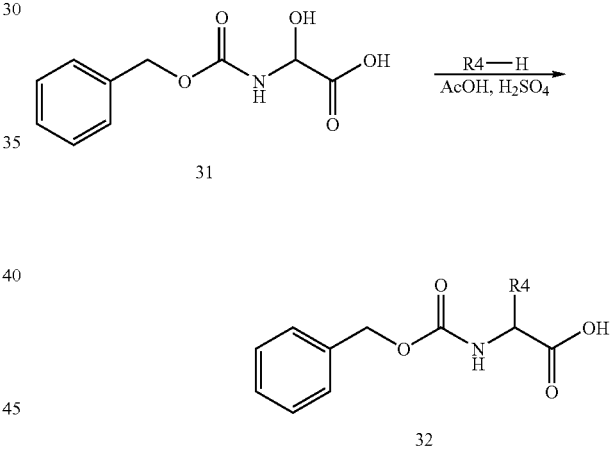

In scheme 7 R4 is an electron rich aromatic ring such as a substituted aryl or heteroaryl ring where the substituents are electron donating in nature e.g. alkyl or alkoxy. Compounds of general formula 32 are identical with compounds of general formula 25 in scheme 5 with $PG_5$=benzyloxycarbonyl. Compounds of general formula 32 are N-protected phenylglycine derivatives which are chiral at the α-carbon and are produced in racemic form because there is no control over the absolute stereochemistry. As mentioned above, racemic compounds of general formula 32 may be separated into their individual isomers by resolution of diastereomeric adducts or compounds.

In addition R4 shown in scheme 7 may contain one or more reactive chemical groups which are amenable to further chemical modification. Chemical modification of reactive chemical grouping present in R4 may be performed at any appropriate point in the synthetic sequence after the introduction of the R4 group.

Scheme 8

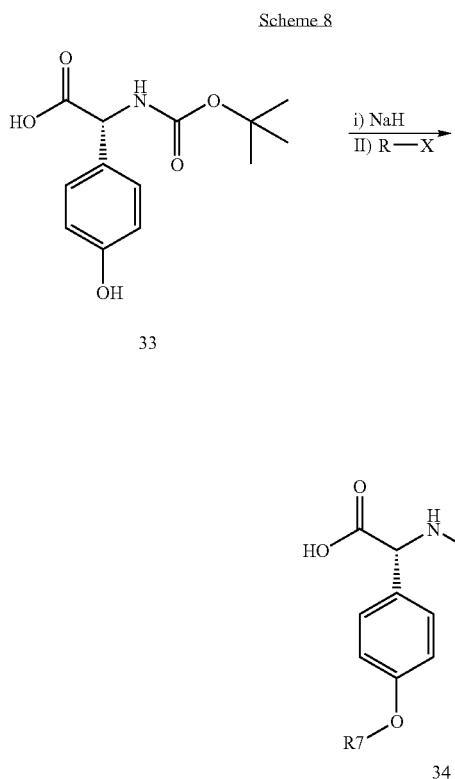

Substituted phenylglycine derivatives may also be prepared by reaction of 4-hydroxyphenylglycine derivatives of general formula 33 as shown in scheme 8. Both enantiomers of 4-hydroxyphenylglycine are commercially available and can be derivatized at the phenolic hydroxy group without loss of stereochemical purity according to the procedure of M. H. Hyun et al., *J. Liq. Chrom. & Rel. Technol.* 2002, 25, 573 as shown in scheme 8. In scheme 8 the functionalization of a phenylglycine derivative with R absolute stereochemistry is depicted but the reaction sequence is equally applicable to the S isomer of 4-hydroxyphenylglycine or to a mixture of both isomers.

Compounds with general formula 34 in scheme 8 are equivalent with compounds 25 in scheme 5 when R4 is 4-hydroxyphenyl or a derivative there of and PG$_5$=tert-butyloxycarbonyl.

The reaction conditions for the above reactions can vary to a certain extent. Methods to perform the above described reactions and processes are known in the art or can be deduced in analogy from the examples. Starting materials are commercially available or can be made by methods analogous to those described in the examples.

The following examples shall illustrate preferred embodiments of the present invention but are not intended to limit the scope of the invention.

General Methods

Unless stated otherwise reagents and solvents used in the following examples were commercially available and were used as supplied and without purification.

EXAMPLE 1

2-[(S)-2-((S)-2,5-Dioxo-4-phenyl-imidazolidin-1-yl)-4-methyl-pentanoylamino]-thiazole-4-carboxylic acid methyl ester

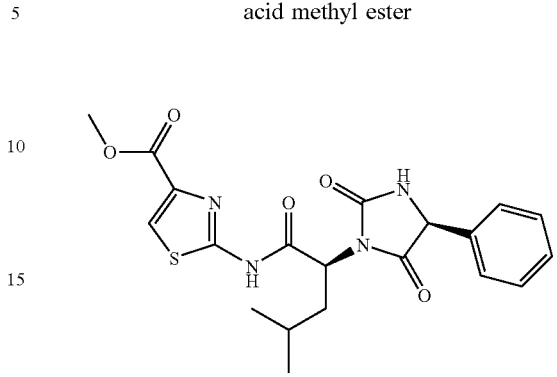

To a suspension of potassium thiocyanate (8.55 g, 88 mmol) in ethyl acetate (100 mL) cooled to 0° C. was added dropwise a solution of 9-fluorenylmethoxycarbonyl chloride (20.7 g, 80 mmol) in ethyl acetate (100 mL) over a period of 15 minutes The resulting suspension was allowed to warm to ambient temperature overnight with stirring. The formed solid was filtered off and the filtrate was concentrated in vacuo to afford an orange oil. Without further purification, the oil was dissolved in ethanol (50 mL) and treated by dropwise addition with a cold solution of ammonia in ethanol (7N, 91 mL, 637 mmol). A precipitate formed upon addition of the ammonia solution. The suspension was stirred vigorously at 0° C. for 15 minute and then the solids were filtered off, washed with cold ethanol (3×20 mL) and dried to afford N-Fmoc-thiourea (16.8 g, 70%) as an off-white solid.

EL-HRMS: Obs. Mass, 298.0770. Calcd. Mass, 298.0776 (M$^+$).

A solution of N-Fmoc-thiourea (5.96 g, 20 mmol) in dioxane (40 mL) was treated with bromopyruvic acid (3.34 g, 20 mmol). The reaction mixture was refluxed for 1 hour then the precipitated solids were recovered by filtration and washed with diethyl ether (3×20 mL) to afford N-Fmoc-2-aminothiazole-4-carboxylic acid (7.1 g, 97%) as a white solid.

EL-HRMS: Obs. Mass, 366.0679. Calcd. Mass, 366.0674 (M$^+$).

A mixture of N-Fmoc-2-aminothiazole-4-carboxylic acid (6.0 g, 16.5 mmol), 2,6-dichlorobenzoyl chloride (7.9 mL, 55 mmol) in N-methylpyrrolidinone (50 mL) was added into a fritted polypropylene column charged with Wang Resin HL (hydroxymethylphenoxy bonded to a polystyrene matrix such as disclosed by Wang et al., *J. Org. Chem.* 1976, 41, 3258 and Rich et al., *J. Am. Chem. Soc.* 1975, 97, 1,575) (Midwest Bio-Tech,10 g, 11 mmol). After the suspension was shaken for 5 minutes, pyridine (6.2 mL, 77 mmol) was added slowly and the resulting dark mixture was shaken overnight at ambient temperature. The mixture was then filtered and the resin was washed with N,N-dimethylformamide (3×100 mL), methanol (3×100 mL), dichloromethane (3×100 mL) and dried in vacuo.

To the resin product of the previous step (110 mg, 0.1 mmol) was added 20% piperidine in N,N-dimethylformamide (2 mL). The reaction mixture was shaken at ambient temperature for 30 minutes. The mixture was filtered and the resin was washed with N,N-dimethylformamide (3×5 mL), methanol (3×5 mL), dichloromethane (3×5 mL). The resin was then suspended in N-methylpyrrolidinone (2 mL) and (S)-N-Fmoc-leucine (106 mg, 0.3 mmol), diisopropylcarbodiimide (47 μL, 0.3 mmol) and 1-hydroxybenzotriazole (41 mg, 0.3 mmol) were added. The resulting mixture was shaken at ambient temperature overnight and filtered. The resin was washed with N,N-dimethylformamide (3×10 mL), methanol (3×10 mL), dichloromethane (3×10 mL) and dried in vacuo.

To the resin product of the previous step (0.1 mmol) was added 20% piperidine in N,N-dimethylformamide (2 mL) and the reaction mixture was shaken at ambient temperature for 30 minutes. The mixture was filtered and the resin was washed with N,N-dimethylformamide (3×5 mL), methanol (3×5 mL) and dichloromethane (3×5 mL). The resin was then suspended in N-methylpyrrolidinone (2 mL) (S)-N-Fmoc-phenylglycine (112 mg, 0.3 mmol), diisopropylcarbodiimide (47 μL, 0.3 mmol) and 1-hydroxybenzotriazole (41 mg, 0.3 mmol) were added. The resulting mixture was shaken at ambient temperature overnight and filtered. The resin was washed with N,N-dimethylformamide (3×10 mL), methanol (3×10 mL), dichloromethane (3×10 mL) and dried in vacuo.

To the product of the previous step (0.1 mmol) was added 20% piperidine in N,N-dimethylformamide (2 mL) and the reaction mixture was shaken at ambient temperature for 30 minutes. The mixture was filtered and the resin was washed with N,N-dimethylformamide (3×10 mL), methanol (3×10 mL) and dichloromethane (3×10 mL). The resin was then suspended in dichloromethane (2 mL) and treated with diisopropylethylamine (52 μL, 0.3 mmol). The reaction mixture was then cooled to 0° C. and diphosgene (36 μL, 0.3 mmol) was added dropwise. The resulting mixture was allowed to warm to the ambient temperature and was stirred for 3 hours. The mixture was filtered and the resin was washed with dichloromethane (3×10 mL) and dried in vacuo. The resin was then suspended in eoluene (2 mL) and the stirred reaction mixture was heated at 70° C. for 4 hours. The cooled resin mixture was filtered and the resin was washed with dichloromethane (3×10 mL). Cleavage from the support was performed by treatment with 50% trifluoroacetic acid in dichloromethane (3 mL) for 1 hour. Concentration of the filtrate gave a brown solid.

Without further purification, the solid from step (7) was dissolved in methanol (1 mL) and then treated with 1-(3-dimethylaminopropyl)-3-ethylcarbodiimide (29 mg, 0.15 mmol). The mixture was stirred at ambient temperature overnight and then was concentrated in vacuo. The resulting oil was dissolved in 99:1 dichloromethane/methanol (3×5 mL) and filtered through a silica gel plug. The filtrate was concentrated in vacuo to afford 2-[(S)-2-((S)-2,5-dioxo-4-phenyl-imidazolidin-1-yl)-4-methyl-pentanoylamino]-thiazole-4-carboxylic acid methyl ester (9 mg) as a white foam.

Molecular ion was detected as 430; the expected molecular weight is 430.1311.

EXAMPLE 2

In a Similar Manner as Described in Example 1, the Following Compounds were Prepared 2-[(S)-3-Cyclohexyl-2-((S)-2,5-dioxo-4-phenyl-imidazolidin-1-yl)-propionylamino]-thiazole-4-carboxylic acid methyl ester

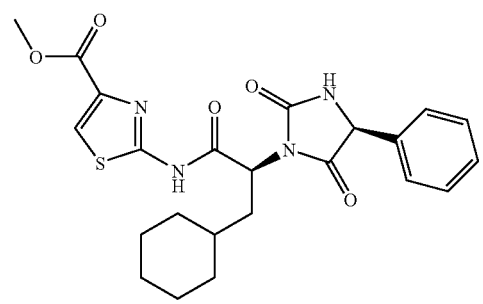

The compound was prepared as described in example 1, except (S)—N-Fmoc-cyclohexylalanine was used in place of (S)—N-Fmoc-leucine in step (4) of example 1.

Molecular ion was detected as 470; the expected molecular weight is 470.1624.

2-[(S)-2-((S)-2,5-Dioxo-4-phenyl-imidazolidin-1-yl)-hexanoylamino]-thiazole-4-carboxylic acid methyl ester

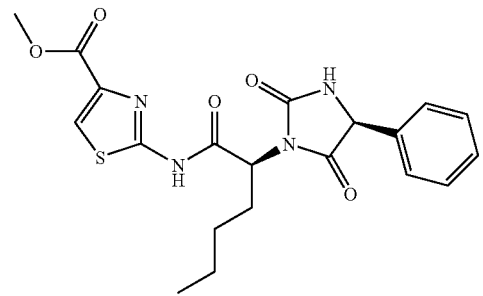

The compound was prepared as described in example 1, except (S)—N-Fmoc-norleucine was used in place of (S)—N-Fmoc-leucine in step (4) of example 1. Molecular ion was detected as 430; the expected molecular weight is 430.1311.

2-[(S)-2-((S)-2,5-Dioxo-4-phenyl-imidazolidin-1-yl)-2-phenyl-acetylamino]-thiazole-4-carboxylic acid methyl ester

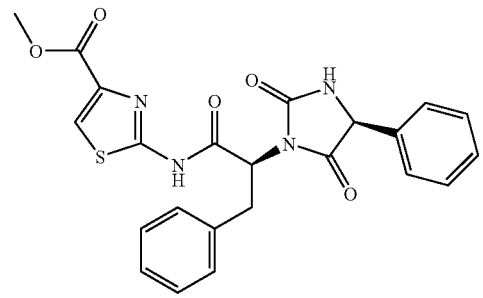

The compound was prepared as described in example 1, except (S)—N-Fmoc-phenylglycine was used in place of (S)—N-Fmoc-leucine in step (4) of example 1.

Molecular ion was detected as 450; the expected molecular weight is 450.0998.

2-[(R)-2-((S)-2,5-Dioxo-4-phenyl-imidazolidin-1-yl)-3-(4-hydroxy-phenyl)-propionylamino]-thiazole-4-carboxylic acid methyl ester

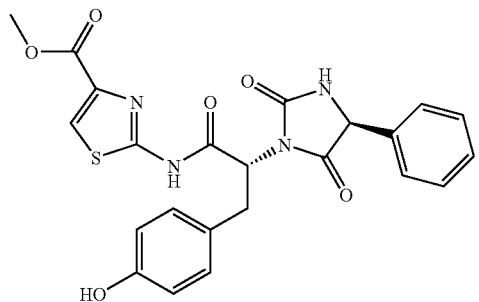

The compound was prepared as described in example 1, except (R)—N-Fmoc-tyrosine was used in place of (S)—N-Fmoc-leucine in step (4) of example 1. Molecular ion was detected as 480; the expected molecular weight is 480.1104.

2-[(S)-2-((S)-2,5-Dioxo-4-phenyl-imidazolidin-1-yl)-4-methylsulfanyl-butyrylamino]-thiazole-4-carboxylic acid methyl ester

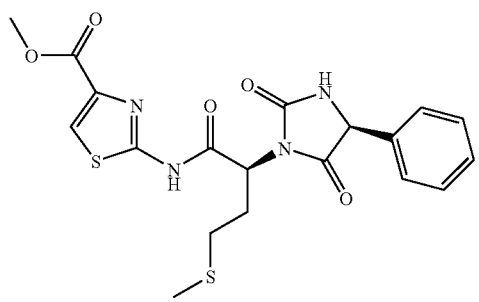

The compound was prepared as described in example 1, except (S)—N-Fmoc-methionine was used in place of (S)—N-Fmoc-leucine in step (4) of example 1. Molecular ion was detected as 448; the expected molecular weight is 448.0875.

2-[(S)-2-((S)-2,5-Dioxo-4-phenyl-imidazolidin-1-yl)-3-thiophen-2-yl-propionylamino]-thiazole-4-carboxylic acid methyl ester

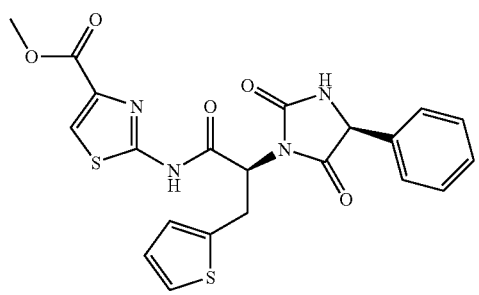

The compound was prepared as described in example 1, except (S)—N-Fmoc-2-thienylalanine was used in place of (S)—N-Fmoc-leucine in step (4) of example 1.

Molecular ion was detected as 470; the expected molecular weight is 470.0719.

2-[(S)-2-((S)-2,5-Dioxo-4-phenyl-imidazolidin-1-yl)-4-phenyl-butyrylamino]-thiazole-4-carboxylic acid methyl ester

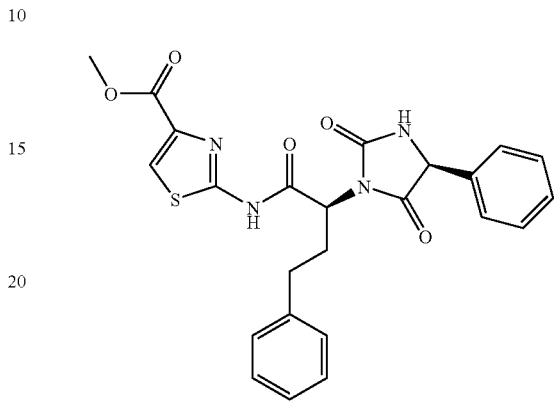

The compound was prepared as described in example 1, except (S)—N-Fmoc-homophenylalanine was used in place of (S)—N-Fmoc-leucine in step (4) of example 1.

Molecular ion was detected as 478; the expected molecular weight is 478.1311.

2-[(R)-2-((S)-2,5-Dioxo-4-phenyl-imidazolidin-1-yl)-pentanoylamino]-thiazole-4-carboxylic acid methyl ester

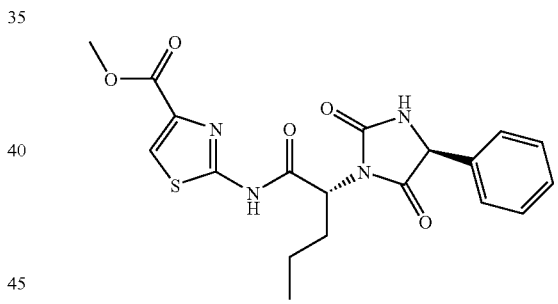

The compound was prepared as described in example 1, except (R)—N-Fmoc-norvaline was used in place of (S)—N-Fmoc-leucine in step (4) of example 1. Molecular ion was detected as 416; the expected molecular weight is 416.1154.

2-[(R)-2-((S)-2,5-Dioxo-4-phenyl-imidazolidin-1-yl)-4-methyl-pentanoylamino]-thiazole-4-carboxylic acid methyl ester

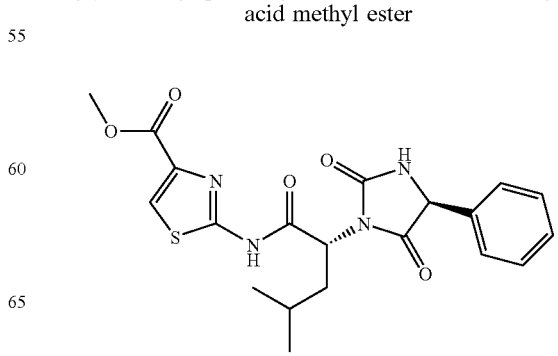

The compound was prepared as described in example 1, except (R)—N-Fmoc-leucine was used in place of (S)—N-Fmoc-leucine in step (4) of example 1. Molecular ion was detected as 430; the expected molecular weight is 430.1311.

2-[(S)-2-((S)-2,5-Dioxo-4-phenyl-imidazolidin-1-yl)-3-phenyl-propionylamino]-thiazole-4-carboxylic acid methyl ester

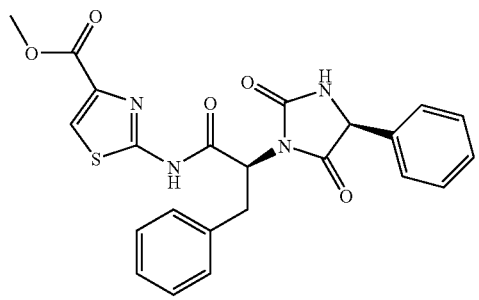

The compound was prepared as described in example 1, except (S)—N-Fmoc-phenylalanine was used in place of (S)—N-Fmoc-leucine in step (4) of example 1.
Molecular ion was detected as 464; the expected molecular weight is 464.1154.

2-[(S)-2-((R)-2,5-Dioxo-4-phenyl-imidazolidin-1-yl)-4-methyl-pentanoylamino]-thiazole-4-carboxylic acid methyl ester

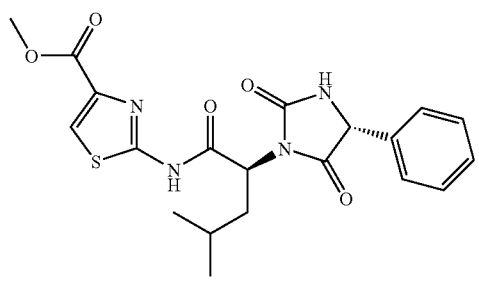

The compound was prepared as described in example 1, except (R)—N-Fmoc-phenylglycine was used in place of (S)—N-Fmoc-phenyl-glycine in step (5) of example 1.
Molecular ion was detected as 430; the expected molecular weight is 430.1311.

2-[(S)-2-((S)-2,5-Dioxo-4-phenyl-imidazolidin-1-yl)-3-naphthalen-2-yl-propionylamino]-thiazole-4-carboxylic acid methyl ester

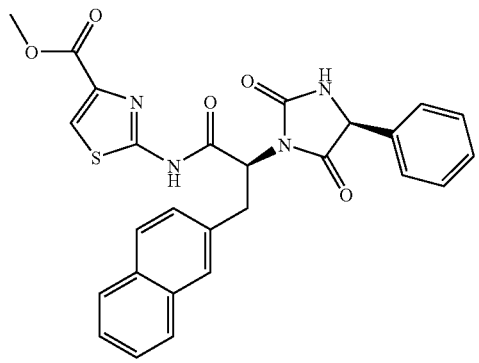

The compound was prepared as described in example 1, except (S)—N-Fmoc-2-naphthylalanine was used in place of (S)—N-Fmoc-leucine in step (4) of example 1.

Molecular ion was detected as 514; the expected molecular weight is 514.1311.

2-[(S)-3-Biphenyl-4-yl-2-((S)-2,5-dioxo-4-phenyl-imidazolidin-1-yl)-propionylamino]-thiazole-4-carboxylic acid methyl ester

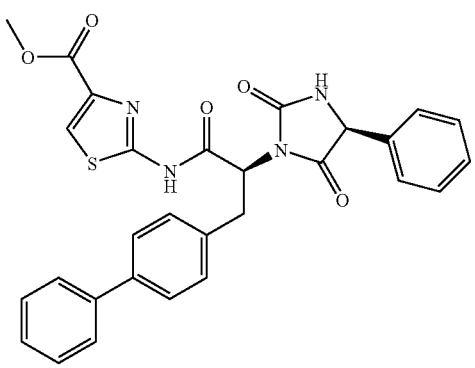

The compound was prepared as described in example 1, except (S)—N-Fmoc-4-biphenylalanine was used in place of (S)—N-Fmoc-leucine in step (4) of example 1.

Molecular ion was detected as 540; the expected molecular weight is 540.1467.

2-[(S)-2-(2,5-Dioxo-4-(2-methyl-phenyl)-imidazolidin-1-yl)-4-methyl-pentanoylamino]-thiazole-4-carboxylic acid methyl ester

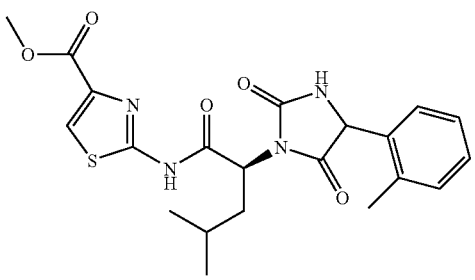

The compound was prepared as described in example 1, except N-Fmoc-2-methylphenylglycine was used in place of (S)—N-Fmoc-phenylglycine in step (5) of example 1.

N-Fmoc-2-methylphenylglycine was prepared according to the general procedure of K. Mai et al., *Tetrahedron Lett.* 1984, 25(41), 4583 with specific details as described below:

To a stirred mixture of 2-methylbenzaldehyde (3.6 g, 30 mmol) and trimethylsilyl cyanide (Aldrich, 95% purity) (5.0 mL, 3.75 g, 38 mmol) was added a catalytic amount of zinc iodide. An exothermic reaction ensued and the reaction mixture left to stir at ambient temperature for 15 minutes. The reaction mixture was then diluted with saturated methanolic ammonia solution (30 mL) and the mixture heated to 40° C. for 2 hours in a flask attached to a water condenser topped with a dry ice/acetone condenser. The reaction mixture was concentrated in vacuo, the residue dissolved in ether, dried (magnesium sulfate) and filtered. The ethereal solution was cooled to 0° C. and saturated with hydrogen chloride gas. After stirring for 20 minutes the pale yellow precipitate of amino-o-tolyl-acetonitrile hydrochloride was collected by filtration and washed with ether (2.97 g). A second crop was obtained by concentrating the filtrate to half its original volume, reacidifying with hydrogen chloride gas and removing the fresh precipitate by filtration (1.75 g). The crude amino-o-tolyl-acetonitrile hydrochloride was heated to reflux in 6M aqueous hydrochloric acid (55 mL) for 10 hours before cooling to ambient temperature and concentrating in vacuo. The residue was triturated with ether/2-propanol to give crude amino-o-tolyl-acetic acid hydrochloride as a white solid which was dried in vacuo (2.5 g, 41%). LRMS: Obs. Mass, 166.0. Calcd. Mass, 166.1 (M+H).

To a solution of crude amino-o-tolyl-acetic acid hydrochloride (2.5 g, 12.4 mmol) in 9% w/v aqueous sodium carbonate solution (25 mL, 21 mmol) was added a solution of Fmoc-O-succinimide (2.7 g, 8.0 mmol) in p-dioxane (55 mL) at 0° C. After 10 minutes te reaction mixture was warmed to ambient temperature and allowed to stir for 24 hours. Additional Fmoc-O-succinimide (0.67 g, 2.0 mmol) in p-dioxane (15 mL) was added and stirring at ambient temperature continued for an additional 24 hours. The reaction mixture was then concentrated in vacuo to remove p-dioxane and the aqueous residue was extracted with ethyl acetate (3×10 mL). The aqueous layer was adjusted to pH=2 with 6M aqueous hydrochloric acid and then extracted with ethyl acetate (2×20 mL), the combined organic extracts dried over magnesium sulfate and concentrated in vacuo. The crude material was purified by chromatography using silica eluted with 99:1 ethyl acetate/acetic acid to give N-Fmoc-2-methylphenylglycine as a colorless solid (2.09 g, 44%). HRMS: Obs. Mass, 410.1367. Calcd. Mass, 410.1363 (M+Na).

Molecular ion was detected as 444; the expected molecular weight is 444.1467.

2-[(S)-2-(4-Furan-2-yl-2,5-dioxo-imidazolidin-1-yl)-3-phenyl-propionylamino]-thiazole-4-carboxylic acid methyl ester

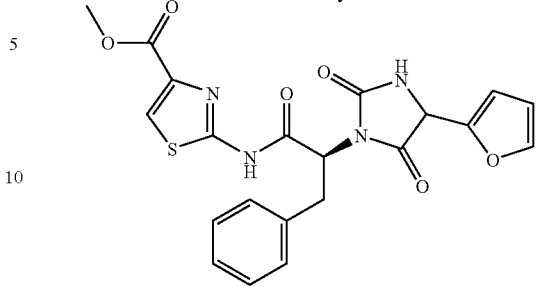

The compound was prepared as described in example 1, except (S)—N-Fmoc-phenylalanine was used in place of (S)—N-Fmoc-leucine in step (4) and N-Fmoc-2-furanylglycine was used in place of (S)—N-Fmoc-phenylglycine in step (5) of example 1.

Molecular ion was detected as 454; the expected molecular weight is 454.0947.

2-[(S)-2-(4-Naphthalen-2-yl-2,5-dioxo-imidazolidin--yl)-3-phenyl-propionylamino]-thiazole-4-carboxylic acid methyl

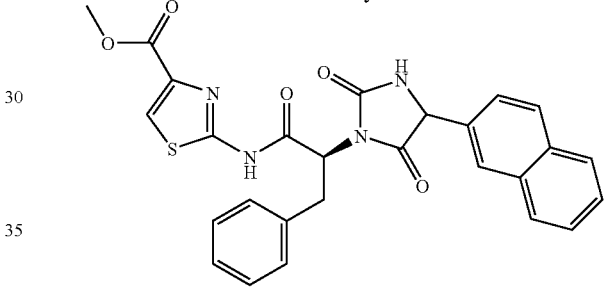

The compound was prepared as described in example 1, except (S)—N-Fmoc-phenylalanine was used in place of (S)—N-Fmoc-leucine in step (4) and N-Fmoc-2-naphthylglycine was used in place of (S)—N-Fmoc-phenylglycine in step (5) of example 1.

Molecular ion was detected as 514; the expected molecular weight is 514.1311.

2-{(S)-2-[4-(4-Hydroxy-phenyl)-2,5-dioxo-imidazolidin-1-yl]-3-phenyl-propionylamino}-thiazole-4-carboxylic acid methyl ester

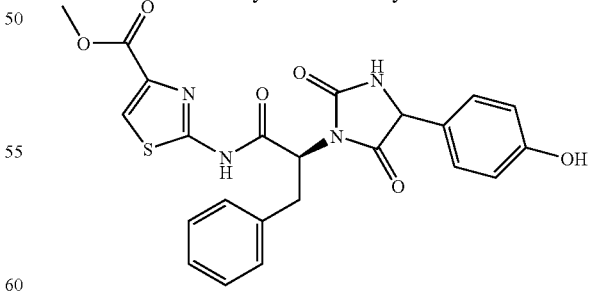

The compound was prepared as described in example 1, except (S)—N-Fmoc-phenylalanine was used in place of (S)—N-Fmoc-leucine in step (4) and N-Fmoc-4-hydroxyphenylglycine was used in place of (S)—N-Fmoc-phenylglycine in step (5) of example 1.

Molecular ion was detected as 480; the expected molecular weight is 480.1104.

2-{(S)-2-[4-(3-Hydroxy-phenyl)-2,5-dioxo-imidazolidin-1-yl]-3-phenyl-propionylamino}-thiazole-4-carboxylic acid methyl ester

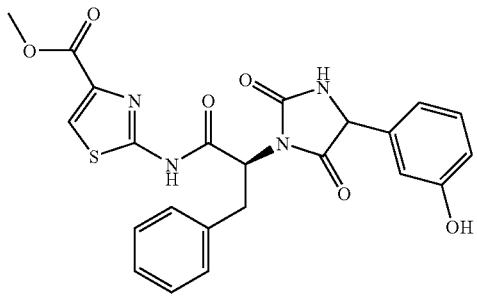

The compound was prepared as described in example 1, except (S)—N-Fmoc-phenylalanine was used in place of (S)—N-Fmoc-leucine in step (4) and N-Fmoc-3-hydroxyphenylglycine was used in place of (S)—N-Fmoc-phenylglycine in step (5) of example 1. N-Fmoc-3-hydroxyphenylglycine was prepared in a manner similar to that described for the preparation of N-Fmoc-2-methylphenylglycine used in example 2(n) except that 3-hydroxybenzaldehyde was substituted for 2-methylbenzaldehyde.

Molecular ion was detected as 480; the expected molecular weight is 480.1104.

2-{(S)-2-[2,5-Dioxo-4-(4-trifluoromethyl-phenyl)-imidazolidin-1-yl]-3-phenyl-propionylamino}-thiazole-4-carboxylic acid methyl ester

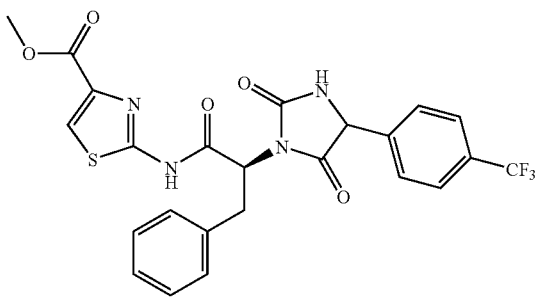

The compound was prepared as described in example 1, except (S)—N-Fmoc-phenylalanine was used in place of (S)—N-Fmoc-leucine in step (4) and N-Fmoc-4-trifluoromethylphenylglycine was used in place of (S)—N-Fmoc-phenylglycine in step (5) of example 1. N-Fmoc-4-trifluoromethylphenylglycine was prepared in a manner similar to that described for the preparation of N-Fmoc-2-methylphenylglycine used in example 2(n) except that 4-trifluoromethylbenzaldehyde was substituted for 2-methylbenzaldehyde.

Molecular ion was detected as 532; the expected molecular weight is 532.1028.

2-{(S)-2-[4-(2-Chloro-phenyl)-2,5-dioxo-imidazolidin-1-yl]-3-phenyl-propionylamino}-thiazole-4-carboxylic acid methyl ester

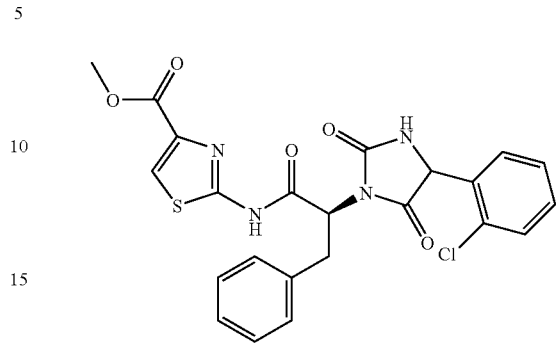

The compound was prepared as described in example 1, except (S)—N-Fmoc-phenylalanine was used in place of (S)—N-Fmoc-leucine in step (4) and N-Fmoc-2-chlorophenylglycine was used in place of (S)—N-Fmoc-phenylglycine in step (5) of example 1. N-Fmoc-2-chlorophenylglycine was prepared in a manner similar to that described for the preparation of N-Fmoc-2-methylphenylglycine used in example 2(n) except that 2-chlorobenzaldehyde was substituted for 2-methylbenzaldehyde.

Molecular ion was detected as 498; the expected molecular weight is 498.0765.

2-{(S)-2-[4-(3-Methoxy-phenyl)-2,5-dioxo-imidazolidin-1-yl]-3-phenyl-propionylamino}-thiazole-4-carboxylic acid methyl ester RO4593792-000-001

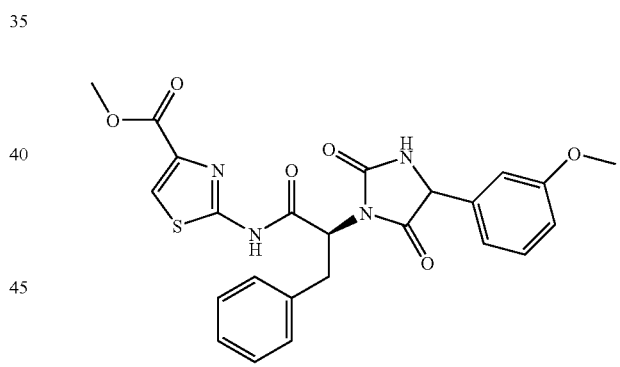

The compound was prepared as described in example 1, except (S)—N-Fmoc-phenylalanine was used in place of (S)—N-Fmoc-leucine in step (4) and N-Fmoc-3-methoxyphenylglycine was used in place of (S)—N-Fmoc-phenylglycine in step (5) of example 1. N-Fmoc-3-methoxyphenylglycine was prepared in a manner similar to that described for the preparation of N-Fmoc-2-methylphenylglycine used in example 2(n) except that 3-methoxybenzaldehyde was substituted for 2-methylbenzaldehyde.

Molecular ion was detected as 494; the expected molecular weight is 494.1260.

2-[(S)-2-(2,5-Dioxo-4-(3-methyl-phenyl)-imidazolidin-1-yl)-3-phenyl-propionylamino]-thiazole-4-carboxylic acid methyl ester The compound was prepared as described in example 1, except (S)—N-Fmoc-phenylalanine was used in place of (S)—N-Fmoc-leucine in step (4) and N-Fmoc-3-methylphenylglycine was used in place of (S)—N-Fmoc-phenylglycine in step (5) of example 1. N-Fmoc-3-methylphenylglycine was prepared in a manner similar to that described for the preparation of N-Fmoc-2-methylphenylglycine used in example 2(n) except that 3-methylbenzaldehyde was substituted for 2-methylbenzaldehyde.

Molecular ion was detected as 478; the expected molecular weight is 478.1311.

2-[(S)-2-(2,5-Dioxo-4-(4-methyl-phenyl)-imidazolidin-1-yl)-4-methyl-pentanoylamino]-thiazole-4-carboxylic acid methyl ester

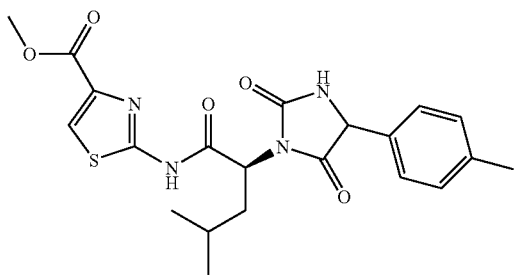

The compound was prepared as described in example 1, except N-Fmoc-4-methylphenylglycine was used in place of (S)—N-Fmoc-phenylglycine in step (5) of example 1. N-Fmoc-4-methylphenylglycine was prepared in a manner similar to that described for the preparation of N-Fmoc-2-methylphenylglycine used in example 2(n) except that 4-methylbenzaldehyde was substituted for 2-methylbenzaldehyde.

Molecular ion was detected as 444; the expected molecular weight is 444.1467.

2-{(S)-2-[4-(4-Isopropyl-phenyl)-2,5-dioxo-imidazolidin-1-yl]-4-methyl-pentanoylamino}-thiazole-4-carboxylic acid methyl ester

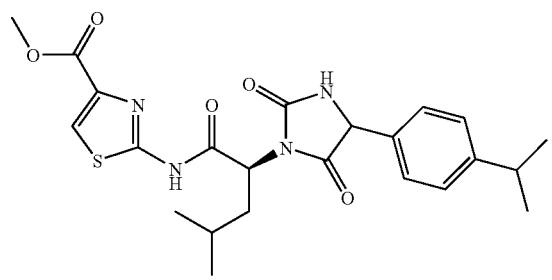

The compound was prepared as described in example 1, except N-Fmoc-4-isopropylphenylglycine was used in place of (S)—N-Fmoc-phenylglycine in step (5) of example 1. N-Fmoc-4-isopropylphenylglycine was prepared in a manner similar to that described for the preparation of N-Fmoc-2-methylphenylglycine used in example 2(n) except that 4-isopropylbenzaldehyde was substituted for 2-methylbenzaldehyde.

Molecular ion was detected as 472; the expected molecular weight is 472.1780.

2-{(S)-2-[4-(4-Chloro-phenyl)-2,5-dioxo-imidazolidin-1-yl]-4-methyl-pentanoylamino}-thiazole-4-carboxylic acid methyl ester

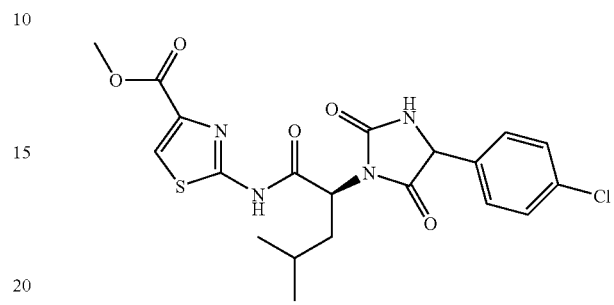

The compound was prepared as described in example 1, except N-Fmoc-4-chlorophenylglycine was used in place of (S)—N-Fmoc-phenylglycine in step (5) of example 1. N-Fmoc-4-chlorophenylglycine was prepared in a manner similar to that described for the preparation of N-Fmoc-2-methylphenylglycine used in example 2(n) except that 4-chlorobenzaldehyde was substituted for 2-methylbenzaldehyde. Molecular ion was detected as 464; the expected molecular weight is 464.0921.

2-{(S)-2-[4-(4-Methoxy-phenyl)-2,5-dioxo-imidazolidin-1-yl]-4-methyl-pentanoylamino}-thiazole-4-carboxylic acid methyl ester

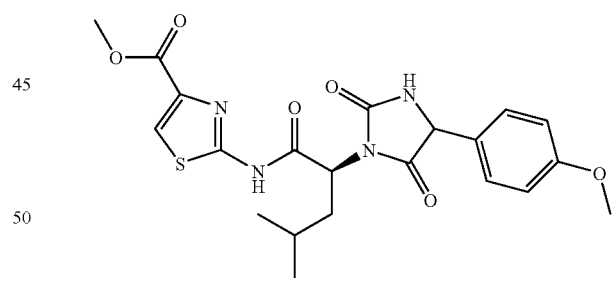

The compound was prepared as described in example 1, except N-Fmoc-4-methoxyphenylglycine was used in place of (S)—N-Fmoc-phenylglycine in step (5) of example 1. N-Fmoc-4-methoxyphenylglycine was prepared in a manner similar to that described for the preparation of N-Fmoc-2-methylphenylglycine used in example 2(n) except that 4-methoxybenzaldehyde was substituted for 2-methylbenzaldehyde.

Molecular ion was detected as 460; the expected molecular weight is 460.1417.

2-[(S)-2-(4-Furan-2-yl-2,5-dioxo-imidazolidin-1-yl)-4-methyl-pentanoylamino]-thiazole-4-carboxylic acid methyl ester

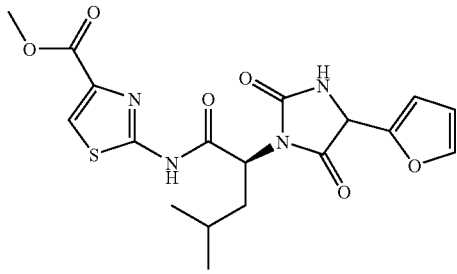

The compound was prepared as described in example 1, except N-Fmoc-2-furanylglycine was used in place of (S)—N-Fmoc-phenylglycine in step (5) of example 1.

Molecular ion was detected as 420; the expected molecular weight is 420.11036.

2-[(S)-4-Methyl-2-(4-naphthalen-2-yl-2,5-dioxo-imidazolidin-1-yl)-pentanoylamino]-thiazole-4-carboxylic acid methyl ester

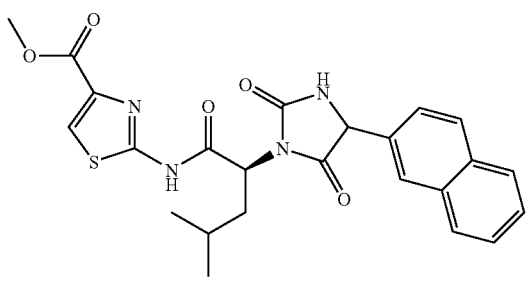

The compound was prepared as described in example 1, except N-Fmoc-2-naphthylglycine was used in place of (S)—N-Fmoc-phenylglycine in step (5) of example 1.

Molecular ion was detected as 480; the expected molecular weight is 480.14674.

2-[(S)-2-(2,5-Dioxo-4-thiophen-3-yl-imidazolidin-1-yl)-4-methyl-pentanoylamino]-thiazole-4-carboxylic acid methyl ester

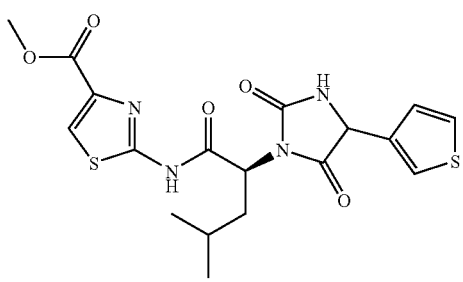

The compound was prepared as described in example 1, except N-Fmoc-3-thienylglycine was used in place of (S)—N-Fmoc-phenylglycine in step (5) of example 1.

Molecular ion was detected as 436; the expected molecular weight is 436.08752.

2-{(S)-2-[4-(4-Fluoro-phenyl)-2,5-dioxo-imidazolidin-1-yl]-4-methyl-pentanoylamino}-thiazole-4-carboxylic acid methyl ester

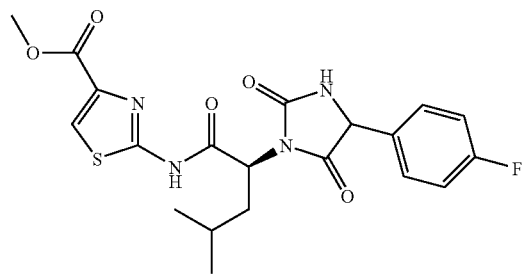

The compound was prepared as described in example 1, except N-Fmoc-4-fluorophenylglycine was used in place of (S)—N-Fmoc-phenylglycine in step (5) of example 1.

Molecular ion was detected as 448; the expected molecular weight is 448.12167.

2-[(S)-2-(4-Benzo[1,3]dioxol-5-yl-2,5-dioxo-imidazolidin-1-yl)-4-methyl-pentanoylamino]-thiazole-4-carboxylic acid methyl ester

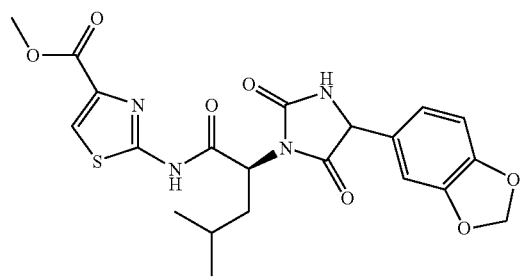

The compound was prepared as described in example 1, except N-Fmoc-3,4-methylenedioxyphenylglycine was used in place of (S)—N-Fmoc-phenylglycine in step (5) of example 1. N-Fmoc-3,4-methylenedioxyphenylglycine was prepared in a manner similar to that described for the preparation of N-Fmoc-2-methylphenylglycine used in example 2(n) except that 3,4-methylenedioxybenzaldehyde was substituted for 2-methylbenzaldehyde. Molecular ion was detected as 474; the expected molecular weight is 474.1209.

2-{(S)-2-[4-(3-Iodo-phenyl)-2,5-dioxo-imidazolidin-1-yl]-4-methyl-pentanoylamino}-thiazole-4-carboxylic acid methyl ester

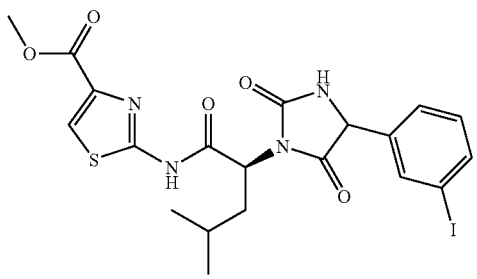

The compound was prepared as described in example 1, except N-Fmoc-3-iodophenylglycine was used in place of (S)—N-Fmoc-phenylglycine in step (5) of example 1. N-Fmoc-3-iodophenylglycine was prepared in a manner similar to that described for the preparation of N-Fmoc-2-methylphenylglycine used in example 2(n) except that 3-iodobenzaldehyde was substituted for 2-methylbenzaldehyde. Molecular ion was detected as 556; the expected molecular weight is 556.0278.

2-{(S)-2-[4-(4-Hydroxy-phenyl)-2,5-dioxo-imidazolidin-1-yl]-4-methyl-pentanoylamino}-thiazole-4-carboxylic acid methyl ester

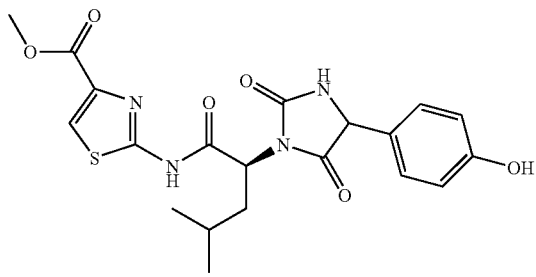

The compound was prepared as described in example 1, except N-Fmoc-4-hydroxyphenylglycine was used in place of (S)—N-Fmoc-phenylglycine in step (5) of example 1.
Molecular ion was detected as 446; the expected molecular weight is 446.1260.

2-{(S)-2-[4-(3-Hydroxy-phenyl)-2,5-dioxo-imidazolidin-1-yl]-4-methyl-pentanoylamino}-thiazole-4-carboxylic acid methyl ester

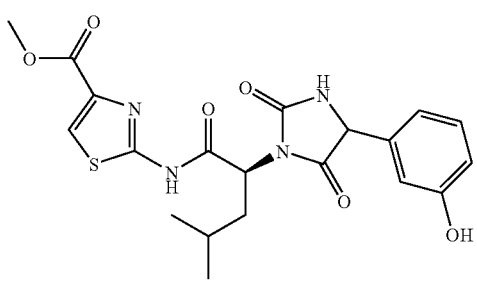

The compound was prepared as described in example 1, except N-Fmoc-3-hydroxyphenylglycine was used in place of (S)—N-Fmoc-phenylglycine in step (5) of example 1. N-Fmoc-3-hydroxyphenylglycine was prepared in a manner similar to that described for the preparation of N-Fmoc-2-methylphenylglycine used in example 2(n) except that 3-hydroxybenzaldehyde was substituted for 2-methylbenzaldehyde.
Molecular ion was detected as 446; the expected molecular weight is 446.1260.

2-{(S)-2-[2,5-Dioxo-4-(3-trifluoromethyl-phenyl)-imidazolidin-1-yl]-4-methyl-pentanoylamino}-thiazole-4-carboxylic acid methyl ester

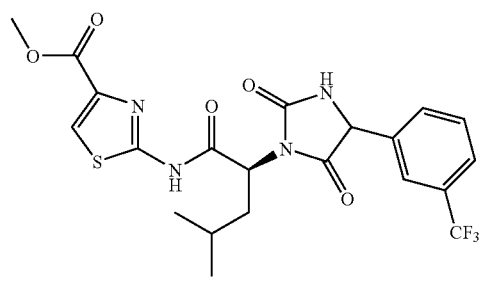

The compound was prepared as described in example 1, except N-Fmoc-3-trifluoromethylphenylglycine was used in place of (S)—N-Fmoc-phenylglycine in step (5) of example 1. N-Fmoc-3-trifluoromethylphenylglycine was prepared in a manner similar to that described for the preparation of N-Fmoc-2-methylphenylglycine used in example 2(n) except that 3-trifluoromethylbenzaldehyde was substituted for 2-methylbenzaldehyde.
Molecular ion was detected as 498; the expected molecular weight is 498.1185.

2-{(S)-2-[4-(2-Methoxy-phenyl)-2,5-dioxo-imidazolidin-1-yl]-4-methyl-pentanoylamino}-thiazole-4-carboxylic acid methyl ester

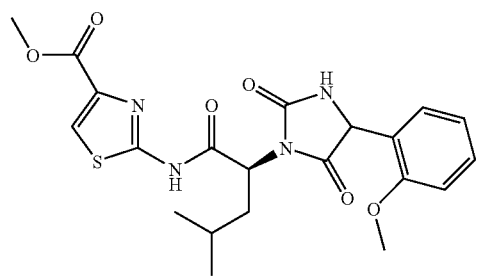

The compound was prepared as described in example 1, except N-Fmoc-2-methoxyphenylglycine was used in place of (S)—N-Fmoc-phenylglycine in step (5) of example 1. N-Fmoc-2-methoxyphenylglycine was prepared in a manner similar to that described for the preparation of N-Fmoc-2-methylphenylglycine used in example 2(n) except that 2-methoxybenzaldehyde was substituted for 2-methylbenzaldehyde.
Molecular ion was detected as 460; the expected molecular weight is 460.1417.

2-{(S)-2-[4-(2-Chloro-phenyl)-2,5-dioxo-imidazoli-
din-1-yl]-4-methyl-pentanoylamino}-thiazole-4-
carboxylic acid methyl ester

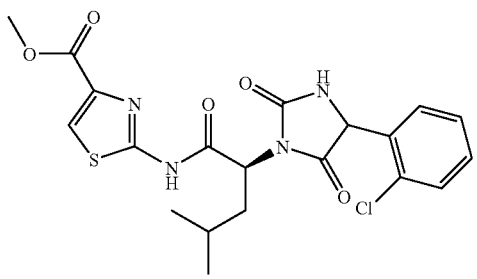

The compound was prepared as described in example 1, except N-Fmoc-2-chlorophenylglycine was used in place of (S)—N-Fmoc-phenylglycine in step (5) of example 1. N-Fmoc-2-chlorophenylglycine was prepared in a manner similar to that described for the preparation of N-Fmoc-2-methylphenylglycine used in example 2(n) except that 2-chlorobenzaldehyde was substituted for 2-methylbenzaldehyde. Molecular ion was detected as 464; the expected molecular weight is 464.0921.

2-{(S)-2-[4-(2-Fluoro-phenyl)-2,5-dioxo-imidazoli-
din-1-yl]-4-methyl-pentanoylamino}-thiazole-4-
carboxylic acid methyl ester

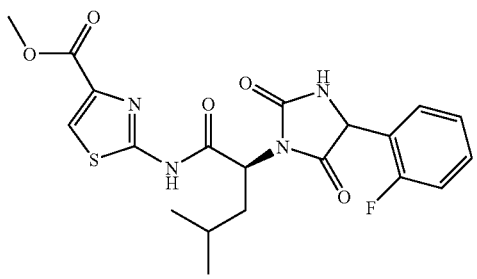

The compound was prepared as described in example 1, except N-Fmoc-2-fluorophenylglycine was used in place of (S)—N-Fmoc-phenylglycine in step (5) of example 1. N-Fmoc-2-fluorophenylglycine was prepared in a manner similar to that described for the preparation of N-Fmoc-2-methylphenylglycine used in example 2(n) except that 2-fluorobenzaldehyde was substituted for 2-methylbenzaldehyde. Molecular ion was detected as 448; the expected molecular weight is 448.1217.

2-{(S)-2-[4-(3-Fluoro-phenyl)-2,5-dioxo-imidazoli-
din-1-yl]-4-methyl-pentanoylamino}-thiazole-4-
carboxylic acid methyl ester

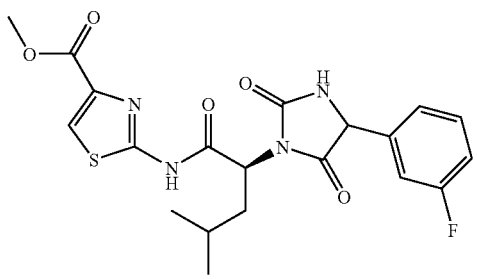

The compound was prepared as described in example 1, except N-Fmoc-3-fluorophenylglycine was used in place of (S)—N-Fmoc-phenylglycine in step (5) of example 1. N-Fmoc-3-fluorophenylglycine was prepared in a manner similar to that described for the preparation of N-Fmoc-2-methylphenylglycine used in example 2(n) except that 3-fluorobenzaldehyde was substituted for 2-methylbenzaldehyde. Molecular ion was detected as 448; the expected molecular weight is 448.1217.

2-{(S)-2-[4-(3-Methoxy-phenyl)-2,5-dioxo-imidazo-
lidin-1-yl]-4-methyl-pentanoylamino}-thiazole-4-
carboxylic acid methyl ester

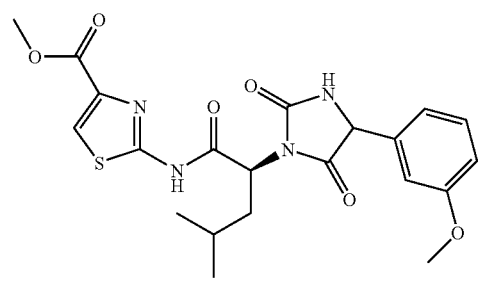

The compound was prepared as described in example 1, except N-Fmoc-3-methoxyphenylglycine was used in place of (S)—N-Fmoc-phenylglycine in step (5) of example 1. N-Fmoc-3-methoxyphenylglycine was prepared in a manner similar to that described for the preparation of N-Fmoc-2-methylphenylglycine used in example 2(n) except that 3-methoxybenzaldehyde was substituted for 2-methylbenzaldehyde.

Molecular ion was detected as 460; the expected molecular weight is 460.1417.

2-[(S)-2-(2,5-Dioxo-4-(3-methyl-phenyl)-imidazoli-
din-1-yl)-4-methyl-pentanoylamino]-thiazole-4-car-
boxylic acid methyl ester

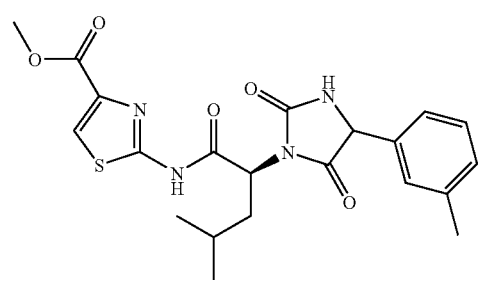

The compound was prepared as described in example 1, except N-Fmoc-3-methylphenylglycine was used in place of (S)—N-Fmoc-phenylglycine in step (5) of example 1. N-Fmoc-3-methylphenylglycine was prepared in a manner similar to that described for the preparation of N-Fmoc-2-methylphenylglycine used in example 2(n) except that 3-methylbenzaldehyde was substituted for 2-methylbenzaldehyde.

Molecular ion was detected as 444; the expected molecular weight is 444.1467.

2-[(S)-2-(2,5-Dioxo-4-(4-methyl-phenyl)-imidazolidin-1-yl)-3-phenyl-propionylamino]-thiazole-4-carboxylic acid methyl ester

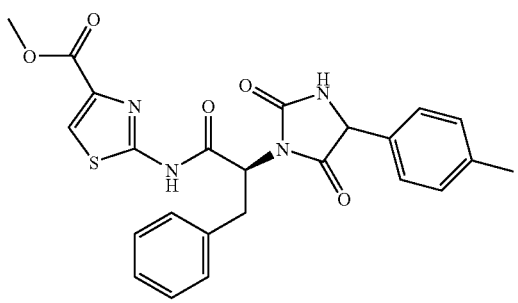

The compound was prepared as described in example 1, except (S)—N-Fmoc-phenylalanine was used in place of (S)—N-Fmoc-leucine in step (4) and N-Fmoc-4-methylphenylglycine was used in place of (S)—N-Fmoc-phenylglycine in step (5) of example 1. N-Fmoc-4-methylphenylglycine was prepared in a manner similar to that described for the preparation of N-Fmoc-2-methylphenylglycine used in example 2(n) except that 4-methylbenzaldehyde was substituted for 2-methylbenzaldehyde.

Molecular ion was detected as 478; the expected molecular weight is 478.1311.

2-[2-(2,5-Dioxo-4-thiophen-3-yl-imidazolidin-1-yl)-3-phenyl-propionylamino]-thiazole-4-carboxylic acid methyl ester

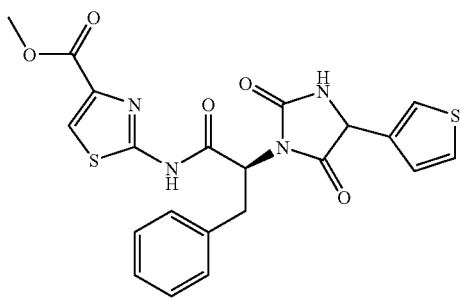

The compound was prepared as described in example 1, except (S)—N-Fmoc-phenylalanine was used in place of (S)—N-Fmoc-leucine in step (4) and N-Fmoc-3-thienylglycine was used in place of (S)—N-Fmoc-phenylglycine in step (5) of example 1. N-Fmoc-3-thienylglycine was prepared in a manner similar to that described for the preparation of N-Fmoc-2-methylphenylglycine used in example 2(n) except that thiophene-3-carbaldehyde was substituted for 2-methylbenzaldehyde.

Molecular ion was detected as 470; the expected molecular weight is 470.0719.

EXAMPLE 3

2{(S)-2-[4-(3-Fluoro-4-methoxy-phenyl)-2,5-dioxo-imidazolidin-1-yl]-3-phenyl-propionylamino}-thiazole-4-carboxylic acid methyl ester

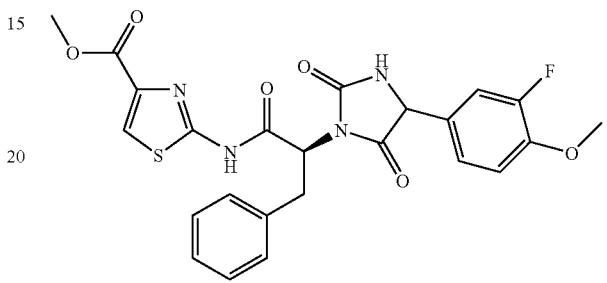

(1) 2-Amino-thiazole-4-carboxylic acid ethyl ester was prepared by a modification to the procedure of Kumar, R.; Rai, D. et al., *Heterocyclic Communications* 2002, 8, 521-530. Thiourea (18.45 g, 240 mmol) was suspended in absolute ethanol (192 mL) and to this was added ethyl bromopyruvate (52 g, 240 mmol) over 5 minutes. The solution was stirred at room temperature overnight and then concentrated in vacuo and taken into water (400 mL) and 6 N aqueous hydrochloric acid (44 mL). The aqueous mixture was washed with ethyl acetate (2×) and back extracted with water (50 mL). The combined aqueous solution was adjusted to pH=10 with sodium hydroxide and extracted with 10% dichloromethane in tetrahydrofuran (3×200 mL). The combined organic extracts were dried over sodium sulfate, concentrated and dried in vacuum. The pale yellow solid was taken into dichloromethane (25 mL) and to the slurry was added hexanes (300 mL). The mixture was vigorously stirred for 15 minutes then filtered on a 9 cm funnel and dried in vacuum to give 2-amino-thiazole-4-carboxylic acid ethyl ester as an off white solid (38 g, 92%).

(2) A mixture of 2-amino-thiazole-4-carboxylic acid ethyl ester (38 g, 221 mmol) in methanol (400 mL) was cooled in an ice bath and to it was added 25% sodium methoxide over 30 minutes. The ice bath was removed after 30 minutes. A few small particles were filtered off and to this yellow solution was added saturated aqueous ammonium chloride and it was concentrated to remove excess methanol. The mixture was adjusted to pH=9.0 with sodium bicarbonate and extracted using 1:1 ether/tetrahydrofuran (3×200 mL). The combined organic extracts were washed with water, dried over sodium sulfate and concentrated to give a pale yellow solid which still contained some solvent. It was taken into hexanes, filtered on a 5.5 cm funnel then dried in vacuo to give 2-amino-thiazole-4-carboxylic acid methyl ester as a pale yellow solid (15.6 g, 45%).

(3) A solution of 2-amino-thiazole-4-carboxylic acid methyl ester (2.4 g, 15.17 mmol), (S)—N-Boc-phenylalanine (4.518 g, 16.69 mmol), 1-hydroxybenzotriazole (2.255 g, 16.69 mmol) and 1,3-diisopropylcarbodiimide (2.127 g, 16.69 mmol) in a mixture of dichloromethane (50 mL) and N,N-dimethylformamide (25 mL) were stirred at ambient temperature for 24 hours. The mixture was diluted with dichloromethane, washed with water, brine and dried with magnesium sulfate. Evaporation of the solvents and chromatography of the residue over silica gel using a gradient between 0 and 25% ethyl acetate in dichloromethane gave 2-((S)-2-tert-butoxycarbonylamino-3-phenyl-propionylamino)-thiazole-4-carboxylic acid methyl ester (4.97 g, 81%).

(4) 2-((S)-2-tert-Butoxycarbonylamino-3-phenyl-propionylamino)-thiazole-4-carboxylic acid methyl ester (2.4 g, 5.919 mmol) was mixed in dichloromethane (25 mL) in an ice-bath. Trifluoroacetic acid (18 mL, 235 mmol) was added and the solution was stirred for 1.5 hours. The reaction mixture was evaporated and the residue was triturated with ether. The suspension was stirred vigorously for 10 minutes and then filtered. The solid was partitioned between aqueous sodium bicarbonate and dichloromethane. The organic layer was separated and the aqueous layer was extracted with dichloromethane. The combined organic extracts were washed with brine and dried over sodium sulfate. Evaporation of the solvents gave 2-((S)-2-amino-3-phenyl-propionylamino)-thiazole-4-carboxylic acid methyl ester as an off white solid (1.58 g, 87%).

(5) To a mixture of 3-fluoro-4-methoxy-benzaldehyde (6.80 g, 41.91 mmol) and trimethylsilyl cyanide (5.47 g, 52.39 mmol) was added a catalytic amount of zinc iodide. An exothermic reaction ensued (reaction mixture internal temperature rose to ≈50° C.) and the reaction mixture was left to stir at room temperature for 20 minutes. To the mixture was added a solution of ammonia in methanol (37.6 mL, 7 N in methanol) and it was warmed on an oil bath at 40° C. in a sealed pressure reaction tube. The mixture was concentrated to give an orange solid. The orange solid and 6N aqueous hydrochloric acid (76 mL) were heated at 110° C. for 3.5 hours. An oily brown residue was removed and the solution was concentrated to dryness. The tan solid was dissolved into water and saturated aqueous sodium bicarbonate was slowly added to adjust the reaction mixture to pH=6.0. The resulting suspension was cooled in an ice bath, filtered over a 5.5 cm funnel and washed with cold water. Amino-(3-fluoro-4-methoxy-phenyl)-acetic acid was obtained as a light tan solid after drying overnight (7.05 g, 85%).

(6) Amino-(3-fluoro-4-methoxy-phenyl)-acetic acid (2.0 g, 10.04 mmol) was dissolved in p-dioxane (24 mL) and 0.5 M aqueous sodium hydroxide solution (22 mL, 11 mmol) added while cooling in an ice bath. To this solution was added di-tert-butyidicarbonate (2.653 g, 12 mmol) and the mixture stirred at 0° C. for 30 minutes then at ambient temperature for 1 hour. The mixture was concentrated to remove dioxane and adjusted to pH=3 with 3 M aqueous potassium hydrogen sulfate solution while cooling in an ice bath. The reaction mixture was extracted with ethyl acetate (3×) and the organics were dried over sodium sulfate, filtered and concentrated to give a brown viscous oil. Crystallization of the oil in ether/hexanes gave tert-butoxycarbonylamino-(3-fluoro-4-methoxy-phenyl)-acetic acid (2.19 g, 73%).

(7) A solution of 2-((S)-2-amino-3-phenyl-propionylamino)-thiazole-4-carboxylic acid methyl ester (0.50 g, 1.637 mmol), tert-butoxycarbonylamino-(3-fluoro-4-methoxy-phenyl)-acetic acid (0.514 g, 1.719 mmol), diisopropylethylamine (1.164 mol, 6.55 mmol) and 1-hydroxybenzotriazole (0.24 g, 1.80 mmol) in N,N-dimethylformamide (10 mL) were stirred in an ice bath for 5 minutes to form a yellow-orange solution. O-Benzotriazol-1-yl-N,N,N',N'-tetramethyluronium hexaflurorophosphate (0.68 g, 1.80 mmol) was added. The mixture was stirred for 5 minutes and the ice bath was removed and the reaction allowed to stir at ambient temperature for 1 hour. The reaction mixture was taken into ethyl acetate and washed with brine and the brine layer back extracted with ethyl acetate. The combined organic extracts were filtered through a layer of sodium sulfate on top of a pad of silica gel contained in a 60 mL capacity vacuum filtration funnel. The pad of sodium sulfate and silica gel was washed through with ethyl acetate and the filtrate concentrated in vacuo to give 2-{(S)-2-[2-tert-butoxycarbonylamino-2-(3-fluoro-4-methoxy-phenyl)-acetylamio]-3-phenyl-propionylaminol-thiazole-4-carboxylic acid methyl ester (0.98 g, 96%).

(8) 2-{(S)-2-[2-tert-Butoxycarbonylamino-2-(3-fluoro-4-methoxy-phenyl)-acetylamino]-3-phenyl-propionylamino}-thiazole-4-carboxylic acid methyl ester (0.98 g, 2.28 mmol) was taken into dry dichloromethane (20 mL) under argon and cooled in an ice bath. To this was added trifluoroacetic acid (10 mL, 130 mmol) and the mixture was stirred at 0° C. for 1 hour. The reaction mixture was then concentrated to dryness. The oil was dissolved in dichloromethane and precipitated with ether and the resulting suspension stirred for 15 minutes. The precipitate was isolated by filtration, washed with ether and dried to give a tan solid. The solid was dissolved in dichloromethane and washed with saturated aqueous sodium bicarbonate. The organic solution was dried over sodium sulfate, filtered, concentrated and dried to give 2-{(S)-2-[2-amino-2-(3-fluoro-4-methoxy-phenyl)-acetylamino]-3-phenyl-propionylamino}-thiazole-4-carboxylic acid methyl ester as a tan foam (0.70 g, 92%).

To a solution of 2-{(S)-2-[2-amino-2-(3-fluoro-4-methoxy-phenyl)-acetylamino]-3-phenyl-propionylamino}-thiazole-4-carboxylic acid methyl ester (0.335 g, 0.688 mmol) and diisopropylethylamine (0.48 mL, 2.75 mmol) in tetrahydrofuran (10 mL) was added to a solution of diphosgene (0.057 mL, 0.48 mmol) in a mixture of toluene (10 mL) and tetrahydrofuran (10 mL) over 10 minute at 0° C. The mixture was stirred at 0° C. for 15 minutes and then diluted with ethyl acetate. The mixture was washed with water, brine and dried over sodium sulfate. Evaporation of the solvents and purification of the residue by chromatography over silica gel eluted with 3:97 methanol/dichloromethane gave 2-{(S)-2-[4-(3-fluoro-4-methoxy-phenyl)-2,5-dioxo-imidazolidin-1-yl]-3-phenyl-propionylamino}-thiazole-4-carboxylic acid methyl ester (0.28 g, 79%).

HRMS: Obs. Mass, 513.1245. Calcd. Mass, 513.1239 (M+H).

EXAMPLE 4
In a Manner Similar as that Described in Example 3, the Following Compounds were Prepared 2-{(S)-2-[4-(2,3-Dihydro-benzo[1,4]dioxin-6-yl)-2,5-dioxo-imidazolidin-1-yl]-3-phenylpropionylamino}-thiazole-4-carboxylic acid methyl ester

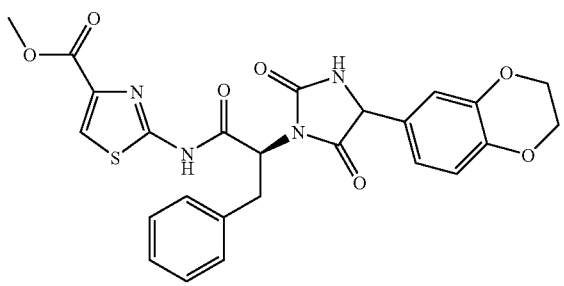

Prepared as described in example 3 except that tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxybenzaldehyde was used in place of 3-fluoro-4-methoxy-benzaldehyde.

HRMS: Obs. Mass, 523.1286. Calcd. Mass, 523.1282 (M+H).

2-{(S)-2-[4-(2,3-Dihydro-benzo[1,4]dioxin-5-yl)-2,5-dioxo-imidazolidin-1-yl]-3-phenyl-propionylamino}-thiazole-4-carboxylic acid methyl ester

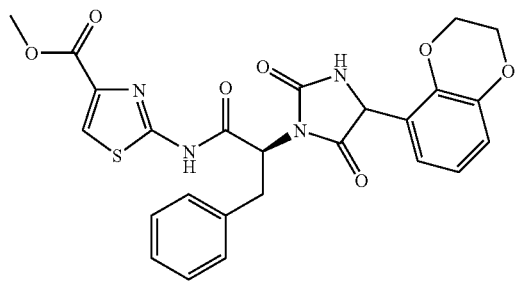

Prepared as described in example 3 except that tert-butoxycarbonylamino-(2,3-dihydro-benzo[1,4]dioxin-5-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-5-yl)-acetic acid was prepared as described in example 3, steps 5 and 6, except that 2,3-ethylenedioxybenzaldehyde was used in place of 3-fluoro-4-methoxy-benzaldehyde.

HRMS: Obs. Mass, 523.1287. Calcd. Mass, 523.1282 (M+H).

2-{(S)-2-[4-(2,3-Dihydro-benzofuran-5-yl)-2,5-dioxo-imidazolidin-1-yl]-3-phenyl-propionylamino}-thiazole-4-carboxylic acid methyl ester

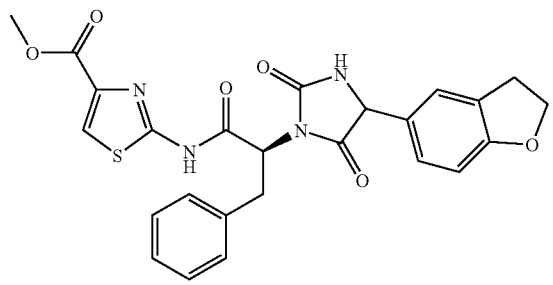

Prepared as described in example 3 except that benzyloxycarbonylamino-(2,3-dihydro-benzofuran-5-yl)-acetic acid was used in place of tert-butoxycarbonylamino-(3-fluoro-4-methoxy-phenyl)-acetic acid in step 7. Benzyloxycarbonylamino-(2,3-dihydro-benzofuran-5-yl)-acetic acid was prepared as described in Bohme, E. H. W. et. al., *J. Med. Chem.* 1980, 23, 405-412.

LRMS: Obs. Mass, 507. Calcd. Mass, 507.1338 (M+H).

2-1(S)-2-[4-(3,4-Dimethoxy-phenyl)-2,5-dioxo-imidazolidin-1-yl]-3-phenyl-propionylamino}-thiazole-4-carboxylic acid methyl ester

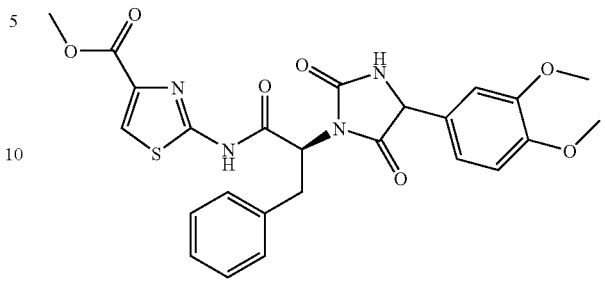

Prepared as described in example 3 except that tert-butoxycarbonylamino-(3,4-dimethoxyphenyl)-acetic acid was used in place of tert-butoxycarbonylamino-(3-fluoro-4-methoxy-phenyl)-acetic acid in step 7. tert-Butoxycarbonylamino-(3,4-dimethoxyphenyl)-acetic acid was prepared as described in example 3, steps 5 and 6, except that 3,4-dimethoxybenzaldehyde was used in place of 3-fluoro-4-methoxy-benzaldehyde.

HRMS: Obs. Mass, 525.1442. Calcd. Mass, 525.1439 (M+H).

2-{(S)-2-[4-(2,3-Difluoro-phenyl)-2,5-dioxo-imidazolidin-1-yl]-3-phenyl-propionylamino}-thiazole-4-carboxylic acid methyl ester

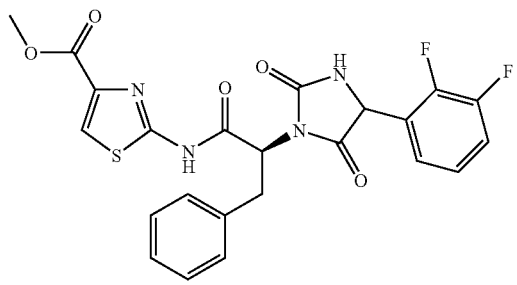

Prepared as described in example 3 except that tert-butoxycarbonylamino-(2,3-difluorophenyl)-acetic acid was used in place of tert-butoxycarbonylamino-(3-fluoro-4-methoxy-phenyl)-acetic acid in step 7. tert-Butoxycarbonylamino-(2,3-difluorophenyl)-acetic acid was prepared as described in example 3, steps 5 and 6, except that 2,3-difluorobenzaldehyde was used in place of 3-fluoro-4-methoxybenzaldehyde.

HRMS: Obs. Mass, 501.1043. Calcd. Mass, 501.1039 (M+H).

2-{(S)-2-[4-(2,4-Difluoro-phenyl)-2,5-dioxo-imidazolidin-1-yl]-3-phenyl-propionylamino}-thiazole-4-carboxylic acid methyl ester

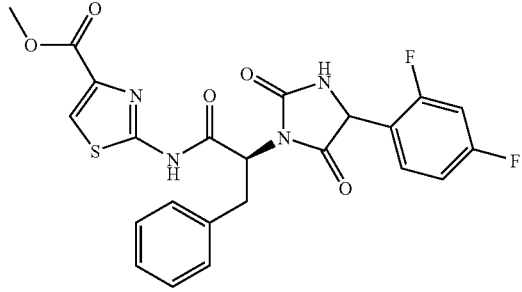

Prepared as described in example 3 except that tert-butoxycarbonylamino-(2,4-difluorophenyl)-acetic acid was used in place of tert-butoxycarbonylamino-(3-fluoro-4-methoxy-phenyl)-acetic acid in step 7. tert-Butoxycarbonylamino-(2,4-difluorophenyl)-acetic acid was prepared as described in example 3, steps 5 and 6, expcept that 2,4-difluorobenzaldehyde was used in place of 3-fluoro-4-methoxybenzaldehyde.

HRMS: Obs. Mass, 501.1045. Calcd. Mass, 501.1039 (M+H).

2-{(S)-2-[4-(3-Chloro-4-methoxy-phenyl)-2,5-dioxo-imidazolidin-1-yl]-3-phenyl-propionylamino}-thiazole-4-carboxylic acid methyl ester

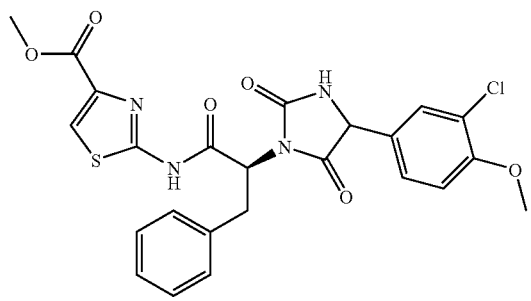

Prepared as described in example 3 except that tert-butoxycarbonylamino-(3-chloro-4-methoxy-phenyl)-acetic acid was used in place of tert-butoxycarbonylamino-(3-fluoro-4-methoxy-phenyl)-acetic acid in step 7. tert-Butoxycarbonylamino-(3-chloro-4-methoxy-phenyl)-acetic acid was prepared as described in example 3, steps 5 and 6, except that 3-chloro-4-methoxy-benzaldehyde was used in place of 3-fluoro-4-methoxy-benzaldehyde.

HRMS: Obs. Mass, 529.0948. Calcd. Mass, 529.0943 (M+H).

2-{(S)-2-[4-(3,5-Difluoro-phenyl)-2,5-dioxo-imidazolidin-1-yl]-3-phenyl-propionylamino}-thiazole-4-carboxylic acid methyl ester

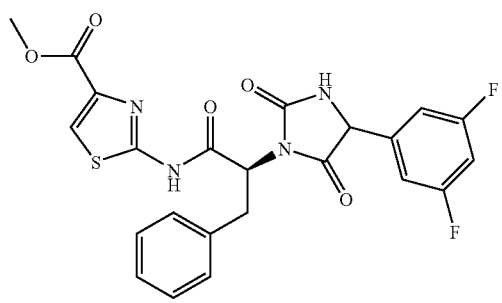

Prepared as described in example 3 except that tert-butoxycarbonylamino-(3,5-difluoro-phenyl)-acetic acid was used in place of tert-butoxycarbonylamino-(3-fluoro-4-methoxy-phenyl)-acetic acid in step 7. tert-Butoxycarbonylamino-(3,5-difluoro-phenyl)-acetic acid was prepared as described in example 3, steps 5 and 6, except that 3,5-difluoro-benzaldehyde was used in place of 3-fluoro-4-methoxybenzaldehyde.

HRMS: Obs. Mass, 501.1042. Calcd. Mass, 501.1039 (M+H).

2-{(S)-2-[4-(2,6-Difluoro-phenyl)-2,5-dioxo-imidazolidin-1-yl]-3-phenyl-propionylamino}-thiazole-4-carboxylic acid methyl ester

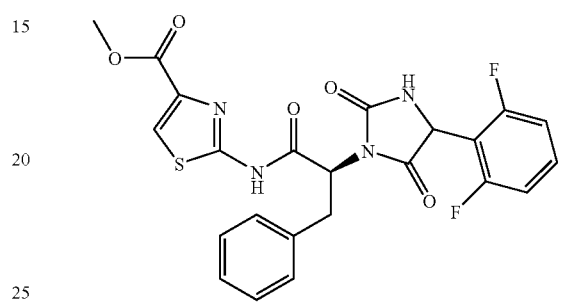

Prepared as described in example 3 except that tert-butoxycarbonylamino-(2,6-difluoro-phenyl)-acetic acid was used in place of tert-butoxycarbonylamino-(3-fluoro-4-methoxy-phenyl)-acetic acid in step 7. tert-Butoxycarbonylamino-(2,6-difluoro-phenyl)-acetic acid was prepared as described in example 3, steps 5 and 6, except that 2,6-difluoro-benzaldehyde was used in place of 3-fluoro-4-methoxybenzaldehyde.

HRMS: Obs. Mass, 510.1043. Calcd. Mass, 510.1039.

2-{(S)-2-[4-(5-Fluoro-2-methoxy-phenyl)-2,5-dioxo-imidazolidin-1-yl]-3-phenyl-propionylamino}-thiazole-4-carboxylic acid methyl ester

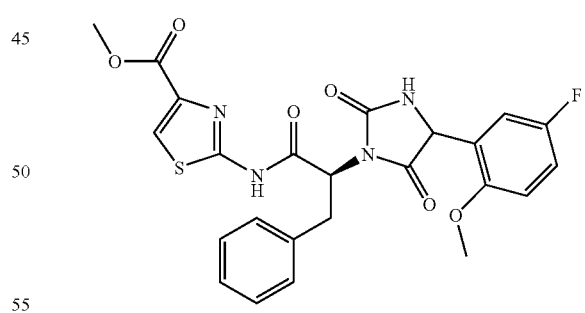

Prepared as described in example 3 except that tert-butoxycarbonylamino-(5-fluoro-2-methoxy-phenyl)-acetic acid was used in place of tert-butoxycarbonylamino-(3-fluoro-4-methoxy-phenyl)-acetic acid in step 7. tert-Butoxycarbonylamino-(5-fluoro-2-methoxy-phenyl)-acetic acid was prepared as described in example 3, steps 5 and 6, except that 5-fluoro-2-methoxybenzaldehyde was used in place of 3-fluoro-4-methoxy-benzaldehyde.

HRMS: Obs. Mass, 513.1243. Calcd. Mass, 513.1239 (M+H).

2-{(S)-2-[4-(2-Fluoro-4-methoxy-phenyl)-2,5-dioxo-imidazolidin-1-yl]-3-phenyl-propionylamino}-thiazole-4-carboxylic acid methyl ester

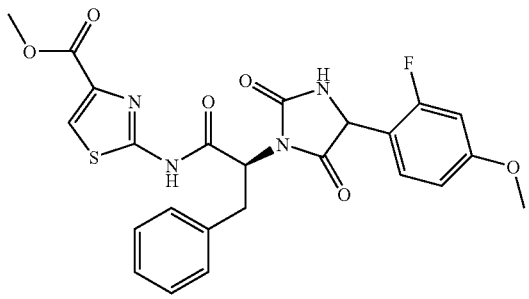

Prepared as described in example 3 except that tert-butoxycarbonylamino-(2-fluoro-4-methoxy-phenyl)-acetic acid was used in place of tert-butoxycarbonylamino-(3-fluoro-4-methoxy-phenyl)-acetic acid in step 7. tert-Butoxycarbonylamino-(2-fluoro-4-methoxy-phenyl)-acetic acid was prepared as described in example 3, steps 5 and 6, except that 2-fluoro-4-methoxybenzaldehyde was used in place of 3-fluoro-4-methoxy-benzaldehyde.

HRMS: Obs. Mass, 513.1244. Calcd. Mass, 513.1239 (M+H).

2-{(S)-2-[4-(4-Dimethylamino-phenyl)-2,5-dioxo-imidazolidin-1-yl]-3-phenyl-propionylamino}-thiazole-4-carboxylic acid methyl ester

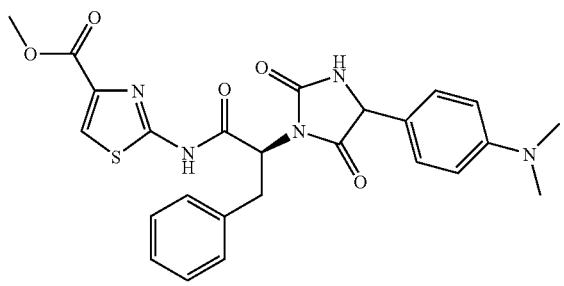

Prepared as described in example 3 except that tert-butoxycarbonylamino-(4-dimethylamino-phenyl)-acetic acid was used in place of tert-butoxycarbonylamino-(3-fluoro-4-methoxy-phenyl)-acetic acid in step 7. tert-Butoxycarbonylamino-(4-dimethylamino-phenyl)-acetic acid was prepared as described in example 3, steps 5 and 6, except that 4-dimethylamino-benzaldehyde was used in place of 3-fluoro-4-methoxy-benzaldehyde.

HRMS: Obs. Mass, 508.1641. Calcd. Mass, 508.1649 (M+H).

2-[2-(4-Benzo[1,3]dioxol-5-yl-2,5-dioxo-imidazolidin-1-yl)-3-(4-cyano-phenyl)-propionylamino]-thiazole-4-carboxylic acid methyl ester

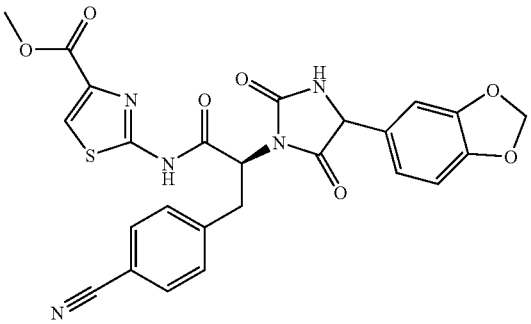

Prepared as described in example 3 except that (S)-2-tert-butoxycarbonylamino-3-(4-cyano-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

LRMS: Obs. Mass, 534.2. Calcd. Mass, 534.1083 (M+H).

2-[(S)-2-(4-Benzo[1,3]dioxol-5-yl-2,5-dioxo-imidazolidin-1-yl)-3-(4-carbamoyl-phenyl)-propionylamino]-thiazole-4-carboxylic acid methyl ester

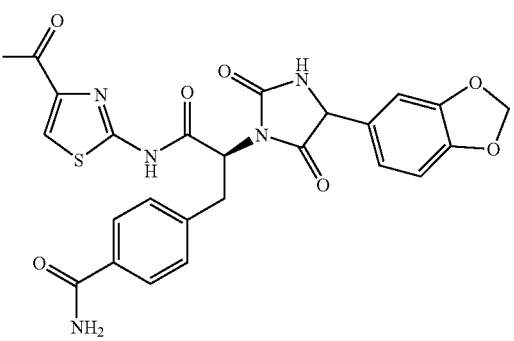

To a solution of 2-[(S)-2-(4-benzo[1,3]dioxol-5-yl-2,5-dioxo-imidazolidin-1-yl)-3-(4-cyano-phenyl)-propionylamino]-thiazole-4-carboxylic acid methyl ester (131 mg, 0.25 mmol) in dimethyl sulfoxide (2.5 mL) was added potassium carbonate (92 mg, 0.67 mmol), water (2.0 mL) followed by hydrogen peroxide (0.17 mL, 1.7 mmol, 30 wt. % in water). The resulting solution was allowed to stir overnight at room temperature. The reaction was neutralized with 10% w/v aqueous citric acid and partitioned between ethyl acetate and water. The organic layer was washed with brine and dried over magnesium sulfate. The crude product was purified by chromatography over silica gel eluted with ethyl acetate to give 2-[(S)-2-(4-benzo[1,3]dioxol-5-yl4-hydroxy-2,5-dioxo-imidazolidin-1-yl)-3-(4-carbamoyl-phenyl)-propionylamino]-thiazole-4-carboxylic acid methyl ester as a white solid (90 mg, 65%).

To a solution of 2-[(S)-2-(4-benzo[1,3]dioxol-5-yl4-hydroxy-2,5-dioxo-imidazolidin-1-yl)-3-(4-carbamoyl-phenyl)-propionylamino]-thiazole-4-carboxylic acid methyl ester (80 mg, 0.14 mmol) in acetic acid (4.0 mL) was added zinc (183 mg, 2.8 mmol). The mixture was heated to 65° C. for 6 hours. The reaction was neutralized with saturated sodium bicarbonate at 0° C. and extracted with ethyl acetate. The organic layer was washed with brine and dried over magnesium sulfate. The solvents were removed and the product was triturated with methanol/diethyl ether, filtered and dried to give 2-[(S)-2-(4-benzo[1,3]dioxol-5-yl-2,5-dioxo-imidazolidin-1-yl)-3-(4-carbamoyl-phenyl)-propionylamino]-thiazole-4-carboxylic acid methyl ester (23 mg, 30%).

HRMS: Obs. Mass, 552.1191. Calcd. Mass, 552.1184.

2-((S)-2-{2,5-Dioxo-4-[4-(2-pyrrolidin-1-yl-ethoxy)-phenyl]-imidazolidin-1-yl}-3-phenyl-propionylamino)-thiazole-4-carboxylic acid methyl ester

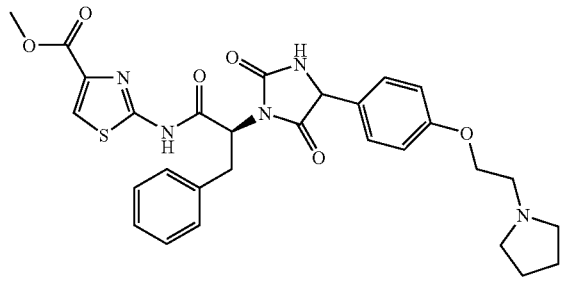

Prepared as described in example 3 except that tert-butoxycarbonylamino-[4-(2-pyrrolidin-1-yl-ethoxy)-phenyl]-acetic acid was used in place of tert-butoxycarbonylamino-(3-fluoro-4-methoxy-phenyl)-acetic acid in step 7. tert-Butoxycarbonylamino-[4-(2-pyrrolidin-1-yl-ethoxy)-phenyl]-acetic acid was prepared as follows.

To an ice chilled solution of (R)—N-tert-butyloxycarbonyl-4-hydroxyphenylglycine (1.0 g, 3.74 mmol) in dry N,N-dimethylformamide was added sodium hydride (60% by wt. suspension in mineral oil) (480 mg, 12.0 mmol) under an atmosphere of nitrogen. The mixture was stirred for 15 minutes at 0° C., then at room temperature for 15 minutes. To the resulting thick slurry was added chloroethylpyrrolidine hydrochloride (765 mg, 4.5 mmol) and potassium iodide (310 mg, 1.87 mmol). The mixture was stirred at room temperature for three days, followed by removal of N,N-dimethylformamide in vacuo. The residue which contained impure tert-butoxycarbonylamino-[4-(2-pyrrolidin-1-yl-ethoxy)-phenyl]-acetic acid was used in subsequent reactions without purification.

HRMS: Obs. Mass, 578.2066. Calcd. Mass, 578.2068 (M+H).

2-((S)-2-{(R)-4-[4-(3-Methoxy-propoxy)-phenyl]-2,5-dioxo-imidazolidin-1-yl}-3-phenyl-propionylamino)-thiazole-4-carboxylic acid methyl ester

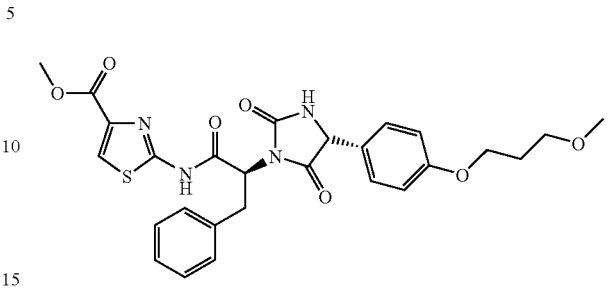

Prepared as described in example 3 except that tert-butoxycarbonylamino-[4-(3-methoxy-propoxy)-phenyl]-acetic acid was used in place of tert-butoxycarbonylamino-(3-fluoro-4-methoxy-phenyl)-acetic acid in step 7. (R)-tert-Butoxycarbonylamino-[4-(3-methoxy-propoxy)-phenyl]-acetic acid was prepared in a manner similar to that described for the preparation of tert-butoxycarbonylamino-[4-(2-pyrrolidin-1-yl-ethoxy)-phenyl]-acetic acid in example 4 (o) except that 1-bromo-3-methoxy-propane was used in place of chloroethylpyrrolidine hydrochloride.

HRMS: Obs. Mass, 553.1754. Calcd. Mass, 553.1752 (M+H).

2-{(S)-2-[4-(1-Methyl-1H-benzoimidazol-5-yl)-2,5-dioxo-imidazolidin-1-yl]-3-phenyl-propionylamino}-thiazole-4-carboxylic acid methyl ester

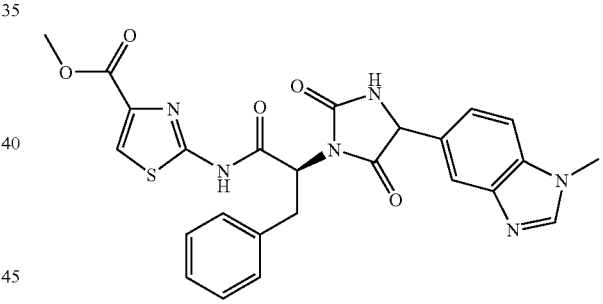

To a solution of 1-methyl-1H-benzoimidazole-5-carbaldehyde (prepared as described in WO0037473) (420 mg, 2.62 mmol) in trimethylsilyl cyanide (2 mL, 15.0 mmol) was added a catalytic amount of zinc iodide. The reaction mixture was stirred at ambient temperature overnight, concentrated under vacuum and the resulting residue dissolved in a 7N solution of ammonia in methanol (10 mL, 70 mmol) in a sealed tube. The mixture was heated for 1.5 hours at 55° C. then cooled to ambient temperature and concentrated under vacuum. The residue was dissolved in 6N aqueous hydrochloric acid (≈10 mL) in a sealed tube. The mixture was stirred at 110° C. for 6 hours then cooled and concentrated under vacuum to afford a solid residue. This solid was dissolved in N,N-dimethylformamide (≈20 mL). Triethylamine (4 mL, 28.7 mmol) and di-tert-butyl dicarbonate (850 mg, 3.93 mmol) were added and the mixture was stirred for 4 hours at ambient temperature. The solvent was then removed, the residue was washed with ether, dried and then dissolved in tetrahydrofuran (55 mL). To this solution was added (S)-2-(2-amino-3-phenylpropinylamino-thiazole-4- carboxylic acid methyl ester (prepared as described in example 3) (800 mg, 2.62 mmol) and the reaction mixture cooled to 0° C. 1-(3-Dimethylaminopropyl)-3-ethylcarbodiimide hydrochloride (500 mg, 2.61 mmol) was added and the reaction mixture was allowed to slowly warm to ambient temperature and then stirred for 48 hours. The reaction mixture was then partitioned between ethyl acetate and water, the ethyl acetate layer was dried over sodium sulfate, filtered and concentrated. Purification of the residue by chromatography over silica gel gradient eluted between 0 and 50% v/v ethyl acetate in dichloromethane and then gradient eluted between 0 to 4% methanol in dichloromethane. Precipitation of the isolated product from a tetrahydrofuran solution with an excess of hexanes afforded 2-{(S)-2-[2-tert-butoxycarbonylamino-2-(1-methyl-1 H-benzoimidazol-5-yl)-acetylamino]-3-phenyl-propionylamino}-thiazole-4-carboxylic acid methyl ester as an amorphous white solid (510 mg, 33%).

HRMS: Obs. Mass, 593.2167. Calcd. Mass, 593.2177 (M+H)

(2) 2-{(S)-2-[2-tert-Butoxycarbonylamino-2-(1-methyl-1 H-benzoimidazol-5-yl)-acetylamino]-3-phenyl-propionylamino)-thiazole-4-carboxylic acid methyl ester (185 mg, 0.193 mmol) was dissolved at 0° C. in a 30% v/v solution of trifluoroacetic acid in dichloromethane (10 mL, 38.9 mmol). The reaction mixture was slowly warmed to room temperature and stirred for approximately 3.5 hours. The reaction mixture was then cooled to 0° C. and neutralized by the addition of solid sodium bicarbonate until there was no further evolution of carbon dioxide. The reaction mixture was then partitioned between dichloromethane and water and the water layer thoroughly extracted with dichloromethane until no products could be detected in the organic extract as judged by absorption of ultraviolet radiation on silica gel thin layer chromatography plates containing a fluorescent indicator which absorbed at 254 nm. The combined organic layers were dried over sodium sulfate, filtered and concentrated. The residue was dissolved in tetrahydrofuran (≈5 mL), diisopropylethyl amine (180 μL, 1.00 mmol) added and the resulting solution was transferred via cannula to a solution of diphosgene (20 μL, 0.18 mmol) in tetrahydrofuran (≈10 mL) at 0° C. After stirring for 10 minutes the reaction mixture was partitioned between ethyl acetate and water, the water layer separated and extracted with ethyl acetate until no products could be detected in the organic extract as judged by absorption of ultraviolet radiation on silica gel thin layer Chromatography plates containing a fluorescent indicator which absorbed at 254 nm. The combined organic extracts were dried over sodium sulfate, filtered and concentrated. The residue was purified by chromatography over silica gel gradient eluted between 0 and 5% v/v methanol in dichloromethane and the isolated product precipitated from a dichloromethane solution with an exess of hexanes to afford 2-{(S)-2-[4-(1-methyl-1H-benzoimidazol-5-yl)-2,5-dioxo-imidazolidin-1-yl]-3-phenyl-propionylamino}-thiazole-4-carboxylic acid methyl ester as an off-white solid (60 mg, 60%).

HRMS: Obs. Mass, 519.1442. Calcd. Mass, 519.1445 (M+H).

2-[(S)-2-(4-Benzo[1,3]dioxol-5-yl-2,5-dioxo-imidazolidin-1-yl)-3-(2-trifluoromethl-phenyl)-propionylamino]-thiazole-4-carboxylic acid methyl ester

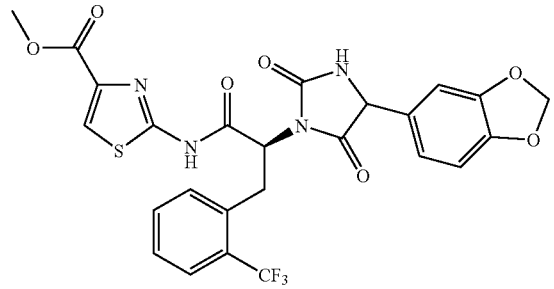

Prepared as described in example 3 except that (S)-2-tert-butoxycarbonylamino-3-(2-trifluoromethyl-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxyphenyl)-acetic acid in step 7. Benzo[1,3]dioxol-5-yl-tert-butoxycarbonylamino-acetic acid was prepared as described in example 3, steps 5 and 6, except that 3,4-methylenedioxybenzaldehyde was used in place of 3-fluoro-4-methoxybenzaldehyde.

HRMS: Obs. Mass, 577.1002. Calcd. Mass, 577.1000 (M+H)

2-[(S)-2-[4-(4-Methylsulfanyl-phenyl)-2,5-dioxo-imidazolidin-1-yl]-3-(2-trifluoromethyl-phenyl)-propionylamino]-thiazole-4-carboxylic acid methyl ester

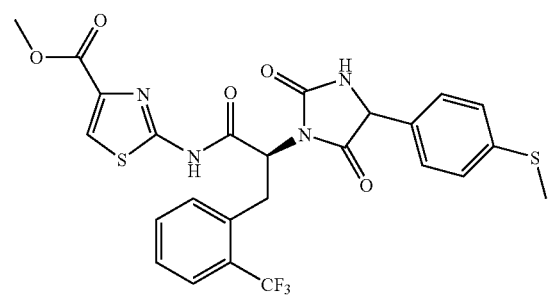

Prepared as described in example 3 except that (S)-2-tert-butoxycarbonylamino-3-(2-trifluoromethyl-phenyl)-propionic acid was used in place of (S)-2-tert-butoxycarbonylamino-3-phenyl-propionic acid in step 3 and tert-butoxycarbonylamino-(4-methylsulfanyl-phenyl)-acetic acid was used in place of tert-butoxycarbonylamino-(3-fluoro-4-methoxy-phenyl)-acetic acid in step 7. tert-Butoxycarbonylamino-(4-methylsulfanyl-phenyl)-acetic acid was prepared as described in example 3, steps 5 and 6, except that 4-methylsulfanyl-benzaldehyde was used in place of 3-fluoro-4-methoxy-benzaldehyde.

HRMS: Obs. Mass, 579.0975. Calcd. Mass, 579.0978 (M+H)

2-[(S)-2-[4-(4-Methanesulfinyl-phenyl)-2,5-dioxo-imidazolidin-1-yl]-3-(2-trifluoromethyl-phenyl)-propionylamino]-thiazole-4-carboxylic acid methyl ester 2-[(S)-2-[4-(2,3-Dihydro-benzo[1,4]dioxin-6-yl)-2,5-dioxo-imidazolidin-1-yl]-3-(1H-indol-3-yl)-propionylamino]-thiazole-4-carboxylic acid methyl ester

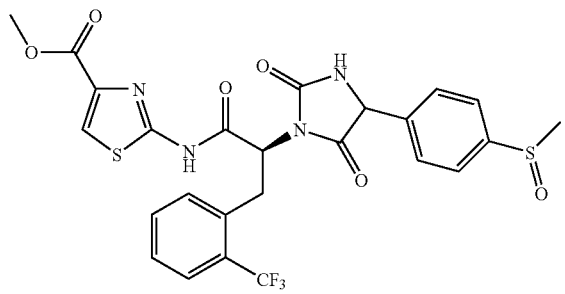

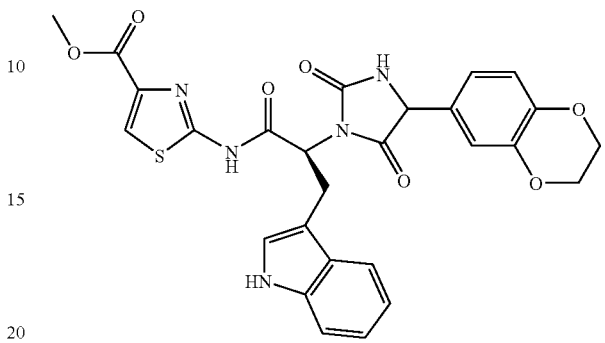

To a solution of 2-[(S)-2-[4-(4-methylsulfanyl-phenyl)-2,5-dioxo-imidazolidin-1-yl]-3-(2-trifluoromethyl-phenyl)-propionylamino]-thiazole-4-carboxylic acid methyl ester (95 mg, 0.16 mmol) in dichloromethane (15 mL) was added 3-chloroperbenzoic acid (75% purity) (45 mg, 0.19 mmol) at 0° C. After stirring for 10 minute the reaction mixture was partitioned between ethyl acetate and saturated aqueous sodium carbonate. The organic layer was dried over sodium sulfate, filtered, concentrated and the residue was purified by chromatography over silica gel eluted with acetone. The isolated material was precipitated from acetone with an excess of hexanes to afford 2-[(S)-2-[4-(4-methanesulfinyl-phenyl)-2,5-dioxo-imidazolidin-1-yl]-3-(2-trifluoromethyl-phenyl)-propionylamino]-thiazole-4-carboxylic acid methyl ester as an amorphous white solid (50 mg, 52%).

HRMS: Obs. Mass, 595.0930. Calcd. Mass, 595.0928 (M+H)

2-[(S)-2-(2,5-Dioxo-4-thiophen-2-yl-imidazolidin-1-yl)-3-phenyl-propionylamino]-thiazole-4-carboxylic acid methyl ester

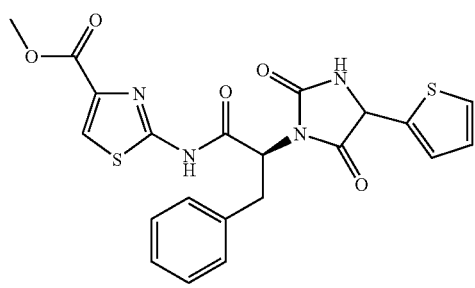

Prepared as described in example 3 except that tert-butoxycarbonylamino-thiophen-2-yl-acetic acid was used in place of tert-butoxycarbonylamino-(3-fluoro-4-methoxy-phenyl)-acetic acid in step 7. tert-Butoxycarbonylamino-thiophen-2-yl-acetic acid was prepared as described in example 3, steps 5 and 6, except that thiophene-2-carbaldehyde was used in place of 3-fluoro-4-methoxy-benzaldehyde.

HRMS: Obs. Mass, 471.0788. Calcd. Mass, 471.0792 (M+H).

(1) 3-[(S)-2-Carboxy-2-(9H-fluoren-9-ylmethoxycarbonylamino)-ethyl]-indole-1-carboxylic acid tert-butyl ester (700 mg, 1.33 mmol) was dissolved in dichloromethane (20 mL). Pyridine (107 µL, 1.33 mmol) was added, the mixture was cooled to −10° C. and cyanuric fluoride (270 mg, 1.99 mmol) was added. The reaction mixture was stirred for 2 hours at −10° C. and then partitioned between dichloromethane and water. The organic layer was dried over sodium sulfate, filtered and concentrated. The residued was immediately dissolved in p-dioxane (≈4 mL). The resulting mixture was treated with 2-aminothiazole-3-carboxymethyl ester (320 mg, 1.99 mmol) and then heated by microwave irradiation in a sealed vessel at 120° C. for 10 minutes After cooling to room temperature, the solvents were evaporated. The crude product was purified by chromatography over silica gel gradient eluted between 0 and 50% ethyl acetate in hexanes. The isolated material was further purified by precipitation from a dichloromethane with excess hexanes to afford 3-[(S)-2-(9H-fluoren-9-ylmethoxycarbonylamino)-2-(4-methoxycarbonyl-thiazol-2-ylcarbamoyl)-ethyl]-indole-1-carboxylic acid tert-butyl ester as a white solid (750 mg, 84%).

HRMS: Obs. Mass, 667.2223. Calcd. Mass, 667.2221 (M+H)

To a solution of 3-[(S)-2-(9H-fluoren-9-ylmethoxycarbonylamino)-2-(4-methoxycarbonyl-thiazol-2-ylcarbamoyl)-ethyl]-indole-1-carboxylic acid tert-butyl ester. (667 mg, 1.00 mmol) in dichloromethane was added piperidine (1 mL, 10.1 mmol). The solution was stirred at room temperature for 3 hours, after which, the volatiles were removed in vacuo. The oily residue was dissolved dichloromethane (10 mL) and excess hexanes were added to give a precipitate, the solvents were removed in vacuo, and the precipitation procedure was repeated twice. The resulting solid was triturated with hexanes then filtered and dried to give the intermediate 3-[2-amino-2-(4-methoxycarbonyl-thiazol-2-yloxycarbonyl)-ethyl]-indole-1-carboxylic acid tert-butyl ester (420 mg, 94%). To a cold solution of 3-[2-amino-2-(4-methoxycarbonyl-thiazol-2-yloxycarbonyl)-ethyl]-indole-1-carboxylic acid tert-butyl ester (242 mg, 0.544 mmol) in dichloromethane (20 mL) was added (2,3-dihydro-benzo[1,4]dioxin-6-yl)-[(9H-fluoren-9-ylmethoxycarbonylamino)]-acetic acid (282 mg, 0.654 mmol) (prepared as described in example 2(n) except that 3,4-ethylenedioxy-benzaldehyde was used in place of 2-methylbenzaldehyde) followed by 1-(3-dimethylaminopropyl)-3-ethylcarbodiimide hydrochloride (125 mg, 0.652 mmol). The reaction mixture was stirred at room temperature overnight, diluted with dichloromethane (50 mL) and then washed sequentially with 0.2M aqueous hydrochloric acid, saturated aqueous sodium bicarbonate, water, brine dried over sodium sulfate and concentrated in vacuo. The residue was purified by chromatography over silica gel gradient eluted between 10% and 20% ethyl acetate in dichloromethane. 2-[(S)-2-[2-(2,3-Dihydro-benzo[1,4]dioxin-6-yl)-2-(9H-fluoren-9-yl-methoxycarbonylamino)-acetylamino]-2-(4-methoxycarbonyl-thiazol-2-ylcarbamoyl)-ethyl]-indole-1-carboxylic acid tert-butyl ester was obtained as an off-white solid (228 mg, 48%).

HRMS: Obs. Mass, 858.2801. Calcd. Mass, 858.2804 (M+H).

To a solution of 2-[(S)-2-[2-(2,3-dihydro-benzo[1,4]dioxin-6-yl)-2-(9H-fluoren-9methoxycarbonylamino)-acetylamino]-2-(4-methoxycarbonyl-thiazol-2-ylcarbamoyl)-ethyl]-indole-1-carboxylic acid tert-butyl ester (147 mg, 0.171 mmol) in dichloromethane (20 mL) was added piperidine (500 µL, 5.0 mmol). The solution was stirred at room temperature for 2 hours, then the volatiles were removed in vacuo. The residue was dissolved dichloromethane (10 mL) and excess hexanes were added to form a precipitate. The solvents were removed in vacuo and the precipitation procedure was repeated twice. The resulting solid was titurated with hexanes to give the intermediate 3-[2-[2-amino-2-(2,3-dihydro-benzo[1,4]dioxin-6-yl)-acetylamino]-2-(4-methoxycarbonyl-thiazol-2-yloxycarbonyl)-ethyl]-indole-1-carboxylic acid tert-butyl ester. To an ice chilled solution of diphosgene (0.021 µL, 0.171 mmol) in dichloromethane (10 mL) was added, dropwise, a solution of the intermediate amine and diisopropylethylamine (0.120 µL, 0.684 mmol) in dichloromethane (10 mL) over 10 minutes. The reaction was quenched by adding crushed ice, diluted with ethyl acetate (75 mL) and washed twice with 0.2M aqueous hydrochloric acid, saturated aqueous sodium bicarbonate, water, brine and dried over sodium sulfate. The mixture was filtered and concentrated to dryness to give 3-[(S)-2-[4-(2,3-dihydro-benzo[1,4]dioxin-6-yl)-2,5-dioxo-imidazolidin-1-yl]-2-(4-methoxycarbonyl-thiazol-2-ylcarbamoyl)-ethyl]-indole-1-carboxylic acid tert-butyl ester (78 mg, 69%).

HRMS: Obs. Mass, 662.1912. Calcd. Mass, 662.1915 (M+H)

To a cold solution of 3-[(S)-2-[4-(2,3-Dihydro-benzo[1,4]dioxin-6-yl)-2,5-dioxo-imidazolidin-1-yl]-2-(4-methoxycarbonyl-thiazol-2-ylcarbamoyl)-ethyl]-indole-1-carboxylic acid tert-butyl ester (78 mg, 0.118 mmol) in dichloromethane (10 mL), was added trifluoroacetic acid (2 mL, 26.0 mmol). The reaction mixture was stirred at room temperature for 1 hour. The volatiles were removed in vacuo and the residue was dissolved in ethyl acetate (100 mL), washed once with cold saturated aqeous sodium bicarbonate, water, brine and dried over sodium sulfate. The solvent was removed and the residue was purified by chromatographed over silica gel gradient eluted between 50% and 75% ethyl acetate in hexanes to afford 2-[(S)-2-[4-(2,3-dihydro-benzo[1,4]dioxin-6-yl)-2,5-dioxo-imidazolidin-1-yl]-3-(1H-indol-3-yl)-propionylamino]-thiazole-4-carboxylic acid methyl ester (37 mg, 55%).

HRMS: Obs. Mass, 562.1389. Calcd. Mass, 562.1391 (M+H)

2-{(S)-2-[4-(2,2-Difluoro-benzo[1,3]dioxol-5-yl)-2,5-dioxo-imidazolidin-1-yl]-3-phenyl-propionylamino}-thiazole-4-carboxylic acid methyl ester

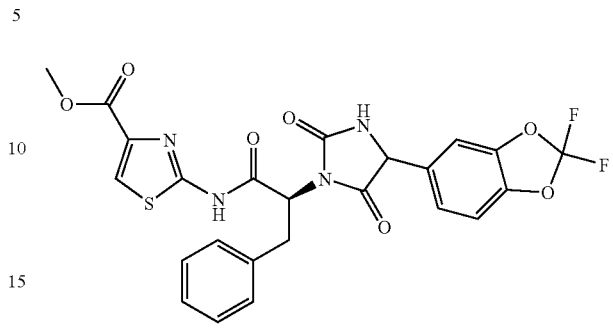

Prepared as described in example 3 except that tert-butoxycarbonylamino-(2,2-difluoro-benzo[1,3]dioxol-5-yl)-acetic acid was used in place of tert-butoxycarbonylamino-(3-fluoro-4-methoxy-phenyl)-acetic acid in step 7. tert-Butoxycarbonylamino-(2,2-difluoro-benzo[1,3]dioxol-5-yl)-acetic acid was prepared as described in example 3, steps 5 and 6, except that 3,4-(difluoromethylenedioxy)-benzaldehyde was used in place of 3-fluoro-4-methoxy-benzaldehyde.

HRMS: Obs. Mass, 545.0940. Calcd. Mass, 545.0937.

2-(S)-2-[4-(3,5-Dimethoxy-phenyl)-2,5-dioxo-imidazolidin-1-yl]-3-phenyl-propionylamino}-thiazole-4-carboxylic acid methyl ester

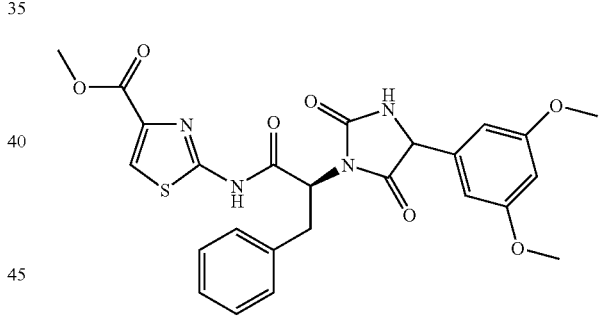

Prepared as described in example 3 except that tert-butoxycarbonylamino-(3,5-dimethoxy-phenyl)-acetic acid was used in place of tert-butoxycarbonylamino-(3-fluoro-4-methoxy-phenyl)-acetic acid in step 7. tert-Butoxycarbonylamino-(3,5-dimethoxy-phenyl)-acetic acid was prepared as described below.

To a mixture of 3,5-dimethoxybenzaldehyde (3.69 g, 22.2 mmol) and trimethylsilyl cyanide (2.2 g, 22.2 mmol) was added a catalytic amount zinc iodide. The reaction mixture was stirred at room temperature for 20 minutes, followed by the addition of a 7 N solution of ammonia in methanol (50 mL, 0.35 mol). The reaction mixture was transferred to a sealed tube and heated at 80° C. for 4 hours. The mixture was concentrated to dryness, and the residue was treated with 1 N hydrogen chloride solution in ether. The precipitate was filtered, dried and collected. The orange solid was dissolved into an 6 N aqueous hydrochloric acid (50 mL). The reaction mixture was heated at 110° C. for 5 hours then concentrated to dryness. The crude hydrochloride salt of amino-(3,5-dimethoxy-phenyl)-acetic acid was obtained as a tan solid which was used in the next step without further purification (5.5 g, 100%).

To a solution of amino-(3,5-dimethoxy-phenyl)-acetic acid hydrochloride salt (1.5 g, 6.05 mmol) in p-dioxane (20 mL) at 0° C. was added a solution of sodium hydroxide (0.58 g, 14.5 mmol) in water (10 mL). To the resulting solution was added di-tert-butyidicarbonate (1.6 g, 7.26 mmol). After stirring at 0° C. for 30 minutes the reaction was warmed to ambient temperature and left to stir for an additional 1 hour. The mixture was concentrated to remove p-dioxane and acidified to pH≈2 with a cold dilute aqueous hydrochloric acid. The mixture was extracted with ethyl acetate (3×). The organic layers were combined, dried over sodium sulfate and concentrated to give tert-butoxycarbonylamino-(3,5-dimethoxy-phenyl)-acetic acid as a yellow gum (1.6 g, 85%).

HRMS: Obs. Mass, 525.1432. Calcd. Mass, 525.1439 (M+H).

2-[(S)-2-(4-Benzo[1,3]dioxol-5-yl-2,5-dioxo-imidazolidin-1-yl)-3-pyridin-3-yl-propionylamino]-thiazole-4-carboxylic acid methyl ester

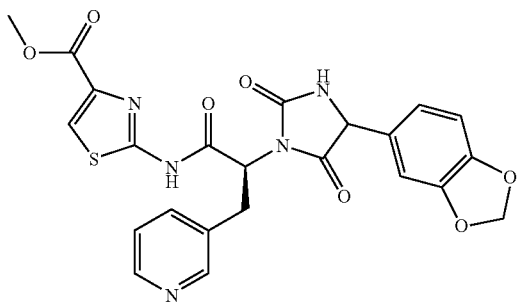

Prepared as described in example 3 except that (S)-2-tert-butoxycarbonylamino-3-pyridin-3-yl-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 510.1082. Calcd. Mass, 510.1078 (M+H).

2-[2-(4-Benzo[1,3]dioxol-5-yl-2,5-dioxo-imidazolidin-1-yl)-3-(tetrahydro-pyran-4-yl)-propionylamino]-thiazole-4-carboxylic acid methyl ester

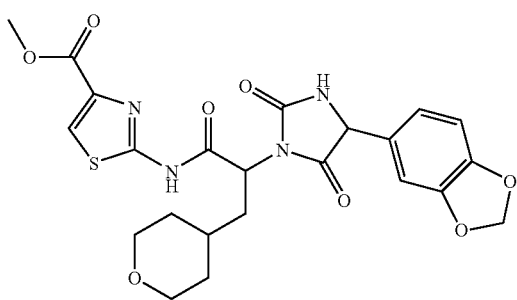

Prepared as described in example 3 except that 2-tert-butoxycarbonylamino-3-(tetrahydro-pyran4-yl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 517.1392. Calcd. Mass, 517.1388 (M+H).

2-[(S)-2-(4-Benzo[1,3]dioxol-5-yl-2,5-dioxo-imidazolidin-1-yl)-3-(1-methyl-1H-imidazol-4-yl)-propionylamino]-thiazole-4-carboxylic acid methyl ester

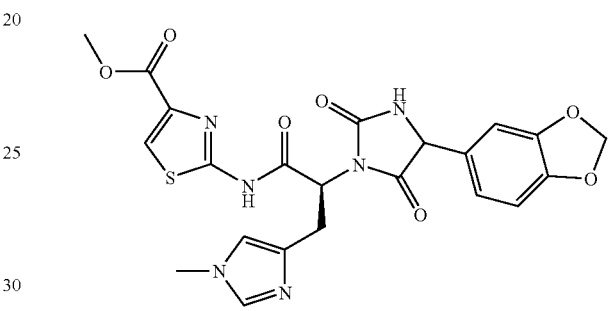

Prepared as described in example 3 except that (S)-2-tert-butoxycarbonylamino-3-(1-methyl-1H-imidazol-4-yl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 513.1192. Calcd. Mass, 513.1187 (M+H).

2-[(S)-2-[4-(2,3-Dihydro-benzo[1,4]dioxin-6-yl)-2,5-dioxo-imidazolidin-1-yl]-3-(4-methanesulfonylamino-phenyl)-propionylamino]-thiazole-4-carboxylic acid methyl ester

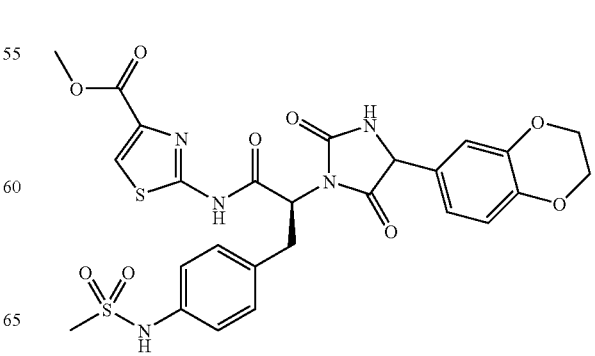

Prepared as described in example 3 except that (S)-2-tert-butoxycarbonylamino-3-(4-methanesulfonylamino-phenyl)-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxybenzaldehyde was used in place of 3-fluoro-4-methoxy-benzaldehyde.

LR-MS: Obs. Mass, 616.0 (positive ion) and 614.0 (negative ion). Calcd. Mass, 616.1172 (M+H) and 614.1016 (M–H).

2-[(S)-2-(4-Benzo[1,3]dioxol-5-yl-2,5-dioxo-imidazolidin-1-yl)-3-phenyl-propionylamino]-thiazole-4-carboxylic acid methyl ester

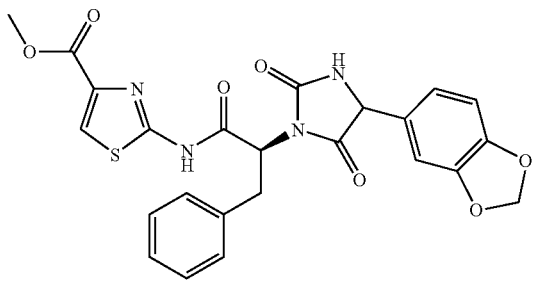

Prepared as described in example 3 except that benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 509.1130. Calcd. Mass, 509.1126 (M+H).

EXAMPLE 5

In a Similar Manner as Described in Example 3, the Following Compounds were Prepared 2-{(S)-2-[4-(2-Fluoro-4-methoxy-phenyl)-2,5-dioxo-imidazolidin-1-yl]-4-methyl-pentanoylamino}-thiazole-4-carboxylic acid methyl ester

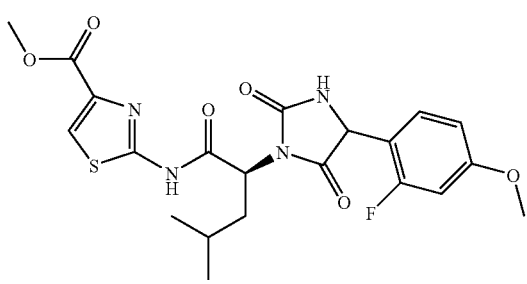

Prepared as described in example 3 except that (S)-2-tert-butoxycarbonylamino-4-methyl-pentanoic acid was used in place of (S)-2-tert-butoxycarbonylamino-3-phenyl-propionic acid in step 3 and tert-butoxycarbonylamino-(2-fluoro-4-methoxy-phenyl)-acetic acid was used in place of tert-butoxycarbonylamino-(3-fluoro-4-methoxy-phenyl)-acetic acid in step 7. tert-Butoxycarbonylamino-(2-fluoro-4-methoxy-phenyl)-acetic acid was prepared as described in example 3, steps 5 and 6, except that 2-fluoro-4-methoxy-benzaldehyde was used in place of 3-fluoro-4-methoxy-benzaldehyde.

HRMS: Obs. Mass, 479.1400. Calcd. Mass, 479.1395 (M+H).

2-{(S)-2-[4-(2,3-Difluoro-phenyl)-2,5-dioxo-imidazolidin-1-yl]-4-methyl-pentanoylamino}-thiazole-4-carboxylic acid methyl ester

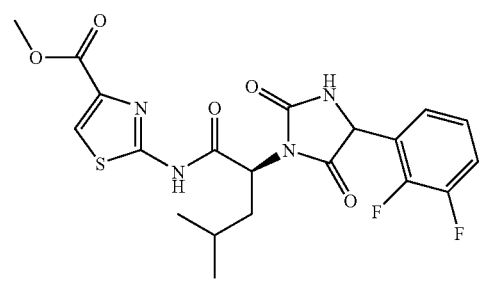

Prepared as described in example 3 except that (S)-2-tert-butoxycarbonylamino-4-methyl-pentanoic acid was used in place of (S)-2-tert-butoxycarbonylamino-3-phenyl-propionic acid in step 3 and tert-butoxycarbonylamino-(2,3-difluoro-phenyl)-acetic acid was used in place of tert-butoxycarbonylamino-(3-fluoro-4-methoxy-phenyl)-acetic acid in step 7. tert-Butoxycarbonylamino-(2,3-difluoro-phenyl)-acetic acid was prepared as described in example 3, steps 5 and 6, except that 2,3-difluoro-benzaldehyde was used in place of 3-fluoro-4-methoxy-benzaldehyde.

HRMS: Obs. Mass, 467.1200. Calcd. Mass, 467.1195 (M+H).

2-{(S)-2-[4-(2-Fluoro4-methoxy-phenyl)-2,5-dioxo-imidazolidin-1-yl]-4-methyl-pentanoylamino}-thiazole-4-carboxylic acid methyl ester

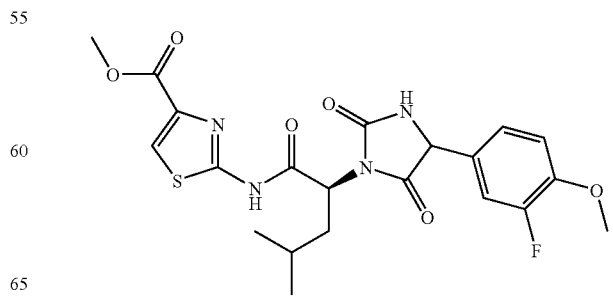

Prepared as described in example 3 except that (S)-2-tert-butoxycarbonylamino-4-methyl-pentanoic acid was used in place of (S)-2-tert-butoxycarbonylamino-3-phenyl-propionic acid in step 3.

HRMS: Obs. Mass, 479.1399. Calcd. Mass, 479.1395 (M+H).

2-{3-Cyclopentyl-(S)-2-[4-(3-fluoro-4-methoxy-phenyl)-2,5-dioxo-imidazolidin-1-yl]propionylamino}-thiazole-4-carboxylic acid methyl ester

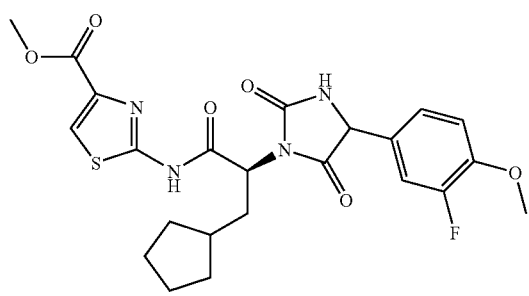

Prepared as described in example 3 except that (S)-2-tert-butoxycarbonylamino-3-cyclopentyl-propionic acid was used in place of (S)-2-tert-butoxycarbonylamino-3-phenyl-propionic acid in step 3.

HRMS: Obs. Mass, 505.1555. Calcd. Mass, 505.1552 (M+H).

(S)-2-[2-(4-Benzo[1,3]dioxol-5-yl-2,5-dioxo-imidazolidin-1-yl)-3-cyclopentyl-propionylamino]-thiazole-4-carboxylic acid methyl ester

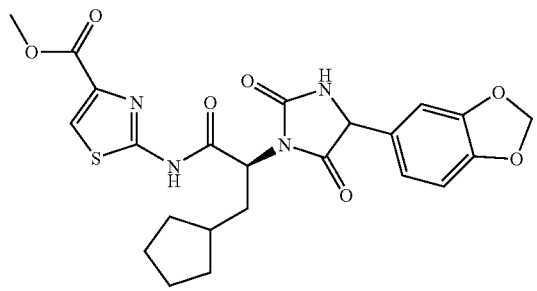

Prepared as described in example 3 except that (S)-2-tert-butoxycarbonylamino-3-cyclopentyl-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 501.1443. Calcd. Mass, 501.1439 (M+H).

(S)-2-[2-(4-Benzo[1,3]dioxol-5-yl-2,5-dioxo-imidazolidin-1-yl)-3-cyclopropyl-propionylamino]-thiazole-4-carboxylic acid methyl ester

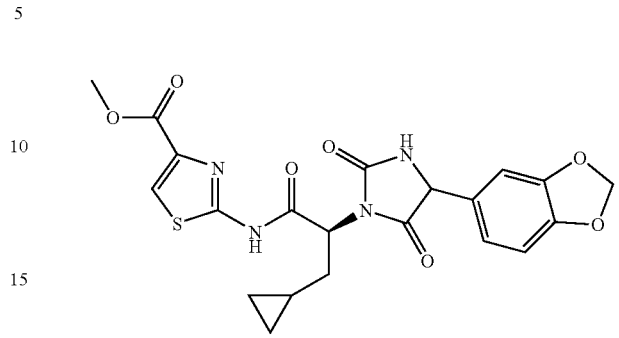

Prepared as described in example 3 except that (S)-2-tert-butoxycarbonylamino-3-cyclopropyl-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 473.1130. Calcd. Mass, 473.1126 (M+H).

(S)-2-[2-(4-Benzo[1,3]dioxol-5-yl-2,5-dioxo-imidazolidin-1-yl)-4-methanesulfonyl-butyrylamino]-thiazole-4-carboxylic acid methyl ester

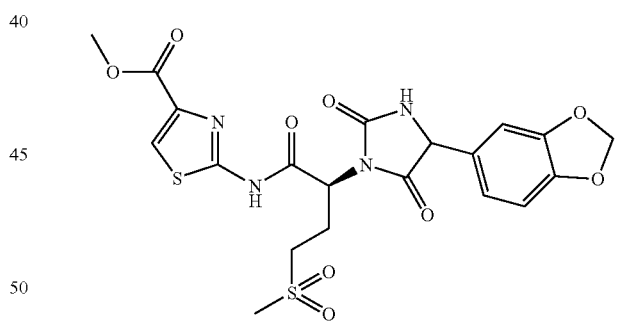

Prepared as described in example 3 except that (S)-2-tert-butoxycarbonylamino-4-methanesulfonyl-butyric acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 525.0747. Calcd. Mass, 525.0745 (M+H).

EXAMPLE 6

In a Similar Manner as Described in Example 3, the Following Compounds were Prepared 2-[(S)-2-(4-Benzo[1,3]dioxol-5-yl-2,5-dioxo-imidazolidin-1-yl)-3-(3-chloro-phenyl)-propionylamino]-thiazole-4-carboxylic acid methyl ester

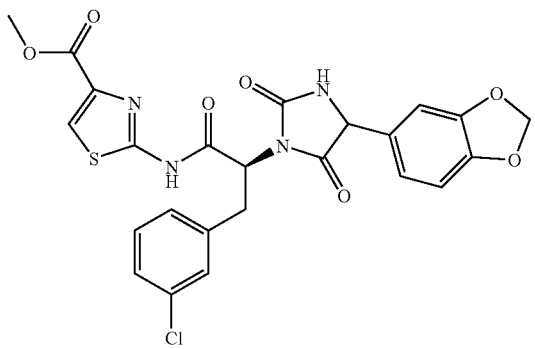

Prepared as described in example 3 except that (S)-2-tert-butoxycarbonylamino-3-(3-chloro-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 543.0742. Calcd. Mass, 543.0736 (M+H).

2-[(S)-2-(4-Benzo[1,3]dioxol-5-yl-2,5-dioxo-imidazolidin-1-yl)-3-(2-chloro-phenyl)-propionylamino]-thiazole-4-carboxylic acid methyl ester

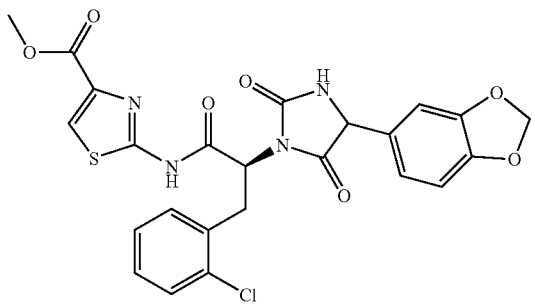

Prepared as described in example 3 except that (S)-2-tert-butoxycarbonylamino-3-(2-chloro-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 543.0736. Calcd. Mass, 543.0736 (M+H).

2-[(S)-2-[4-(2,3-Dihydro-benzo[1,4]dioxin-6-yl)-2,5-dioxo-imidazolidin-1-yl]-3-(2-methoxy-phenyl)-propionylamino]-thiazole-4-carboxylic acid methyl ester

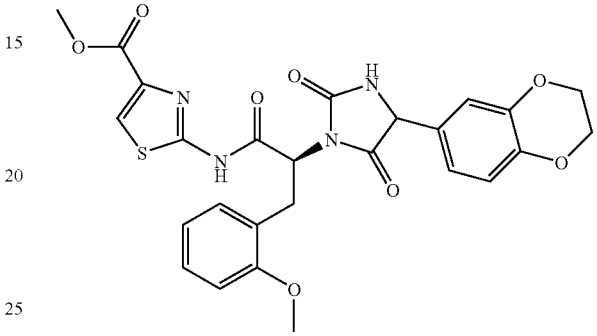

Prepared as described in example 3 except that (S)-2-tert-butoxycarbonylamino-3-(2-methoxy-phenyl)-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 553.1391. Calcd. Mass, 553.1388 (M+H).

2-[(S)-2-(4-Benzo[1,3]dioxol-5-yl-2,5-dioxo-imidazolidin-1-yl)-3-(3-methoxy-phenyl)propionylamino]-thiazole-4-carboxylic acid methyl ester

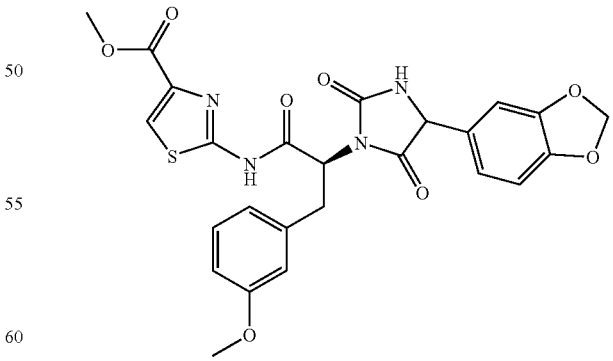

Prepared as described in example 3 except that (S)-2-tert-butoxycarbonylamino-3-(3-methoxy-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxybenzaldehyde was used in place of 3-fluoro-4-methoxybenzaldehyde.

HRMS: Obs. Mass, 539.1235. Calcd. Mass, 535.1231 (M+H).

2-[(S)-2-[4-(3-Fluoro-4-methoxy-phenyl)-2,5-dioxo-imidazolidin-1-yl]-3-(2-methoxy-phenyl)-propionylamino]-thiazole-4-carboxylic acid methyl ester

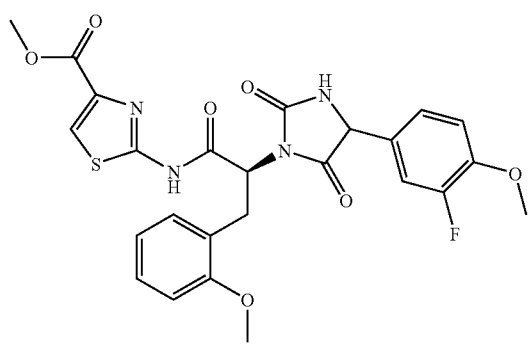

Prepared as described in example 3 except that (S)-2-tert-butoxycarbonylamino-3-(3-methoxy-phenyl)-propionic acid was used in place of (S)-2-tert-butoxycarbonylamino-3-phenyl-propionic acid in step 3.

HRMS: Obs. Mass, 543.1352. Calcd. Mass, 543.1344 (M+H).

2-[(S)-2-(4-Benzo[1,3]dioxol-5-yl-2,5-dioxo-imidazolidin-1-yl)-3-(4-methoxy-phenyl)propionylamino]-thiazole-4-carboxylic acid methyl ester

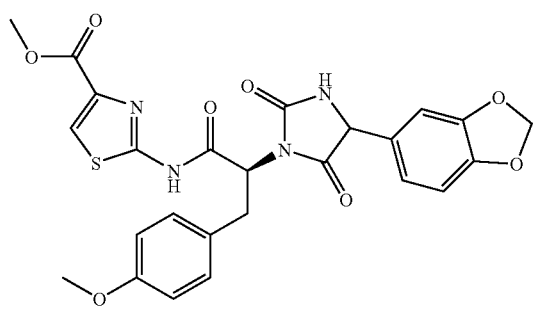

Prepared as described in example 3 except that (S)-2-tert-butoxycarbonylamino-3-(4-methoxy-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxybenzaldehyde was used in place of 3-fluoro-4-methoxybenzaldehyde.

HRMS: Obs. Mass, 539.1235. Calcd. Mass, 539.1231 (M+H).

2-[(S)-2-(4-Benzo[1,3]dioxol-5-yl-2,5-dioxo-imidazolidin-1-yl)-3-o-tolyl-propionylamino]-thiazole-4-carboxylic acid methyl ester

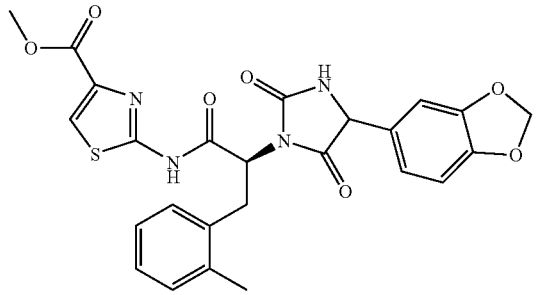

Prepared as described in example 3 except that (S)-2-tert-butoxycarbonylamino-3-(2-methyl-phenyl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxybenzaldehyde was used in place of 3-fluoro-4-methoxybenzaldehyde.

HRMS: Obs. Mass, 522.1223. Calcd. Mass, 522.1209 (M+).

2-{2-[4-(2,3-Dihydro-benzo[1,4]dioxin-6-yl)-2,5-dioxo-imidazolidin-1-yl]-3-indan-1-yl-propionylamino}-thiazole-4-carboxylic acid methyl ester

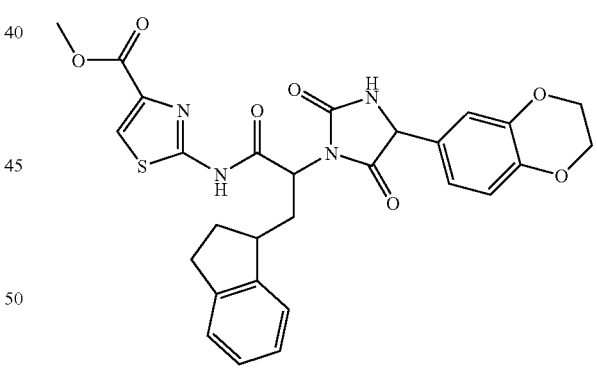

Prepared as described in example 3 except that 2-tert-butoxycarbonylamino-3-indan-1-yl-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 549.1437. Calcd. Mass, 549.1439 (M+H).

2-[(S)-2-[4-(2,3-Dihydro-benzo[1,4]dioxin-6-yl)-2,5-dioxo-imidazolidin-1-yl]-3-(2-fluoro-phenyl)-propionylamino]-thiazole-4-carboxylic acid methyl ester

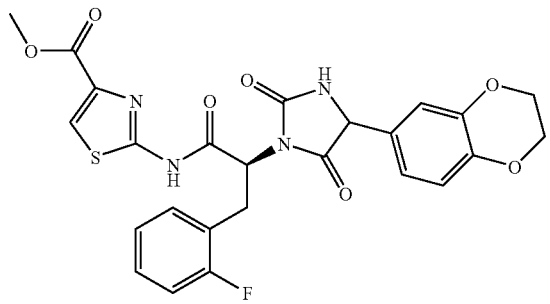

Prepared as described in example 3 except that (S)-2-tert-butoxycarbonylamino-3-(2-fluoro-phenyl)-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 541.1195. Calcd. Mass, 541.1188 (M+H).

2-[(S)-2-[4-(2,3-Dihydro-benzo[1,4]dioxin-6-yl)-2,5-dioxo-imidazolidin-1-yl]-3-(3,4-dimethoxy-phenyl)-propionylamino]-thiazole-4-carboxylic acid methyl ester

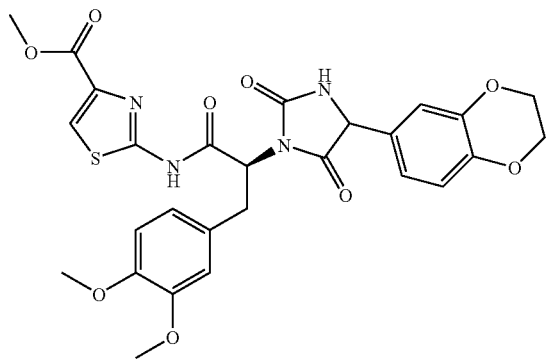

Prepared as described in example 3 except that (S)-2-tert-butoxycarbonylamino-3-(3,4-dimethoxy-phenyl)-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 583.1499. Calcd. Mass, 583.1493 (M+H).

2-[(2-[4-(2,3-Dihydro-benzo[1,4]dioxin-6-yl)-2,5-dioxo-imidazolidin-1-yl]-3-(3-methoxycarbonyl-methoxy-phenyl)-propionylamino]-thiazole-4-carboxylic acid methyl ester

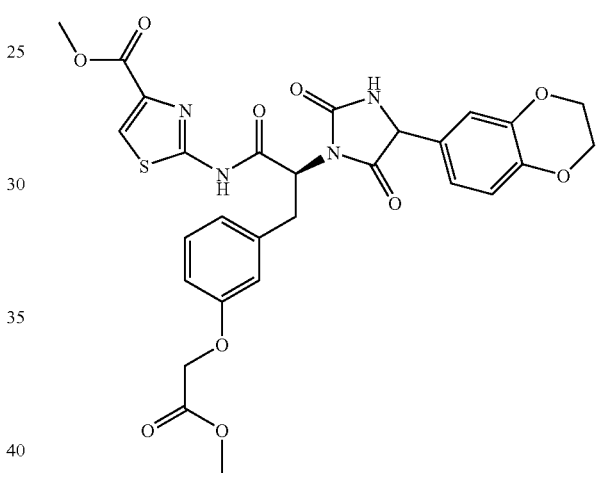

Prepared as described in example 3 except that (S)-2-tert-butoxycarbonylamino-3-(3-methoxycarbonylmethoxy-phenyl)-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde. (S)-2-tert-butoxycarbonylamino-3-(3-methoxycarbonylmethoxy-phenyl)-propionic acid was prepared as described for tert-butoxycarbonylamino-[4-(2-pyrrolidin-1-yl-ethoxy)-phenyl]-acetic acid in example 4(o) except that (S)-2-tert-butoxycarbonylamino-3-(3-hydroxy-phenyl)-propionic acid was used in place of (R)-N-Boc-4-hydroxyphenylglycine and methyl bromoacetate was used in place of chloroethylpyrrolidine hydrochloride.

HRMS: Obs. Mass, 611.1450. Calcd. Mass, 611.1443.

2-{(S)-3-Benzooxazol-5-yl-2-[4-(2,3-dihydro-benzo [1,4]dioxin-6-yl)-2,5-dioxo-imidazolidin-1-yl]-propionylamino}-thiazole-4-carboxylic acid methyl ester

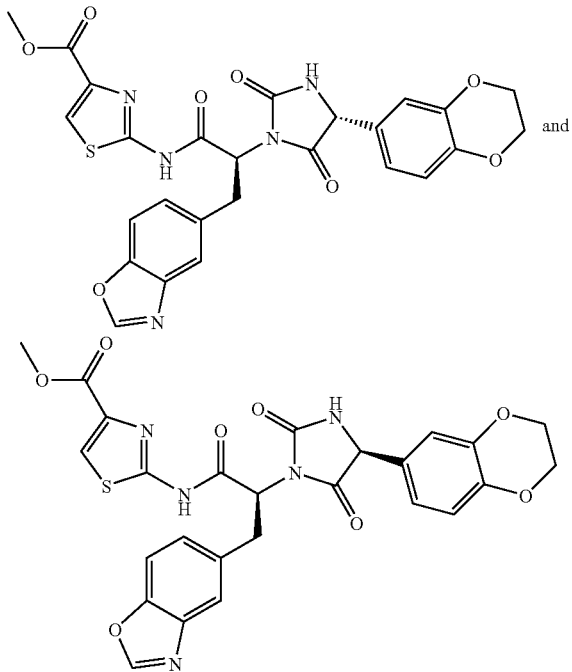

Prepared as described in example 3 except that (S)-3-benzooxazol-5-yl-2-tert-butoxycarbonylamino-propionic acid was used in place of (S)-2-tert-butoxycarbonylamino-3-phenyl-propionic acid used in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid used in step 7. tert-Butoxycarbonylamino-(2,3-dihydro-benzo[1,4]dioxin-6-yl)-acetic acid was prepared as described in example 3, steps 5 and 6, except that 3,4-ethylenedioxybenzaldehyde was used in place of 3-fluoro-4-methoxy-benzaldehyde. (S)-3-benzooxazol-5-yl-2-tert-butoxycarbonylamino-propionic acid was prepared as follows:

To a suspension of (S)-2-amino-3-(4-hydroxy-3-nitrophenyl)-propionic acid ethyl ester hydrochloride (3.63 g, 12.5 mmol) in acetonitrile (125 mL) was added diisopropylethylamine (2.4 mL, 13.8 mmol) and di-tert-butyldicarbonate (3.00 g, 13.7 mmol). The mixture was stirred at room temperature for 72 hours the poured into water (500 mL), diluted with brine (100 mL) and extracted with ethyl acetate (3×200 mL). The combined organic extracts were washed with 0.1 M aqueous hydrochloric acid (2×100 mL), brine (200 mL), dried over sodium sulfate, filtered and concentrated in vacuo to give crude (S)-2-tert-butoxycarbonylamino-3-(4-hydroxy-3-nitro-phenyl)-propionic acid ethyl ester as a dark yellow solid which was used without further purification (4.63 g).

LR-MS: Observed m/z(M−H)=353.3.

To a vigorously stirred solution of (S)-2-tert-butoxycarbonylamino-3-(4-hydroxy-3-nitro-phenyl)-propionic acid ethyl ester (1.00 g, 2.82 mmol) in methanol (50 mL) was added a solution of ammonium chloride (2.26 g, 42.3 mmol) in water (25 mL) followed by zinc dust (<10 μM particle size) (1.84 g, 28.1 mmol). After stirring at ambient temperature for 30 minutes the reaction mixture was filtered through a pad of Celite® and residual soluble material eluted from the pad with methanol. The filtrate was concentarted in vacuo and the aqueous residue poured into water (100 mL), diluted with brine (50 mL) and extracted with ethyl acetate (3×50 mL). The combined organic extracts were washed with brine (75 mL), dried over sodium sulfate and concentrated in vacuo to give crude 3-(3-amino-4-hydroxy-phenyl)-2-tert-butoxycarbonylamino-propionic acid ethyl ester as a green viscous solid which was used without further purification (0.89 g, 97%).

LR-MS: Observed m/z(M+H)=325.4.

To a solution of crude 3-(3-amino-4-hydroxy-phenyl)-2-tert-butoxycarbonylamino-propionic acid ethyl ester (0.89 g, 2.74 mmol) in toluene (20 mL) was added triethyl orthoformate (0.57 mL, 3.36 mmol) and the mixture was heated to 75° C. under an atmosphere of argon for 3 hours at which time all starting material had been consumed. The reaction mixture was concentrated in vacuo to a black waxy solid which was dissolved in acetonitrile (25 mL) and di-tert-butyldicarbonate (0.80 g, 3.67 mmol) added. The mixture was stirred at ambient temperature under an atmosphere of argon for 16 hours then poured into water (100 mL), diluted with brine (50 mL) and extracted with ethyl acetae (3×50 mL). The combined organic extracts were washed with brine (100 mL), dried over sodium sulfate and concentrated in vacuo to a black viscous oil. Purification by chromatography over silica gel eluted with 35% ethyl acetate/65% hexanes gave (S)-3-benzooxazol-5-yl-2-tert-butoxycarbonylamino-propionic acid ethyl ester as a colorless solid (0.54 g, 59%).

LR-MS: Observed m/z(M+H)=335.3.

To a solution of (S)-3-benzooxazol-5-yl-2-tert-butoxycarbonylamino-propionic acid ethyl ester (0.54 g, 1.61 mmol) in tetrahydrofuran (10 mL) was added water (5 mL) and lithium hydroxide monohydrate (111 mg, 2.65 mmol) and the mixture stirred at ambient temperature under argon for 1 hour. The reaction mixture was poured into water (50 mL), diluted with brine (25 mL) and extracted with ethyl acetate (3×25 mL). The combined organic extracts were washed with brine (50 mL), dried over sodium sulfate and concentrated in vacuo to give crude (S)-3-benzooxazol-5-yl-2-tert-butoxycarbonylamino-propionic acid an off white solid foam which was used without further purification (0.49 g, 99%).

LR-MS: Observed m/z(M+H)=307.3.

The 2 isomers of 2-{(S)-3-benzooxazol-5-yl-2-[4-(2,3-dihydro-benzo[1,4]dioxin-6-yl)-2,5-dioxo-imidazolidin-1-yl]-propionylamino}-thiazole-4-carboxylic acid methyl ester were separated by chromatography over silica gel eluted with 3:1 chloroform/tetrahydrofuran. The isomer eluted first is referred to as isomer 1 and the isomer eluted second is referred to as isomer 2.

2-{(S)-3-Benzooxazol-5-yl-2-[4-(2,3-dihydro-benzo[1,4] dioxin-6-yl)-2,5-dioxo-imidazolidin-1-yl]-propionylamino}-thiazole-4-carboxylic acid methyl ester, isomer 1.

HRMS: Obs. Mass, 564.1182. Calcd. Mass, 564.1184 (M+H).

2-{(S)-3-benzooxazol-5-yl-2-[4-(2,3-dihydro-benzo[1,4] dioxin-6-yl)-2,5-dioxo-imidazolidin-1-yl]-propionylamino}-thiazole-4-carboxylic acid methyl ester, isomer 2.

HRMS: Obs. Mass, 564.1184. Calcd. Mass, 564.1184 (M+H).

2-[(S)-2-[4-(2,3-Dihydro-benzo[1,4]dioxin-6-yl)-2,5-dioxo-imidazolidin-1-yl]-3-(4-(S)-dimethylamino-phenyl)-propionylamino]-thiazole-4-carboxylic acid methyl ester

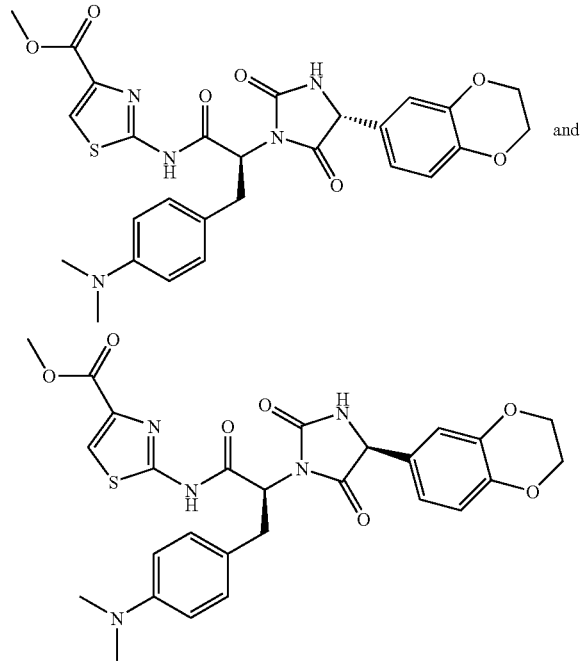

and

Prepared as described in example 3 except that (S)-2-tert-butoxycarbonylamino-3-(4-dimethylamino-phenyl)-propionic acid was used in place of (S)-2-tert-butoxycarbonylamino-3-phenyl-propionic acid used in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid used in step 7. tert-Butoxycarbonylamino-(2,3-dihydro-benzo[1,4]dioxin-6-yl)-acetic acid was prepared as described in example 3, steps 5 and 6, except that 3,4-ethylenedioxybenzaldehyde was used in place of 3-fluoro-4-methoxy-benzaldehyde. (S)-2-tert-butoxycarbonylamino-3-(4-dimethylamino-phenyl)-propionic acid was prepared as described by Sisido et al., *J. Am. Chem. Soc.* 1989, 111, 6790.

The 2 isomers of 2-[(S)-2-[4-(2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester were separated by chromatography over silica gel eluted with 90:1:10:6 v/v mixture of chloroform/methanol/water/acetic acid. The isomer eluted first is referred to as isomer 1 and the isomer eluted second is referred to as isomer 2.

2-[(S)-2-[4-(2,3-Dihydro-benzo[1,4]dioxin-6-yl)-2,5-dioxo-imidazolidin-1yl]-3-(4-dimethylamino-phenyl)-propionylamino]-thiazole-4-carboxylic acid methyl ester, isomer 1 RO4903745-000-001

HRMS: Obs. Mass, 566.1704. Calcd. Mass, 566.1704 (M+H).

2-[(S)-2-[4-(2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester, isomer 2.

HRMS: Obs. Mass, 566.1702. Calcd. Mass, 566.1704 (M+H).

EXAMPLE 7

In a Similar Manner as Prepared in Example 3, the Following Compounds were Prepared 2-{(S)-2-[4-(3-Fluoro-4-methoxy-phenyl)-2,5-dioxo-imidazolidin-1-yl]-3-thiazol-4-ylpropionylamino}-thiazole-4-carboxylic acid methyl ester

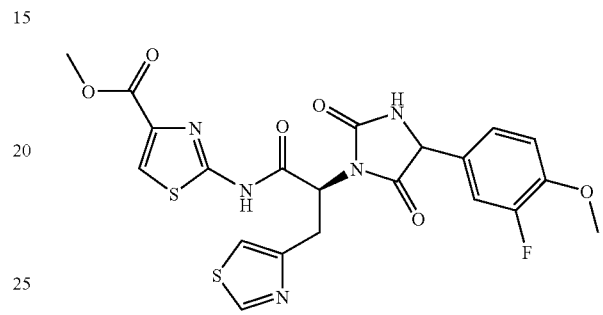

Prepared as described in example 3 except that (S)-2-tert-butoxycarbonylamino-3-thiazol-4-yl-propionic acid was used in place of (S)-2-tert-butoxycarbonylamino-3-phenyl-propionic acid in step 3.

HRMS: Obs. Mass, 520.0753. Calcd. Mass, 520.0756 (M+H).

2-[(S)-2-(4-Benzo[1,3]dioxol-5-yl-2,5-dioxo-imidazolidin-1-yl)-3-thiazol-4-yl-propionylamino]-thiazole-4-carboxylic acid methyl ester

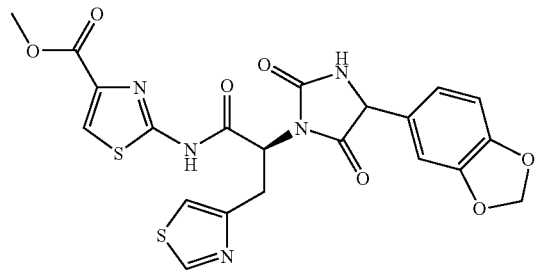

Prepared as described in example 3 except that (S)-2-tert-butoxycarbonylamino-3-thiazol-4-yl-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 516.0647. Calcd. Mass, 516.0642 (M+H).

2-{(S)-2-[4-(2,3-Dihydro-benzo[1,4]dioxin-6-yl)-2,5-dioxo-imidazolidin-1-yl]-3-thiazol-4-yl-propionylamino}-thiazole-4-carboxylic acid methyl ester

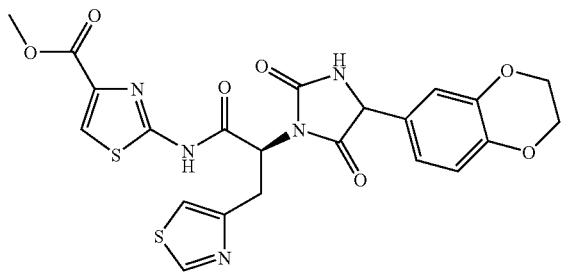

Prepared as described in example 3 except that (S)-2-tert-butoxycarbonylamino-3-thiazol-4-yl-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 530.0805. Calcd. Mass, 530.0799 (M+H).

2-{(S)-2-[4-(3-Fluoro-4-methoxy-phenyl)-2,5-dioxo-imidazolidin-1-yl]-3-furan-2-yl-propionylamino}-thiazole-4-carboxylic acid methyl ester

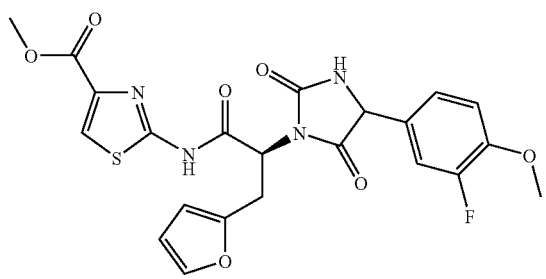

Prepared as described in example 3 except that (S)-2-tert-butoxycarbonylamino-3-furan-2-yl-propionic acid was used in place of (S)-2-tert-butoxycarbonylamino-3-phenyl-propionic acid in step 3.

HRMS: Obs. Mass, 503.1035. Calcd. Mass, 503.1031 (M+H).

2-[(S)-2-(4-Benzo[1,3]dioxol-5-yl-2,5-dioxo-imidazolidin-1-yl)-3-(3-methyl-3H-imidazol-4-yl)-propionylamino]-thiazole-4-carboxylic acid methyl ester

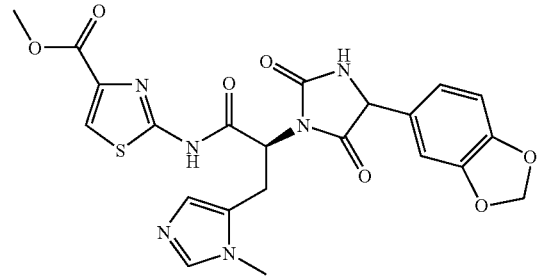

Prepared as described in example 3 except that (S)-2-tert-butoxycarbonylamino-3-(3-methyl-3H-imidazol-4-yl)-propionic acid was used in place of (S)-2-tert-butoxycarbonylamino-3-phenyl-propionic acid in step 3 and benzo[1,3]dioxol-5-yl-tert-butoxycarbonylamino-acetic acid was used in place of tert-butoxycarbonylamino-(3-fluoro-4-methoxy-phenyl)-acetic acid in step 7. Benzo[1,3]dioxol-5-yl-tert-butoxycarbonylamino-acetic acid was prepared as described in example 3, steps 5 and 6, except that 3,4-methylenedioxy-benzaldehyde was used in place of 3-fluoro-4-methoxy-benzaldehyde.

HRMS: Obs. Mass, 513.1193. Calcd. Mass, 513.1187 (M+H).

2-{(S)-2-[4-(2,3-Dihydro-benzo[1,4]dioxin-6-yl)-2,5-dioxo-imidazolidin-1-yl]-3-pyridin-3-yl-propionylamino}-thiazole-4-carboxylic acid methyl ester

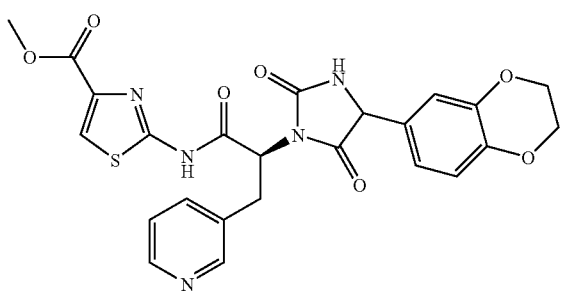

Prepared as described in example 3 except that (S)-2-tert-butoxycarbonylamino-3-pyridin-3-yl-propionic acid was used in place of (S)-2-tert-butoxycarbonylamino-3-phenyl-propionic acid in step 3 and tert-butoxycarbonylamino-(2,3-dihydro-benzo[1,4]dioxin-6-yl)-acetic acid was used in place of tert-butoxycarbonylamino-(3-fluoro-4-methoxy-phenyl)-acetic acid in step 7. tert-Butoxycarbonylamino-(2,3-dihydro-benzo[1,4]dioxin-6-yl)-acetic acid was prepared as described in example 3, steps 5 and 6, except that 3,4-ethylenedioxy-benzaldehyde was used in place of 3-fluoro-4-methoxy-benzaldehyde.

HRMS: Obs. Mass, 524.1229. Calcd. Mass, 524.1235 (M+H).

EXAMPLE 8

2-{(S)-2-[(R)-4-(3-Fluoro4-methoxy-phenyl)-2,5-dioxo-imidazolidin-1-yl]-3-phenyl-propionylamino}-thiazole-4-carboxylic acid methyl ester

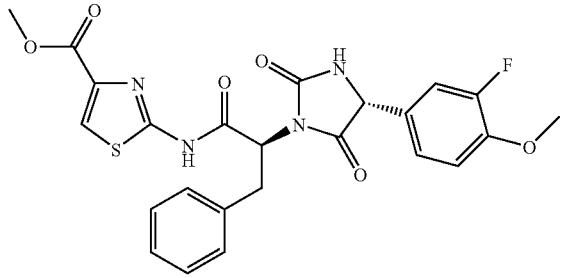

Recrystallization of 2-{(S)-2-[4-(3-fluoro-4-methoxy-phenyl)-2,5-dioxo-imidazolidin-1-yl]-3-phenyl-propionylamino}-thiazole-4-carboxylic acid methyl ester from acetonitrile gave 2-{(S)-2-[(R)-4-(3-fluoro-4-methoxy-phenyl)-2,5-dioxo-imidazolidin-1-yl]-3-phenyl-propionylamino}-thiazole-4-carboxylic acid methyl ester.

HRMS: Obs. Mass, 513.1245. Calcd. Mass, 513.1239 (M+H).

2-{(S)-2-[(S)-4-(3-Fluoro4-methoxy-phenyl)-2,5-dioxo-imidazolidin-1-yl]-3-phenyl-propionylamino}-thiazole-4-carboxylic acid methyl ester

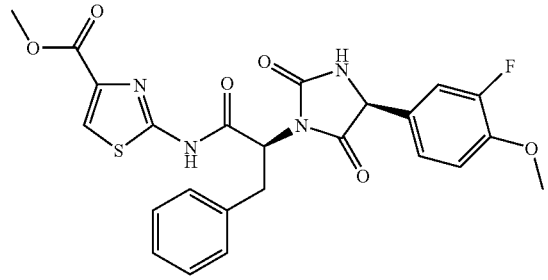

From the mother liquors of the above recrystallization it was possible to recover the other diastereomer present in the starting mixture.

HRMS: Obs. Mass, Calcd. Mass, 513.1239 (M+H).

EXAMPLE 9

In a Similar Manner as Described in Example 8, the Following Compounds were Prepared from the Corresponding Mixture of Diastereoisomers 2-{(S)-2-[(R)-4-(3-Chloro-4-methoxy-phenyl)-2,5-dioxo-imidazolidin-1-yl]-3-phenyl-propionylamino}-thiazole-4-carboxylic acid methyl ester

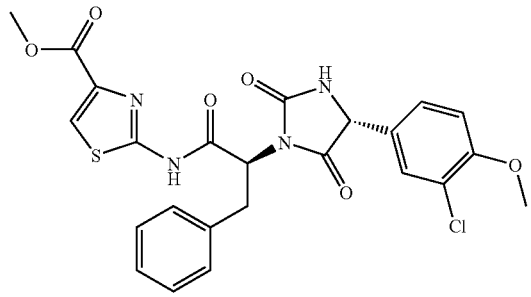

Crystallization of 2-{(S)-2-[4-(3-chloro-4-methoxy-phenyl)-2,5-dioxo-imidazolidin-1-yl]-3-phenyl-propionylamino}-thiazole-4-carboxylic acid methyl ester, prepared as described in example 4(g), from acetonitrile.

HRMS: Obs. Mass, 529.0947. Calcd. Mass, 529.0943 (M+H).

2-{(S)-2-[(R)-4-Benzo[1,3]dioxol-5-yl-2,5-dioxo-imidazolidin-1-yl]-3-phenyl-propionylamino}-thiazole-4-carboxylic acid methyl ester

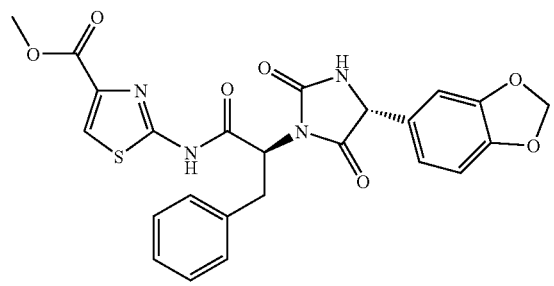

Crystallization of 2-{(S)-2-[4-benzo[1,3]dioxol-5-yl-2,5-dioxo-imidazolidin-1-yl]-3-phenyl-propionylamino}-thiazole-4-carboxylic acid methyl ester, prepared as described in example 4(cc), from acetonitrile.

HRMS: Obs. Mass, 509.1131. Calcd. Mass, 509.1126 (M+H).

2-{(S)-2-[(R)-4-(3,5-Difluoro-phenyl)-2,5-dioxo-imidazolidin-1-yl]-3-phenyl-propionylamino}-thiazole-4-carboxylic acid methyl ester

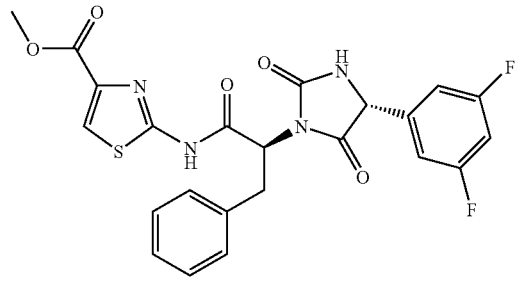

Crystallization of 2-{(S)-2-[4-(3,5-difluoro-phenyl)-2,5-dioxo-imidazolidin-1-yl]-3-phenyl-propionylamino}-thiazole-4-carboxylic acid methyl ester, prepared as described in example 4(h), from acetonitrile.

HRMS: Obs. Mass, 501.1043. Calcd. Mass, 501.1039 (M+H).

2-{(S)-2-[(R)-4-(3-Fluoro4-methoxy-phenyl)-2,5-dioxo-imidazolidin-1-yl]-3-(2-methoxy-phenyl)-propionylamino}-thiazole-4-carboxylic acid methyl ester

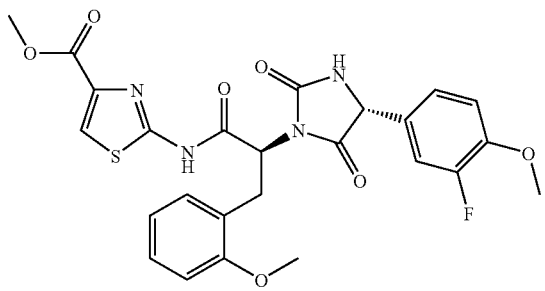

Crystallization of 2-{(S)-2-[4-(3-fluoro-4-methoxy-phenyl)-2,5-dioxo-imidazolidin-1-yl]-3-(2-methoxy-phenyl)-propionylamino}-thiazole-4-carboxylic acid methyl ester, prepared as described in example 6(e), from acetonitrile.

HRMS: Obs. Mass, 543.1351. Calcd. Mass, 543.1344 (M+H).

2-[(S)-2-((R)-4-Benzo[1,3]dioxol-5-yl-2,5-dioxo-imidazolidin-1-yl)-3-cyclopropyl-propionylamino]-thiazole-4-carboxylic acid methyl ester

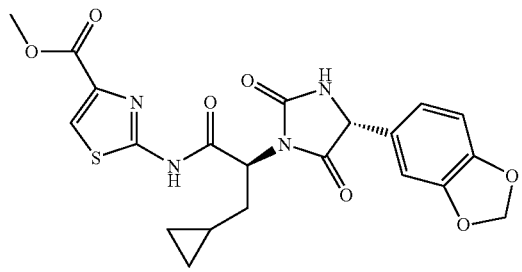

Crystallization of 2-[(S)-2-(4-benzo[1,3]dioxol-5-yl-2,5-dioxo-imidazolidin-1-yl)-3-cyclopropyl-propionylamino]-thiazole-4-carboxylic acid methyl ester, prepared as described in example 5(f), from acetonitrile.

HRMS: Obs. Mass, 473.1129. Calcd. Mass, 473.1126 (M+H).

2-[(S)-2-((R)-4-Benzo[1,3]dioxol-5-yl-2,5-dioxo-imidazolidin-1-yl)-3-cyclopentyl-propionylamino]-thiazole-4-carboxylic acid methyl ester

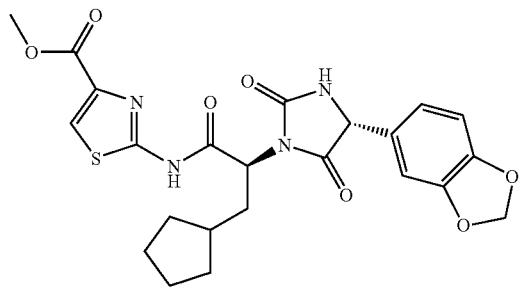

Crystallization of 2-[(S)-2-(4-benzo[1,3]dioxol-5-yl-2,5-dioxo-imidazolidin-1-yl)-3-cyclopentyl-propionylamino]-thiazole-4-carboxylic acid methyl ester, prepared as described in example 5(e), from acetonitrile.

HRMS: Obs. Mass, 501.1441. Calcd. Mass, 501.1439 (M+H).

2-{3-Cyclopentyl-(S)-2-[(R)-4-(3-fluoro-4-methoxy-phenyl)-2,5-dioxo-imidazolidin-1-yl]-propionylamino)thiazole-4-carboxylic acid methyl ester

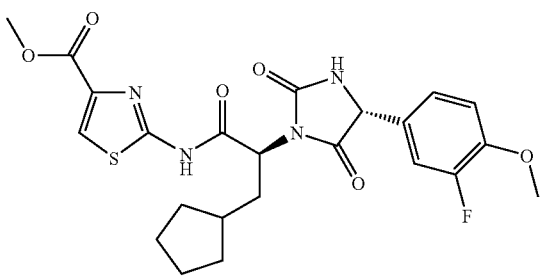

Crystallization of 2-{3-cyclopentyl-(S)-2-[4-(3-fluoro4-methoxy-phenyl)-2,5-dioxo-imidazolidin-1-yl]propionylamino}-thiazole-4-carboxylic acid methyl ester, prepared as described in example 5(d), from acetonitrile.

HRMS: Obs. Mass, 505.1558. Calcd. Mass, 505.1552 (M+H).

2-[(S)-2-((S)-25-Dioxo-4-thiophen-3-yl-imidazolidin-1-yl)-3-phenyl-propionylamino]-thiazole-4-carboxylic acid methyl ester

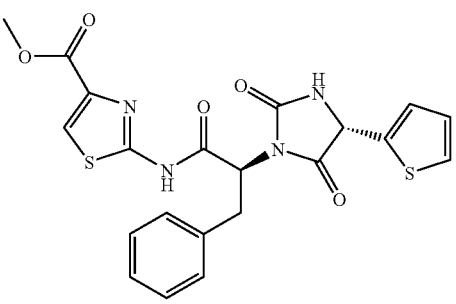

Crystallization of 2-[(S)-2-(2,5-dioxo-4-thiophen-2-yl-imidazolidin-1-yl)-3-phenyl-propionylamino]-thiazole-4-carboxylic acid methyl ester, prepared as described in example 4(u), from ethyl acetate.

HRMS: Obs. Mass, 471.0795. Calcd Mass, 471.0792 (M+H).

2-{(S)-2-[(R)-4-(4-Methoxy-phenyl)-2,5-dioxo-imidazolidin-1-yl]-3-thiazol-2-yl-propionylamino}-thiazole-4-carboxylic acid methyl ester

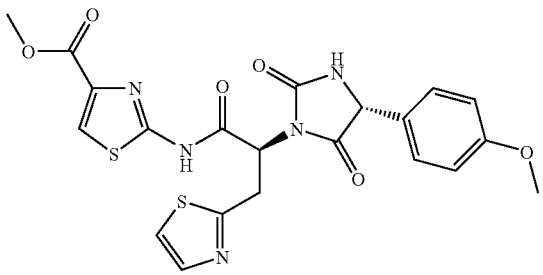

Crystallization of 2-{2-[(R)-4-(4-methoxy-phenyl)-2,5-dioxo-imidazolidin-1-yl]-3-thiazol-2-yl-propionylamino}-thiazole-4-carboxylic acid methyl ester, prepared as described in example II(I), from acetonitrile.

HRMS: Obs. Mass, 502.0853. Calcd. Mass, 502.0850 (M+H).

2-{(S)-2-[(R)-4-(2-Fluoro-4-methoxy-phenyl)-2,5-dioxo-imidazolidin-1-yl]-3-phenyl-propionylamino}-thiazole-4-carboxylic acid methyl ester

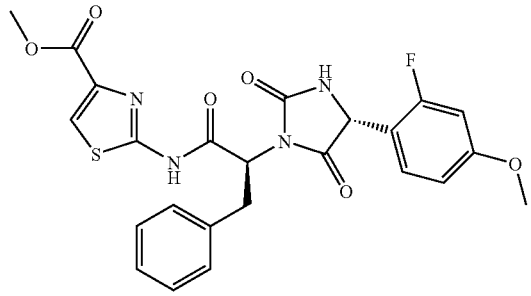

Crystallization of 2-{(S)-2-[4-(2-fluoro-4-methoxy-phenyl)-2,5-dioxo-imidazolidin-1-yl]-3-phenyl-propionylamino}-thiazole-4-carboxylic acid methyl ester, prepared as described in example 4(k), from acetonitrile.

HRMS: Obs. Mass, 513.1244. Calcd. Mass, 513.1239 (M+H).

EXAMPLE 10

2-[(S)-2-(2,5-Dioxo-(R)-4-phenyl-imidazolidin-1-yl)-3-phenyl-propionylamino]-thiazole-4-carboxylic acid methyl ester

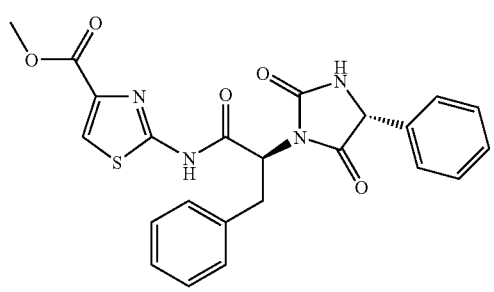

A solution of 2-((S)-2-amino-3-phenyl-propionylamino)-thiazole-4-carboxylic acid methyl ester (prepared as described in example 3, step c) (0.61 g, 2.0 mmol), (R)-tert-butoxycarbonylamino-phenylacetic acid (0.55 g, 2.2 mmol), diisopropylethylamine (1.40 mL, 7.88 mmol) and 1-hydroxybenzotriazole (0.324 g, 2.40 mmol) in N,N-dimethylformamide (5 mL) was stirred in an ice bath for 5 minutes To the cooled yellow-orange solution was added O-benzotriazol-1-yl-N,N,N',N'-tetramethyluronium hexafluorophosphate (0.91 g, 2.40 mmol). The reaction mixture was stirred for 5 minutes and the ice bath was removed and stirring continued for 1 hour. The reaction mixture was then diluted with ethyl acetate, washed brine and the aqueous layer extracted with ethyl acetate. The combined organic extracts were passed through a pad of sodium sulfate layered on the top of a pad of silica gel contained in a 60 mL vacuum filtration funnel. Residual material was eluted from the pad of sodium sulfate and silica gel with ethyl acetate and the filtrate was concentrated in vacuo to give —[(S)-2-((R)-2-tert-butoxycarbonylamino-2-phenyl-acetylamino)-3-phenyl-propionylamino]-thiazole-4-carboxylic acid methyl ester which was taken into dry dichloromethane (10 mL) under argon and cooled in an ice bath. To this was added trifluoroacetic acid (5 mL, 64.9 mmol) and the mixture stirred at 0° C. for 2 hours. The reaction mixture was then concentrated to dryness. The residue was taken into dichloromethane and precipitated with ether and the suspension was stirred for 15 minutes. The solid was isolated by filtration and washed with ether and dried to give a tan solid. The solid was taken into dichloromethane and washed with saturated aqueous sodium bicarbonate solution. The organic layer was separated, dried over sodium sulfate, filtered, concentrated and dried to give 2-[(S)-2-((R)-2-amino-2-phenyl-acetylamino)-3-phenyl-propionylamino]-thiazole-4-carboxylic acid methyl ester as an off white foam (0.80 g, 91%).

A solution of 2-[(S)-2-((R)-2-amino-2-phenyl-acetylamino)-3-phenyl-propionylamino]-thiazole-4-carboxylic acid methyl ester (0.795 g, 1.82 mmol) and diisopropylethylamine (1.10 mL, 6.2 mmol) in tetrahydrofuran (20 mL) was added to a solution of diphosgene (0.151 µL, 1.27 mmol) in a mixture of toluene (20 mL) and tetrahydrofuran (20 mL) over 10 minute at 0° C. The mixture was stirred at 0° C. for 20 minute then diluted with ethyl acetate. The mixture was washed with water, brine and dried over sodium sulfate. Evaporation of the solvents and purification of the residue by chromatography over silica gel gradient eluted between 0.2 and 1.2% v/v methanol in dichloromethane followed by recrystallization of the isolated product from acetonitrile gave 2-[(S)-2-((R)-2,5-dioxo-4-phenyl-imidazolidin-1-yl)-3-phenyl-propionylamino]-thiazole-4-carboxylic acid methyl ester as a white crystalline solid (166 mg, 20%).

HRMS: Obs. Mass, 465.1227. Calcd. Mass, 465.1227 (M+H).

EXAMPLE 11

In a similar as described in example 10, the following compounds were prepared. (2R)-tert-butoxycarbonylamino-(2,3-dihydro-benzo[1,4]dioxin-6-yl)-acetic acid was prepared according to the procedure of Bohme, E. H. W.; Bambury, R. E. et al. *J. Med. Chem.* 1980, 23, 405-412). (R)—N-(tert-butyloxycarbonyl)-4-methoxyphenylglycine was prepared according to the procedure of Hyun, M. H., et al. *J. Liq. Chrom. & Rel. Technol.* 2002, 25, 573-588).

2-{(S)-2-[(R)-4-(2,3-Dihydro-benzo[1,4]dioxin-6-yl)-2,5-dioxo-imidazolidin-1-yl]-3-phenyl-propionylamino}-thiazole-4-carboxylic acid methyl ester

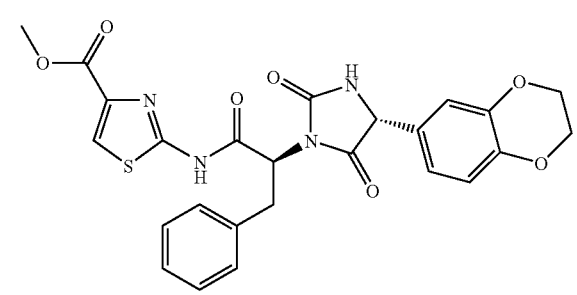

Prepared as described in example 10 except that (2R)-tert-butoxycarbonylamino-(2,3-dihydro-benzo[1,4]dioxin-6-yl)-acetic acid was used in place of (R)-tert-butoxycarbonylamino-phenylacetic acid in step 1.

HRMS: Obs. Mass, 523.1286. Calcd. Mass, 523.1282 (M+H).

2-{(S)-2-[(R)-4-(2,3-Dihydro-benzo[1,4]dioxin-6-yl)-2,5-dioxo-imidazolidin-1-yl]-3-(4-fluoro-phenyl)-propionylamino}-thiazole-4-carboxylic acid methyl ester

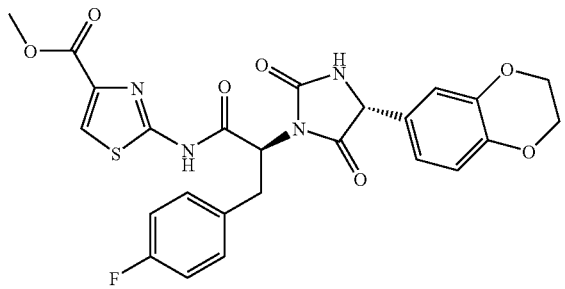

Prepared as described in example 10 except that (2R)-tert-butoxycarbonylamino-(2,3-dihydro-benzo[1,4]dioxin-6-yl)-acetic acid and 2-((S)-2-amino-3-(4-fluoro-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(4-fluoro-phenyl)-propionylamino)-thiazole-4-carboxylic acid methyl ester was prepared as described in example 3 except that (S)-2-tert-butoxycarbonylamino-3-(4-fluoro-phenyl)-propionic acid was used in place of (S)-2-tert-butoxycarbonylamino-3-phenyl-propionic acid in step 3.

HRMS: Obs. Mass, 541.1188. Calcd. Mass, 541.1188 (M+H).

2-{3-(3,5-Difluoro-phenyl)-(S)-2-[(R)4-(2,3-dihydro-benzo[1,4]dioxin-6-yl)-2,5-dioxo-imidazolidin-1-yl]-propionylamino}-thiazole-4-carboxylic acid methyl ester

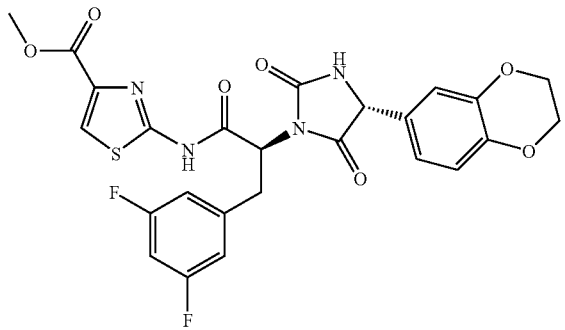

Prepared as described in example 10 except that (2R)-tert-butoxycarbonylamino-(2,3-dihydro-benzo[1,4]dioxin-6-yl)-acetic acid and 2-((S)-2-amino-3-(3,5-difluoro-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole4-carboxylic acid methyl ester respectively in step 1. 2-((S)-2-Amino-3-(3,5-difluoro-phenyl)-propionylamino)-thiazole-4-carboxylic acid methyl ester was prepared as described in example 3 except that (S)-2-tert-butoxycarbonylamino-3-(3,5-difluoro-phenyl)-propionic acid was used in place of (S)-2-tert-butoxycarbonylamino-3-phenyl-propionic acid in step 3.

HRMS: Obs. Mass, 559.1087. Calcd. Mass, 559.1094 (M+H).

2-[(S)-2-[(R)-4-(2,3-Dihydro-benzo[1,4]dioxin-6-yl)-2,5-dioxo-imidazolidin-1-yl]-3-(2-fluoro-phenyl)-propionylamino]-thiazole-4-carboxylic acid methyl ester

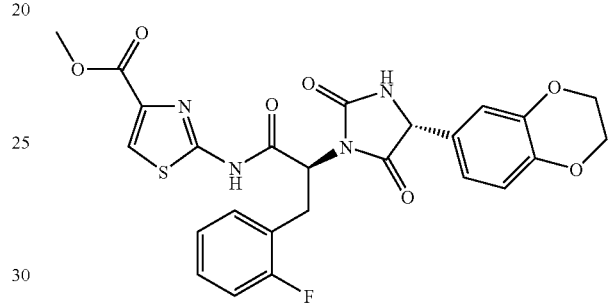

Prepared as described in example 10 except that (2R)-tert-butoxycarbonylamino-(2,3-dihydro-benzo[1,4]dioxin-6-yl)-acetic acid and 2-((S)-2-amino-3-(2-fluoro-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(2-fluoro-phenyl)-propionylamino)-thiazole-4-carboxylic acid methyl ester was prepared as described in example 3 except that (S)-2-tert-butoxycarbonylamino-3-(2-fluoro-phenyl)-propionic acid was used in place of (S)-2-tert-butoxycarbonylamino-3-phenyl-propionic acid in step 3.

HRMS: Obs. Mass, 541.1195. Calcd. Mass, 541.1188 (M+H).

2-{(S)-2-[(R)-4-(4-Methoxy-phenyl)-2,5-dioxo-imidazolidin-1-yl]-3-phenyl-propionylamino}-thiazole-4-carboxylic acid methyl ester

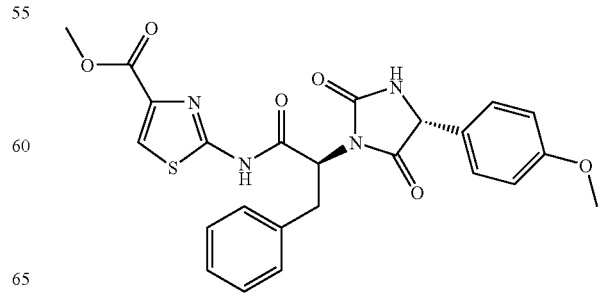

Prepared as described in example 10 except that (R)—N-(tert-butyloxycarbonyl)-4-methyoxyphenylglycine was used in place of (R)-tert-butoxycarbonylamino-phenylacetic acid in step 1.

HRMS: Obs. Mass, 495.1340. Calcd. Mass, 495.1333 (M+H).

2-{3-(2-Methoxy-phenyl)-(S)-2-[(R)-4-(4-methoxy-phenyl)-2,5-dioxo-imidazolidin-1-yl]-propionylamino}-thiazole-4-carboxylic acid methyl ester

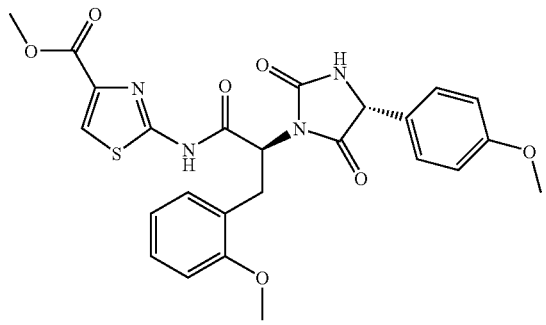

Prepared as described in example 10 except that (R)—N-(tert-butyloxycarbonyl)-4-methyoxyphenylglycine and 2-((S)-2-amino-3-(2-methoxy-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(2-methoxy-phenyl)-propionylamino)-thiazole-4-carboxylic acid methyl ester was prepared as described in example 3 except that (S)-2-tert-butoxycarbonylamino-3-(2-methoxy-phenyl)-propionic acid was used in place of (S)-2-tert-butoxycarbonylamino-3-phenyl-propionic acid in step 3.

HRMS: Obs. Mass, 547.1260. Calcd. Mass, 547.1258 (M+H).

2-[(S)-2-[(R)-4-(2,3-Dihydro-benzo[1,4]dioxin-6-yl)-2,5-dioxo-imidazolidin-1-yl]-3-(3-fluoro-phenyl)-propionylamino]-thiazole-4-carboxylic acid methyl ester

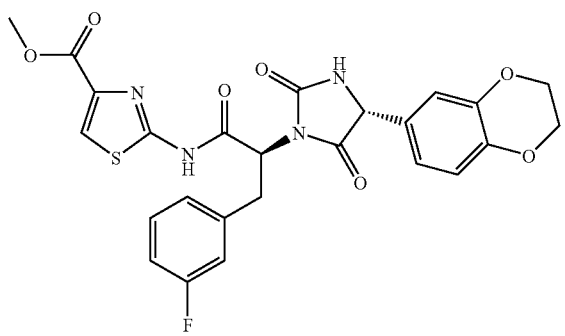

Prepared as described in example 10 except that (2R)-tert-butoxycarbonylamino-(2,3-dihydro-benzo[1,4]dioxin-6-yl)-acetic acid and 2-((S)-2-amino-3-(3-fluoro-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(3-fluoro-phenyl)-propionylamino)-thiazole-4-carboxylic acid methyl ester was prepared as described in example 3 except that (S)-2-tert-butoxycarbonylamino-3-(3-fluoro-phenyl)-propionic acid was used in place of (S)-2-tert-butoxycarbonylamino-3-phenyl-propionic acid in step 3.

HRMS: Obs. Mass, 541.1186. Calcd. Mass, 541.1188 (M+H).

2-{3-(3,4-Difluoro-phenyl)-(S)-2-[(R)4-(2,3-dihydro-benzo[1,4]dioxin-6-yl)-2,5-dioxo-imidazolidin-1-yl]-propionylamino}-thiazole-4-carboxylic acid methyl ester

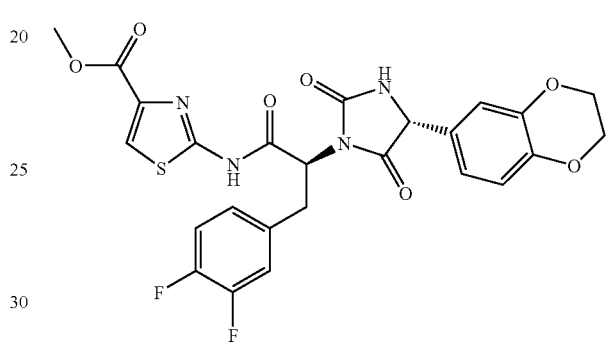

Prepared as described in example 10 except that (2R)-tert-butoxycarbonylamino-(2,3-dihydro-benzo[1,4]dioxin-6-yl)-acetic acid and 2-((S)-2-amino-3-(3,4-difluoro-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(3,4-difluoro-phenyl)-propionylamino)-thiazole-4-carboxylic acid methyl ester was prepared as described in example 3 except that (S)-2-tert-butoxycarbonylamino-3-(3,4-difluoro-phenyl)-propionic acid was used in place of (S)-2-tert-butoxycarbonylamino-3-phenyl-propionic acid in step 3.

HRMS: Obs. Mass, 559.1088. Calcd. Mass, 559.1094 (M+H).

2-((S)-2-{(R)-4-[4-(2-Hydroxy-ethoxy)-phenyl]-2,5-dioxo-imidazolidin-1-yl}-3-phenyl-propionylamino)-thiazole-4-carboxylic acid methyl ester

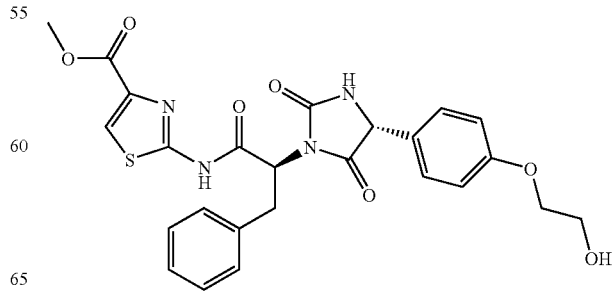

Prepared as described in example 10 except that (R)—N-(tert-butyloxycarbonyl)-4-(2-hydroxyethoxy)-phenylglycine was used in place of (R)-tert-butoxycarbonylaminophenylacetic acid in step 1.

HRMS: Obs. Mass, 525.1437. Calcd. Mass, 525.1439 (M+H).

2-{(S)-2-[(R)-4-(2,3-Dihydro-benzo[1,4]dioxin-6-yl)-2,5-dioxo-imidazolidin-1-yl]-3-thiophen-2-yl-propionylamino}-thiazole-4-carboxylic acid methyl ester

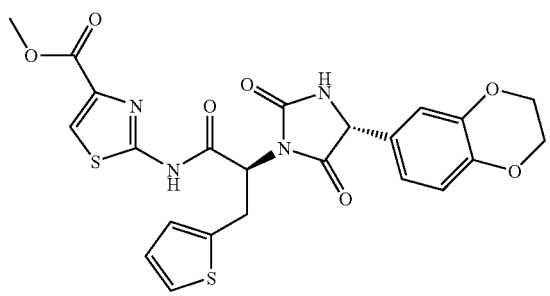

Prepared as described in example 10 except that (2R)-tert-butoxycarbonylamino-(2,3-dihydro-benzo[1,4]dioxin-6-yl)-acetic acid and 2-((S)-2-amino-3-(thien-2-yl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-(thien-2-yl)-propionylamino)-thiazole-4-carboxylic acid methyl ester was prepared as described in example 3 except that (S)-2-tert-butoxycarbonylamino-3-(thien-3-yl)-propionic acid was used in place of (S)-2-tert-butoxycarbonylamino-3-phenyl-propionic acid in step 3.

HRMS: Obs. Mass, 529.0847. Calcd. Mass, 529.0846 (M+H).

2-{(S)-2-[(R)-4-(4-Methoxy-phenyl)-2,5-dioxo-imidazolidin-1-yl]-3-thiazol-4-yl-propionylamino}-thiazole-4-carboxylic acid methyl ester

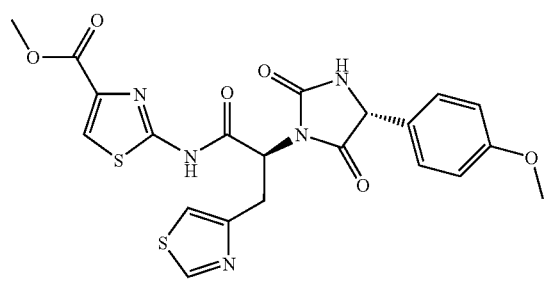

Prepared as described in example 10 except that (R)—N-(tert-butyloxycarbonyl)-4-methyoxyphenylglycine and 2-((S)-2-amino-3-thiazol-4-yl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-thiazol-4-yl-propionylamino)-thiazole-4-carboxylic acid methyl ester was prepared as described in example 3 except that (S)-2-tert-butoxycarbonylamino-3-thiazol-4-yl-propionic acid was used in place of (S)-2-tert-butoxycarbonylamino-3-phenyl-propionic acid in step 3.

HRMS: Obs. Mass, 502.0853. Calcd. Mass, 502.0850 (M+H).

2-{(S)-2-[(R)-4-(4-Methoxy-phenyl)-2,5-dioxo-imidazolidin-1-yl]-3-thiazol-2-yl-propionylamino}-thiazole-4-carboxylic acid methyl ester

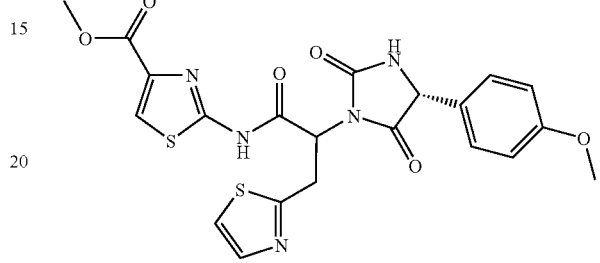

Prepared as described in example 10 except that (R)—N-(tert-butyloxycarbonyl)-4-methyoxyphenylglycine and 2-(2-amino-3-thiazol-2-yl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-thiazol-2-yl-propionylamino)-thiazole-4-carboxylic acid methyl ester was prepared as described in example 3 except that (S)-2-tert-butoxycarbonylamino-3-thiazol-2-yl-propionic acid was used in place of (S)-2-tert-butoxycarbonylamino-3-phenyl-propionic acid in step 3.

HRMS: Obs. Mass, 502.0857. Calcd. Mass, 502.0850 (M+H).

2-{(S)-2-[(R)-4-(2,3-Dihydro-benzo[1,4]dioxin-6-yl)-2,5-dioxo-imidazolidin-1-yl]-3-thiazol-4-yl-propionylamino)thiazole-4-carboxylic acid methyl ester

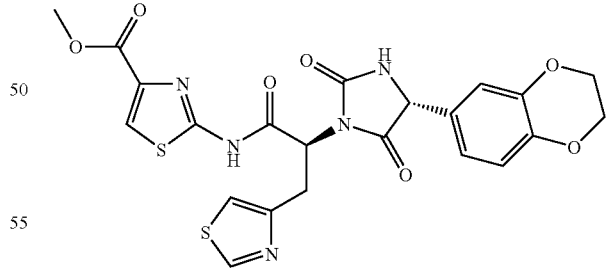

Prepared as described in example 10 except that (2R)-tert-butoxycarbonylamino-(2,3-dihydro-benzo[1,4]dioxin-6-yl)-acetic acid and 2-((S)-2-amino-3-thiazol-4-yl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-thiazol-4-yl-propionylamino)-thiazole-4-carboxylic acid methyl ester was prepared as described in example 3 except that (S)-2-tert-butoxycarbonylamino-3-thiazol-4-yl)-propionic acid was used in place of (S)-2-tert-butoxycarbonylamino-3-phenyl-propionic acid in step 3.

HRMS: Obs. Mass, 530.0807. Calcd. Mass, 530.0799 (M+H).

2-{(S)-2-[(R)-4-(2,3-Dihydro-benzo[1,4]dioxin-6-yl)-2,5-dioxo-imidazolidin-1-yl]-3-thiophen-3-yl-propionylamino}-thiazole-4-carboxylic acid methyl ester

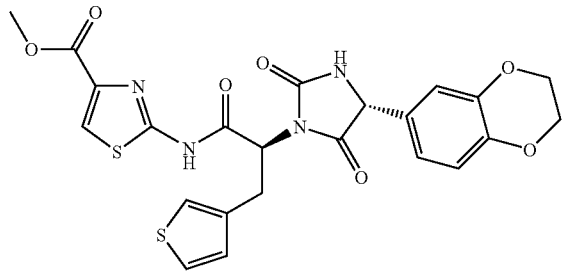

Prepared as described in example 10 except that (2R)-tert-butoxycarbonylamino-(2,3-dihydro-benzo[1,4]dioxin-6-yl)-acetic acid and 2-((S)-2-amino-3-thien-3-yl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-thien-3-yl-propionylamino)-thiazole-4-carboxylic acid methyl ester was prepared as described in example 3 except that (S)-2-tert-butoxycarbonylamino-3-thien-3-yl)-propionic acid was used in place of (S)-2-tert-butoxycarbonylamino-3-phenyl-propionic acid in step 3.

HRMS: Obs. Mass, 529.0846. Calcd. Mass, 529.0846 (M+H).

2-{(S)-2-[(R)-4-(2,3-Dihydro-benzo[1,4]dioxin-6-yl)-2,5-dioxo-imidazolidin-1-yl]-3-pyrazol-1-yl-propionylamino}-thiazole-4-carboxylic acid methyl ester

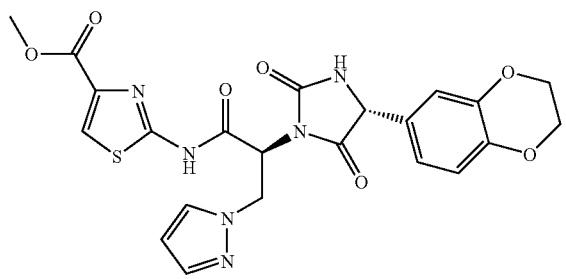

Prepared as described in example 10 except that (2R)-tert-butoxycarbonylamino-(2,3-dihydro-benzo[1,4]dioxin-6-yl)-acetic acid and 2-((S)-2-amino-3-pyrazol-1-yl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((S)-2-Amino-3-pyrazol-1-yl-propionylamino)-thiazole-4-carboxylic acid methyl ester was prepared as described in example 3 except that (S)-2-tert-butoxycarbonylamino-3-pyrazol-1-yl)-propionic acid was used in place of (S)-2-tert-butoxycarbonylamino-3-phenyl-propionic acid in step 3.

LRMS: Obs. Mass, 513. (M+H). Calcd. Mass, 513.1192 (M+H).

2-{(R)-2-[(R)-4-(4-Methoxy-phenyl)-2,5-dioxo-imidazolidin-1-yl]-3-phenyl-propionylamino}-thiazole-4-carboxylic acid methyl ester

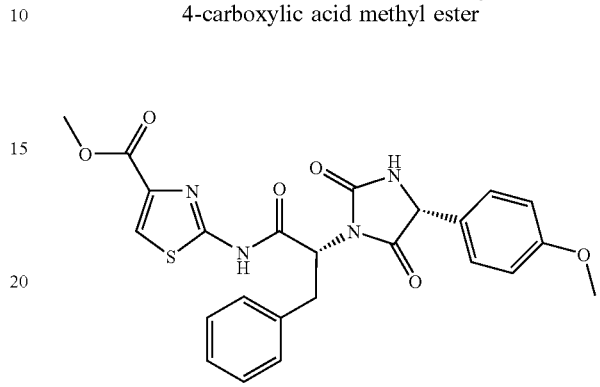

Prepared as described in example 10 except that (R)—N-(tert-butyloxycarbonyl)-4-methyoxyphenylglycine and 2-((R)-2-amino-3-phenyl-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. 2-((R)-2-Amino-3-phenyl-propionylamino)-thiazole-4-carboxylic acid methyl ester was prepared as described in example 3 except that (R)-2-tert-butoxycarbonylamino-3-phenyl-propionic acid was used in place of (S)-2-tert-butoxycarbonylamino-3-phenyl-propionic acid in step 3.

HRMS: Obs. Mass, 495.1332. Calcd. Mass, 495.1333 (M+H).

2-{(S)-2-[(S)-4-(4-Methoxy-phenyl)-2,5-dioxo-imidazolidin-1-yl]-3-phenyl-propionylamino}-thiazole-4-carboxylic acid methyl ester

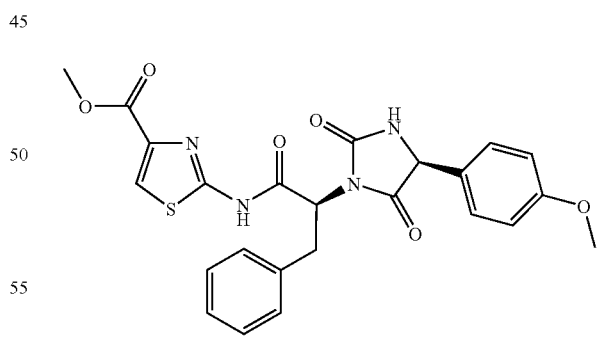

Prepared as described in example 10 except that (S)—N-(tert-butyloxycarbonyl)-4-methyoxyphenylglycine was used in place of (R)-tert-butoxycarbonylamino-phenylacetic acid in step 1. (S)—N-(tert-Butyloxycarbonyl)-4-methyoxyphenylglycine was prepared as described for (R)—N-(tert-butyloxycarbonyl)-4-methyoxyphenylglycine except that (S)—N-(tert-butoxycarbonyl)-4-hydroxyphenylglycine was used in place of (R)—N-(tert-butyloxycarbonyl)-4-hydroxyphenylglycine.

HRMS: Obs. Mass, 495.1340. Calcd. Mass, 495.1333 (M+H).

2-((S)-2-{(R)-4-[4-(2-Methoxy-ethoxy)-phenyl]-2,5-dioxo-imidazolidin-1-yl}-3-phenyl-propionylamino)-thiazole-4-carboxylic acid methyl ester

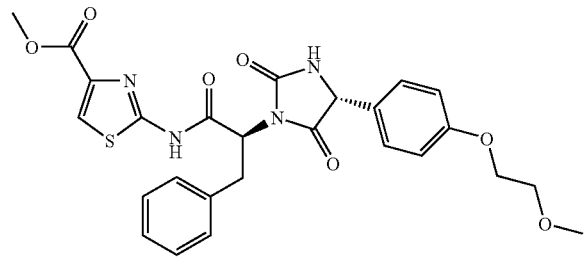

Prepared as described in example 10 except that (R)-tert-butoxycarbonylamino-{4-[2-(methoxy)-ethoxy]-phenyl}-acetic acid was used in place of (R) tert-butoxycarbonylamino-phenylacetic acid in step 1.

2-((S)-2-{(R)-4-[4-(2-Methoxy-ethoxy)-phenyl]-2,5-dioxo-imidazolidin-1-yl}-3-phenyl-propionylamino)-thiazole-4-carboxylic acid methyl ester was a 85:15 mixture of R and S isomers at the 2,5-dioxo-imidazolidine chiral center.

(R)-tert-Butoxycarbonylamino-{4-[2-(methoxy)-ethoxy]-phenyl}-acetic acid was prepared as follows.

To a mechanically stirring solution of (R)-tert-butoxycarbonylamino-(4-hydoxy-phenyl)-acetic acid (37.41 g, 140 mmol) (pepared according to the procedure of Salituro, G. M.; Townsend, C. A. *J. Am. Chem. Soc.* 1990, 112, 760) in N,N-dimethylformamide (750 mL) cooled in a dry ice/acetone bath was added sodium hydride (60% suspension in mineral oil) (12.32 g, 308 mmol) in small portions. The mixture was stirred while cooling in a dry ice/acetone bath for 30 minutes, then a solution of bromoethyl methyl ether (19.73 mL, 210 mmol) in N,N-dimethylformamide (200 mL) was added dropwise. The reaction mixture was allowed to warm to room temperature and stirred for 24 hours. The reaction mixture was diluted with ice-water and extracted with ethyl acetate. The aqueous layer was cooled in an ice bath and acidified using concentrated aqueous hydrochloric acid to pH=1. The resulting mixture was extracted with ethyl acetate (3×), the organic extracts were combined, washed with water, brine and dried over sodium sulfate. Evaporation of the solvents gave (R)-tert-butoxycarbonylamino-{4-[2-(methoxy)-ethoxy]-phenyl}-acetic acid as a white solid (35.7 g, 78%).

(R)-tert-butoxycarbonylamino-{4-[2-(methoxy)-ethoxy]-phenyl}-acetic acid (0.6 g, 1.84 mmol), 2-chloro-4,6-dimethoxy-1,3,5-triazine (0.32 g, 1.84 mmol) and N-methylmorpholine (0.19 g, 1.84 mmol) in anhydrous tetrahydrofuran (20 mL) were stirred at room temperature for 4 hours. Then a solution of 2-((S)-2-amino-3-phenyl-propionylamino)-thiazole-4-carboxylic acid methyl ester (0.56 g, 1.84 mmol) in tetrahydrofuran (10 mL) was added. The reaction mixture was stirred at room temperature for 20 hours. The mixture was filtered though a short pad of silica gel and the residual material eluted from the silica gel with ethyl acetate. The filtrate was concentrated. The residue was purified by chromatography over silica gel eluted with 1:1 ethyl acetate/hexanes to give 2-((S)-2-{2-tert-butoxycarbonylamino-2-[4-(2-methoxy-ethoxy)-phenyl]-acetylamino}-3-phenyl-propionylamino)-thiazole-4-carboxylic acid methyl ester as a mixture of two epimers (R/S=85:15) (0.21 g, (3) 2-((S)-2-{2-tert-Butoxycarbonylamino-2-[4-(2-methoxy-ethoxy)-phenyl]-acetylamino}-3-phenyl-propionylamino)-thiazole-4-carboxylic acid methyl ester (a mixture of two epimers, R/S=85:15) (0.21 g, 0.343 mmol) was dissolved into dry dichloromethane (20 mL) and trifluoroacetic acid (2 mL, 26 mmol) was added. The reaction mixture was stirred at room temperature for 1 hour. The mixture was concentrated to dryness. The residue was cooled in an ice bath, then neutralized with saturated aqueous sodium bicarbonate solution. The mixture was extracted with ethyl acetate. The organic layer was separated, dried over sodium sulfate, and concentrated to give crude 2-((S)-2A2-amino-2-[4-(2-methoxy-ethoxy)-phenyl]-acetylamino}-3-phenyl-propionylamino)-thiazole-4-carboxylic acid methyl ester as a white foam (a mixture of two epimers, R/S=85:15) (0.16 g, 91%).

To a solution of 2-((S)-2-{2-amino-2-[4-(2-methoxy-ethoxy)-phenyl]-acetylamino}-3-phenyl-propionylamino)-thiazole-4-carboxylic acid methyl ester (a mixture of two epimers R/S=85:15) (0.16 g , 0.31 mmol) and diisopropylethylamine (0.31 mL, 1.78 mmol) in dichloromethane (20 mL) was added to a solution of diphosgene (0.03 μL, 0.25 mmol) in dichloromethane (30 mL) over a period of 10 minute at −10° C. The mixture was stirred at −10° C. for 15 minutes Water was added to quench the reaction, then the mixture was extracted with ethyl acetate. The organic layer was separated, washed with water, brine, dried over sodium sulfate and concentrated. The residue was purified by chromatography over silica gel eluted with ethyl acetate to give 2-((S)-2-{4-[4-(2-methoxy-ethoxy)-phenyl]-2,5-dioxo-imidazolidin-1-yl}-3-phenyl-propionylamino)-thiazole-4-carboxylic acid methyl ester as a white solid (a mixture of two epimers R/S=85:15) (0.075 g, 87%).

HRMS: Obs. Mass, 513.1245. Calcd. Mass, 513.1239 (M+H).

2-[2-[(R)-4-(4-Methoxy-phenyl)-2,5-dioxo-imidazolidin-1-yl]-3-(3-nitro-phenyl)-propionylamino]-thiazole-4-carboxylic acid methyl ester

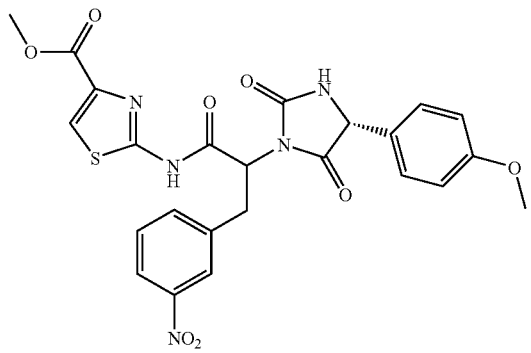

Prepared as described in example 10 except that (R)—N-(tert-butyloxycarbonyl)-4-methyoxyphenylglycine was used in place of (R)-tert-butoxycarbonylamino-phenylacetic acid and 2-[2-amino-3-(3-nitro-phenyl)-propionylamino]-thiazole-4-carboxylic acid methyl ester was used in place of 2-((S)-2-amino-3-phenyl-propionylamino)-thiazole-4-carboxylic acid methyl ester in step 1. 2-[2-Amino-3-(3-nitrophenyl)-propionylamino]-thiazole-4-carboxylic acid methyl ester was prepared as described in example 3 except that 2-tert-butoxycarbonylamino-3-(3-nitro-phenyl)-propionic acid was used in place of (S)-2-tert-butoxycarbonylamino-3-phenyl-propionic acid in step 3. 2-tert-Butoxycarbonylamino-3-(3-nitro-phenyl)-propionic acid was prepared as follows.

To a solution of (benzhydrylidene-amino)-acetic acid ethyl ester (2.84 g, 10.4 mmol) in anhydrous tetrahydrofuran (15 mL) at −78° C. under an atmosphere of argon was added a 1 M solution of potassium tert-butoxide in tetrahydrofuran (11 mL, 11 mmol) to form a red/orange solution. After stirring at −78° C. for 15 minutes a solution of 1-bromomethyl-3-nitro-benzene (2.14 g, 9.7 mmol) in tetrahydrofuran (20 mL) was added and the reaction mixture left to warm slowly to ambient temperature and stir for 16 hours. To the reaction mixture was added saturated aqueous ammonium chloride (20 mL), the mixture was poured into water (100 mL), diluted with brine (50 mL) and extracted with ethyl acetate (3×50 mL). The combined organic extracts were washed with brine (2×50 mL), dried over sodium sulfate and concentrated in vacuo to give crude 2-(benzhydrylidene-amino)-3-(3-nitro-phenyl)-propionic acid ethyl ester as a red/brown viscous oil which was used without further purification (4.1 g, ≈100%).

To a solution of crude 2-(benzhydrylidene-amino)-3-(3-nitro-phenyl)-propionic acid ethyl ester (4.1 g, ≈10.2 mmol) in ether (100 mL) was added 1M aqueous hydrochloric acid and the mixture stirred vigorously at ambient temperature for 4 hours. The layers were separated and the organic layer extracted with 1M aqueous hydrochloric acid (3×50 mL). The combined aqueous layers were cautiously adjusted to pH=8 with solid potassium carbonate and then extracted with ethyl acetate (3×100 mL). The combined organic extracts were washed with brine (150 mL), dried over sodium sulfate and concentrated in vacuo to give crude 2-amino-3-(3-nitro-phenyl)-propionic acid ethyl ester. The crude amine was dissolved in acetonitrile (100 mL), di-tert-butyldicarbonate (2.4 g, mmol) added and the mixture stirred at ambient temperature for 16 hours. The reaction mixture was poured into water (500 mL), extracted with ether (3×100 mL), the combined organic extracts were washed with 0.1M aqueous hydrochloric acid (100 mL), saturated aqueous sodium bicarbonate (100 mL), brine (100 mL), dried over sodium sulfate and concentrated in vacuo to give crude 2-tert-butoxycarbonylamino-3-(3-nitro-phenyl)-propionic acid ethyl ester as an orange/yellow viscous oil (3.35 g, ≈97%).

To a solution of crude 2-tert-butoxycarbonylamino-3-(3-nitro-phenyl)-propionic acid ethyl ester (1.00 g , ≈2.96 mmol) in tetrahydrofuran (10 mL) was added 3M aqueous lithium hydroxide solution (3 mL, 9 mmol) and the mixture was stirred at ambient temperature overnight. The reaction mixture was concentrated to dryness, the residue taken up in water (20 mL) and extracted with ether (2×10 mL). The aqueous layer was filtered through Celite®, cooled in ice and adjusted to pH=2 with 0.1M aqueous hydrochloric acid. The mixture was then extracted with dichloromethane (3×15 mL), dried over sodium sulfate and concetrated in vacuo to give crude 2-tert-butoxycarbonylamino-3-(3-nitro-phenyl)-propionic acid as a pale yellow solid which was used without further purification (0.63 g, ≈69%).

HRMS: Obs. Mass, 540.1185. Calcd. Mass, 540.1184 (M+H).

2-[(S)-2-[(R)-4-(4-Methoxy-phenyl)-2,5-dioxo-imidazolidin-1-yl]-3-(4-nitro-phenyl)-propionylamino]-thiazole-4-carboxylic acid methyl ester

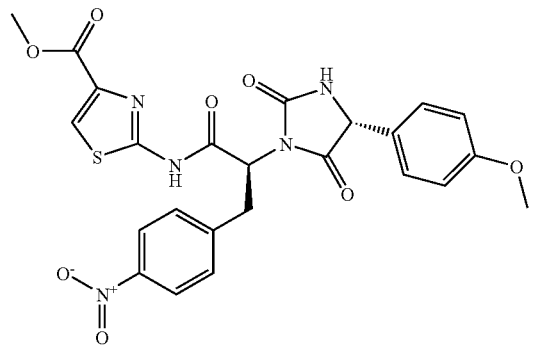

Prepared as described in example 10 except that (R)—N-(tert-butyloxycarbonyl)-4-methyoxyphenylglycine was used in place of (R)-tert-butoxycarbonylamino-phenylacetic acid and 2-[(S)-2-amino-3-(4-nitro-phenyl)-propionylamino]-thiazole-4-carboxylic acid methyl ester was used in place of 2-((S)-2-amino-3-phenyl-propionylamino)-thiazole-4-carboxylic acid methyl ester in step 1. 2-[(S)-2-Amino-3-(4-nitro-phenyl)-propionylamino]-thiazole-4-carboxylic acid methyl ester was prepared as described in example 3 except that (S)-2-tert-butoxycarbonylamino-3-(4-nitro-phenyl)-propionic acid was used in place of (S)-2-tert-butoxycarbonylamino-3-phenyl-propionic acid in step 3.

HRMS: Obs. Mass, 540.1184. Calcd. Mass, 540.1184 (M+H).

2-{(S)-3-(4-Amino-phenyl)-2-[(R)-4-(4-methoxy-phenyl)-2,5-dioxo-imidazolidin-1-yl]-propionylamino}-thiazole-4-carboxylic acid methyl ester

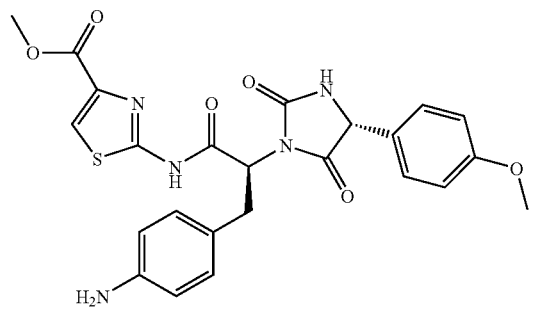

To a stirred solution of 2-[(S)-2-[(R)-4-(4-methoxy-phenyl)-2,5-dioxo-imidazolidin-1-yl]-3-(4-nitro-phenyl)-propionylamino]-thiazole-4-carboxylic acid methyl ester (0.32 g, 0.59 mmol) in methanol (125 mL), tetrahydrofuran (25 mL) and N,N-dimethylformamide (3 mL) was added a solution of ammonium chloride (0.63 g, 11.8 mmol) in water (3 mL) followed by zinc dust (<10 μM particle size) (0.388 g, 5.94 mmol). After 15 minutes the reaction mixture was filtered through a pad of Celite® and washed through with methanol. The filtrate was concentrated in vacuo and the residue partitioned between dichloromethane and water. The organic solution was washed with saturated aqueous sodium bicarbonate, water, brine, dried over sodium sulfate and concentrated in vacuo to a yellow solid (0.35 g). Purification by chromatography using silica eluted with 90:10:6:5 chloroform/water/acetic acid/methanol followed by drying in vacuo gave 2-{(S)-3-(4-amino-phenyl)-2-[(R)-4-(4-methoxy-phenyl)-2,5-dioxo-imidazolidin-1-yl]-propionylamino}-thiazole-4-carboxylic acid methyl ester as a brown solid (66 mg, 22%).

HRMS: Obs. Mass, 510.1441. Calcd. Mass, 510.1442 (M+H).

2-{(S)-3-(4-Dimethylamino-phenyl)-2-[(R)-4-(4-methoxy-phenyl)-2,5-dioxo-imidazolidin-1-yl]-propionylamino}-thiazole-4-carboxylic acid methyl ester

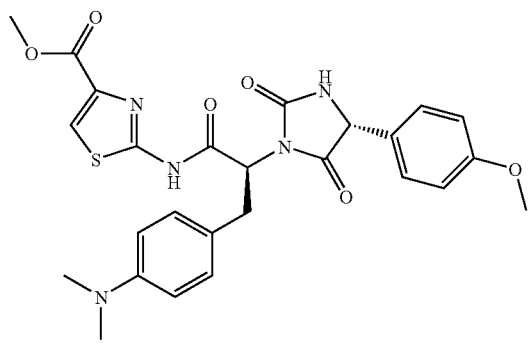

To a solution of 2-[(S)-2-[(R)-4-(4-methoxy-phenyl)-2,5-dioxo-imidazolidin-1-yl]-3-(4-nitro-phenyl)-propionylamino]-thiazole-4-carboxylic acid methyl ester (53.9 mg, 0.1 mmol) in tetrahydrofuran (10 mL) was added sodium acetate (60 mg, 0.44 mmol), 37% w/w aqueous formaldehyde solution (0.033 mL, 0.44 mmol) and 10% palladium on carbon (30 mg) and the mixture shaken under an atmosphere of hydrogen at 50 psi pressure in a Parr apparatus for 72 hours. The reaction mixture was filtered through a pad of Celite® and washed through with additional tetrahydrofuran. The filtrate was concentrated in vacuo, the residue was dissolved in dichloromethane, washed with water, saturated aqueous sodium bicarbonate, dried with sodium sulfate and concentrated in vacuo to give the crude product as a yellow solid. Purification by reverse phase HPLC using a C18 stationary phase gradient eluted from 10% up to 90% acetonitrile in water gave 2-(S)-3-(4-dimethylamino-phenyl)-2-[(R)-4-(4-methoxy-phenyl)-2,5-dioxo-imidazolidin-1-yl]-propionylamino}-thiazole-4-carboxylic acid methyl ester as a colorless solid (12 mg, 22%).

HRMS: Obs. Mass, 538.1757. Calcd. Mass, 538.1755 (M+H).

2-[(S)-2-{4-[4-(2-Methoxy-ethoxy)-phenyl]-2,5-dioxo-imidazolidin-1-yl}-3-(2-methoxy-phenyl)-propionylamino]-thiazole-4-carboxylic acid methyl ester

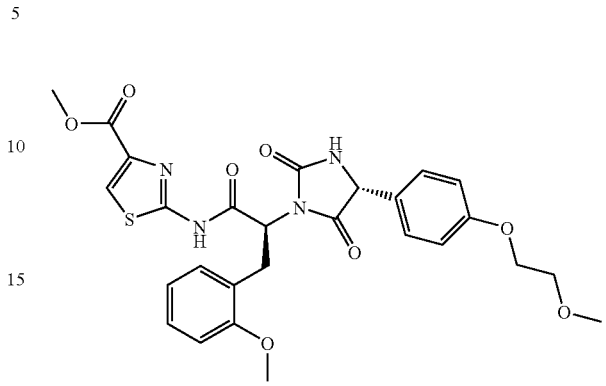

Prepared as described in example 10 except that (R)-tert-butoxycarbonylamino-{4-[2-(methoxy)-ethoxy]-phenyl}-acetic acid was used in place of (R)-tert-butoxycarbonylamino-phenylacetic acid and 2-[(S)-2-amino-3-(2-methoxy-phenyl)-propionylamino]-thiazole-4-carboxylic acid methyl ester was used in place of 2-((S)-2-amino-3-phenyl-propionylamino)-thiazole-4-carboxylic acid methyl ester in step 1. 2-[(S)-2-Amino-3-(2-methoxy-phenyl)-propionylamino]-thiazole-4-carboxylic acid methyl ester was prepared as described in example 3 except that (S)-2-tert-butoxycarbonylamino-3-(2-methoxy-phenyl)-propionic acid was used in place of (S)-2-tert-butoxycarbonylamino-3-phenyl-propionic acid in step 3. (R)-tert-Butoxycarbonylamino-{4-[2-(methoxy)-ethoxy]-phenyl}-acetic acid was prepared as described in example 11(r).

HRMS: Obs. Mass, 569.1704. Calcd. Mass, 569.1701 (M+H).

EXAMPLE 12

In a Manner Similar to that Described in Example 10, the Following Compound was Prepared 2-{(S)-3-(2-Cyano-phenyl)-2-[(R)-4-(4-methoxy-phenyl)-2,5-dioxo-imidazolidin-1-yl]-propionylamino}-thiazole-4-carboxylic acid methyl ester

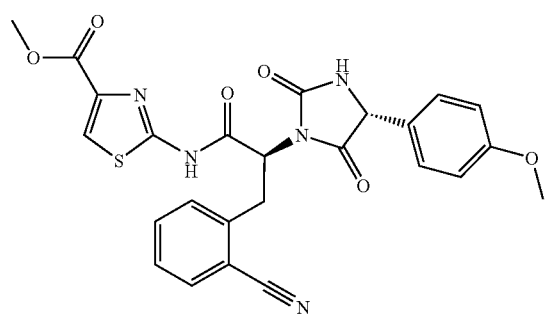

Prepared as described in example 10 except that (R)—N-(tert-butyloxycarbonyl)-4-methyoxyphenylglycine and 2-((S)-2-amino-3-(2-cyano-phenyl)-propionylamino)-thiazole-4-carboxylic acid methyl ester were used in place of (R)-tert-butoxycarbonylamino-phenylacetic acid and 2-((S)-

2-amino-3-phenyl-propionylamino)-thiazole-4-carboxylic acid methyl ester respectively in step 1. 2-((S)-2-Amino-3-(2-cyano-phenyl)-propionylamino)-thiazole-4-carboxylic acid methyl ester was prepared as described below.

2-{(S)-3-(2-Cyano-phenyl)-2-[(R)-4-(4-methoxy-phenyl)-2,5-dioxo-imidazolidin-1-yl]-propionylamino}-thiazole-4-carboxylic acid methyl ester was obtained as a 85:15 mixture of R and S isomers at the 2,5-dioxo-imidazolidine chiral center.

(S)-2-tert-Butoxycarbonylamino-3-(2-cyano-phenyl)-propionic acid (2.5 g, 8.6 mmol) and pyridine (0.68 g, 8.6 mmol) were dissolved in dichloromethane (50 mL) at 0° C. Cyanuric fluoride (1.74 mL, 12.9 mmol) was added dropwise. The mixture was stirred at 0° C. for 1 hour and then ice-water was added. The mixture was extracted with dichloromethane (2×). The organic extracts were washed with water, brine, and dried over sodium sulfate. Evaporation of the solvents gave crude [(S)-2-(2-cyano-phenyl)-1-fluorocarbonyl-ethyl]-carbamic acid tert-butyl ester as a yellow solid which was used without further purification in the next step (2.4 g).

[(S)-2-(2-Cyano-phenyl)-1-fluorocarbonyl-ethyl]-carbamic acid tert-butyl ester (2.4 g, 8.2 mmol) and 2-amino-thiazole-4-carboxylic acid methyl ester (1.24 g, 7.8 mmol) were dissolved in p-dioxane (40 mL). The mixture was heated in a sealed tube under microwave irradiation at 120° C. for 15 minutes The solution was concentrated, and the residue was purified by chromatography over silica gel eluted with 1:1 ethyl acetate/hexanes to give 2-[(S)-2-tert-butoxycarbonylamino-3-(2-cyano-phenyl)-propionylamino]-thiazole-4-carboxylic acid methyl ester as a white solid (3.2 g, 95%).

(3) 2-[(S)-2-tert-Butoxycarbonylamino-3-(2-cyano-phenyl)-propionylamino]-thiazole-4-carboxylic acid methyl ester (3.2 g, 7.4 mmol) was dissolved into dry dichloromethane (20 mL) and trifluoroacetic acid (25 mL, 325 mmol) was added. The reaction mixture was stirred at room temperature for 1 hour. The mixture was concentrated to dryness. The residue was cooled in an ice bath, then neutralized with saturated aqueous sodium bicarbonate solution. The mixture was extracted with ethyl acetate. The organic layer was separated, dried over sodium sulfate and concentrated to give crude 2-[(S)-2-amino-3-(2-cyano-phenyl)-propionylamino]-thiazole-4-carboxylic acid methyl ester as a pale yellow solid (2.1 g, 86%).

HRMS: Obs. Mass, 520.1289. Calcd. Mass, 520.1286 (M+H).

2-((S)-3-(2-Cyano-phenyl)-2-{4-[(R)-4-(2-methoxy-ethoxy)-phenyl]-2,5-dioxo-imidazolidin-1-yl}-propionylamino)-thiazole-4-carboxylic acid methyl ester

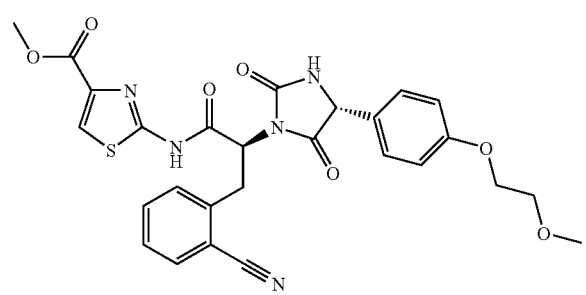

Prepared as described in example 10 except that (R)-tert-butoxycarbonylamino-{4-[2-(methoxy)-ethoxy]-phenyl}-acetic acid and 2-((S)-2-amino-3-(2-cyano-phenyl)-propionylamino)-thiazole-4-carboxylic acid methyl ester were used in place of (R)-tert-butoxycarbonylamino-phenylacetic acid and 2-((S)-2-amino-3-phenyl-propionylamino)-thiazole-4-carboxylic acid methyl ester respectively in step 1. (R)-tert-butoxycarbonylamino-{4-[2-(methoxy)-ethoxy]-phenyl}-acetic acid was prepared as described in example 11 (r). 2-((S)-2-Amino-3-(2-cyano-phenyl)-propionylamino)-thiazole-4-carboxylic acid methyl ester was prepared as described in example 12(a)

2-((S)-3-(2-Cyano-phenyl)-2-{4-[(R)4-(2-methoxy-ethoxy)-phenyl]-2,5-imidazolidin-1-yl}-propionylamino)-thiazole-4-carboxylic acid methyl ester was obtained as a 85:15 mixture of R and S isomers at the 2,5-dioxo-imidazolidine chiral center.

HRMS: Obs. Mass, 564.1549. Calcd. Mass, 564.1648 (M+H).

2-{(S)-2-[4-((R)-(4-Ethoxy-phenyl))-2,5-dioxo-imidazolidin-1-yl]-3-phenyl-propionylamino}-thiazole-4-carboxylic acid methyl ester

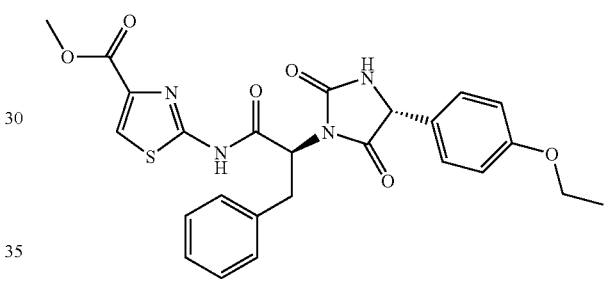

Prepared as described in example 10 except that (R)-tert-butoxycarbonylamino-(4-ethoxy-phenyl)-acetic acid was used in place of (R)-tert-butoxycarbonylamino-phenylacetic acid in step 1. (R)-tert-Butoxycarbonylamino-(4-ethoxy-phenyl)-acetic acid was prepared by the same method used to prepare (R)-tert-butoxycarbonylamino-(4-methoxy-phenyl)-acetic acid.

2-{(S)-2-[4-((R)-(4-Ethoxy-phenyl))-2,5-dioxo-imidazolidin-1-yl]-3-phenyl-propionylamino}-thiazole-4-carboxylic acid methyl ester was obtained as a 85:15 mixture of R and S isomers at the 2,5-dioxo-imidazolidine chiral center.

HRMS: Obs. Mass, 509.1496. Calcd. Mass, 509.1490 (M+H).

2-((S)-2-{(R)-4-[4-((R)-2,3-Dihydroxy-propoxy)-phenyl]-2,5-dioxo-imidazolidin-1-yl}-3-phenyl-propionylamino)-thiazole-4-carboxylic acid methyl ester

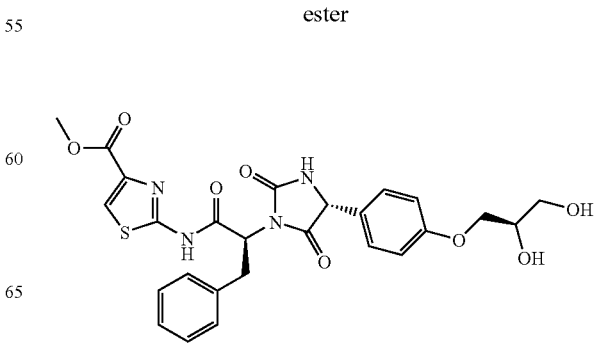

((S)-2,2-Dimethyl-[1,3]dioxolan-4-yl)-methanol (2.0 g, 15.13 mmol) and triethylamine (2.53 ml, 18.16 mmol) were dissolved in dichloromethane (60 mL) followed by the addition of methanesulfonyl chloride (1.35 ml, 17.40 mmol) at 0° C. The reaction was warmed to ambinet temperature, stirred overnight, and then diluted with water. The organic layer was washed with saturated aqueous sodium bicarbonate solution, brine and dried over sodium sulfate. Removal of solvents gave methanesulfonic acid (R)-2,2-dimethyl-[1,3]dioxolan-4-ylmethyl ester as an oil (3.2 g, 100%).

(R)-tert-Butoxycarbonylamino-(4-hydroxy-phenyl)-acetic acid (200 mg, 0.75 mmol) was dissolved in anhydrous N,N-dimethylformamide (4 mL) followed by the addition of sodium hydride (60% dispersion in mineral oil) (63 mg, 1.57 mmol) at room temperature. The reaction was stirred for 30 minutes followed by the dropwise addition of methanesulfonic acid (R)-2,2-dimethyl-[1,3]dioxolan4-ylmethyl ester (189 mg, 0.90 mmol) dissolved in N,N-dimethylformamide (2 mL) at room temperature. The mixture was heated to 100° C. overnight. The reaction was cooled to room temperature, acidified to pH=4 with 0.2 M aqueous hydrochloric acid, poured into ethyl acetate and diluted with water. The organic layer was washed with brine and dried over sodium sulfate. Removal of solvents gave (R)-tert-butoxycarbonylamino-[4-((S)-2,2-dimethyl-[1,3]dioxolan4-ylmethoxy)-phenyl]-acetic acid as a foam (280 mg, 98%).

(R)-tert-Butoxycarbonylamino-[4-((S)-2,2-dimethyl-[1,3]dioxolan-4-ylmethoxy)-phenyl]-acetic acid (280 mg, 0.73 mmol), 2-((S)-2-amino-3-phenyl-propionylamino)-thiazole-4-carboxylic acid methyl ester (203 mg, 0.66 mmol) (prepared as described in example 10, step 1), 1-[3-(dimethylamino)propyl]-3-ethylcarbodiimide hydrochloride (191 mg, 1.0 mmol) and 1-hydroxybenzotriazole hydrate (135 mg, 1.0 mmol) were combined in dichloromethane (5 mL) and stirred overnight at room temperature. The resulting solution was poured into ethyl acetate and washed with 0.2 M aqueous hydrochloric acid, water, brine and dried over magnesium sulfate. The solvents were removed and the crude was purified by chromatography over silica gel gradient eluted between 40% and 50% v/v ethyl acetate in hexane to give 2-((S)-2-{(R)-2-tert-butoxycarbonylamino-2-[4-((S)-2,2-dimethyl-[1,3]dioxolan4-ylmethoxy)-phenyl]-acetylamino}-3-phenyl-propionylamino)-thiazole-4-carboxylic acid methyl ester as a foam (170 mg, 38%).

To a solution of 2-((S)-2-{(R)-2-tert-butoxycarbonylamino-2-[4-((S)-2,2-dimethyl-[1,3]dioxolan4-ylmethoxy)-phenyl]-acetylamino}-3-phenyl-propionylamino)-thiazole-4-carboxylic acid methyl ester (170 mg, 0.25 mmol) in dichloromethane (2.0 mL) was added trifluoroacetic acid (0.5 mL, 6.5 mmol) at 0° C. The reaction was warmed to room temperature and stirred for 4 hours. The solvent was removed under vacuum and the residue was partitioned between ethyl acetate and saturated aqueous sodium bicarbonate solution. The aqueous layer was extracted with ethyl acetate and the extracts were combined, washed with brine and dried over sodium sulfate to give 2-((S)-2-{(R)-2-amino-2-[4-((R)-2,3-dihydroxy-propoxy)-phenyl]-acetylamino}-3-phenyl-propionylamino)-thiazole-4-carboxylic acid methyl ester as a foam (120 mg, 90%).

Chloro-trimethyl-silane (0.086 ml, 0.68 mmol) was added to 2-((S)-2-{(R)-2-amino-2-[4-((R)-2,3-dihydroxy-propoxy)-phenyl]-acetylamino}-3-phenyl-propionylamino)-thiazole-4-carboxylic acid methyl ester (120 mg, 0.23 mmol) in tetrahydrofuran (5 mL) containing triethylamine (0.10 ml, 0.73 mmol) at room temperature and stirred for 3 hours. The mixture was diluted with water and extracted with ethyl acetate. The organic extracts were washed with water, brine and dried over magnesium sulfate. Removal of solvents gave 2-((S)-2-{(R)-2-amino-2-[4-((S)-2,3-bis-trimethylsilanyloxy-propoxy)-phenyl]-acetylamino}-3-phenyl-propionylamino)-thiazole-4-carboxylic acid methyl ester as an oil (100 mg, 66%).

(6) 2-((S)-2-{(R)-2-Amino-2-[4-((S)-2,3-bis-trimethylsilanyloxy-propoxy)-phenyl]-acetylamino}-3-phenyl-propionylamino)-thiazole-4-carboxylic acid methyl ester (100 mg, 0.15 mmol) and diisoproylethylamine (0.078 ml, 0.45 mmol) in dichloromethane (2 mL) were added to a solution of diphosgene (0.0143 ml, 0.12 mmol) in dichloromethane (2 mL) over 10 minute at 0° C. The mixture was stirred at 0° C. for 20 minute, diluted with ethyl acetate, washed with saturated sodium bicarbonate, brine and dried over sodium sulfate. Evaporation of solvents gave an oil which was dissolved in tetrahydrofuran (2 mL), treated with 1 N aqueous hydrochloric acid (0.45 ml, 0.45 mmol) and stirred for 3 hours. The reaction was neutralized with saturated aqueous sodium bicarbonate and extracted with ethyl acetate. The organic extracts were washed with brine and dried over magnesium sulfate. The crude product was purified by chromatography over silica gel gradient eluted with 100% ethyl acetate up to 3% v/v methanol in ethyl acetate to give 2-((S)-2-{(R)-4-[4-((R)-2,3-dihydroxy-propoxy)-phenyl]-2,5-dioxo-imidazolidin-1-yl}-3-phenyl-propionylamino)-thiazole-4-carboxylic acid methyl ester as a solid (35 mg, 42%).

HRMS: Obs. Mass, 555.1545. Calcd. Mass, 555.1544 (M+H).

EXAMPLE 13

2-{(S)-2-[4-(4-Methoxy-3-methyl-phenyl)-2,5-dioxo-imidazolidin-1-yl]-3-phenyl-propionylamino}-thiazole-4-carboxylic acid methyl ester

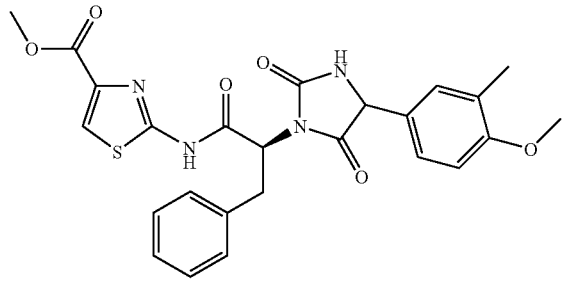

To a solution of benzyloxycarbonylamino-hydroxy-acetic acid (5.9 g, 26.2 mmol) (prepared according to the procedure of E. H. W. Bohme, et al., *J. Med. Chem*, 1980, 23, 405-412) and 2-methylanisole (3.2 g, 26.2 mmol) in acetic acid (150 mL) was added concentrated sulfuric acid (15 mL). The mixture was stirred at room temperature for 1 hour, then poured into ice/water and extracted with ethyl acetate (2×200 mL). The combined organic extracts were dried over sodium sulfate and concentrated to give an oily residue. The residue was triturated in hexanes, the precipitate formed was collected by filtration and dried overnight to give crude benzyloxycarbonylamino-(4-methoxy-3-methyl-phenyl)-acetic acid as a white solid (8.6 g, 100%).

To a solution of 2-((S)-2-amino-3-phenyl-propionylamino)-thiazole-4-carboxylic acid methyl ester (0.93 g, 3.04 mmol), benzyloxycarbonylamino-(4-methoxy-3-methyl-phenyl)-acetic acid (1.0 g, 3.04 mmol), diisopropylethylamine (2.1 mL, 12 mmol) and 1-hydroxybenzotriazole (0.46 g, 3.04 mmol) in N,N-dimethylformamide (10 mL) at 0° C. was added O-benzotriazol-1-yl-N,N, N',N'-tetramethyluronium hexaflurorophosphate (1.15 g, 3.04 mmol). The reaction mixture was stirred at 0° C. for 2 hours. The reaction mixture was poured into ice water and extracted with ethyl acetate. The organic layer was separated, washed with water, brine, dried over sodium sulfate and concentrated. The residue was purified by chromatography over silica gel eluted with 2:1 ethyl acetate/hexanes to give 2-{(S)-2-[2-benzyloxycarbonylamino-2-(4-methoxy-3-methyl-phenyl)-acetylamino]-3-phenyl-propionylamino}-thiazole-4-carboxylic acid methyl ester as a white solid (1.3 g, 69%).

To a solution of 2-{(S)-2-[2-benzyloxycarbonylamino-2-(4-methoxy-3-methyl-phenyl)-acetylamino]-3-phenyl-propionylamino}-thiazole-4-carboxylic acid methyl ester (1.0 g, 1.62 mmol) in methanol (40 mL) was added formic acid (4 g, 87 mmol). The solution was then degassed with nitrogen for 10 minute, followed by the addition of palladium black (1 g, 9.4 mmol). The reaction mixture was stirred at room temperature under nitrogen for 0.5 hours. The reaction mixture was filtered through a short pad of celite and the filtrate was concentrated to dryness. The residue was neutralized with saturated aqueous sodium bicarbonate solution and extracted with ethyl acetate. The combined organic extracts were dried over sodium sulfate and concentrated to give crude 2-{(S)-2-[2-amino-2-(4-methoxy-3-methyl-phenyl)-acetylamino]-3-phenyl-propionylamino}-thiazole-4-carboxylic acid methyl ester as an off white foam (0.73 g, 93%).

A solution of 2-{(S)-2-[2-amino-2-(4-methoxy-3-methyl-phenyl)-acetylamino]-3-phenyl-propionylamino}-thiazole-4-carboxylic acid methyl ester (0.40 g , 0.83 mmol) and diisopropylethylamine (0.72 mL, 4.14 mmol) in dichloromethane (20 mL) was added to a solution of diphosgene (0.07 mL, 0.58 mmol) in dichloromethane (20 mL) at −10° C. The mixture was stirred at −10° C. for 0.5 hours. Water was added to quench the reaction, then the mixture was extracted with ethyl acetate. The organic layer was separated, washed with water, brine, dried over sodium sulfate and concentrated. The residue was purified by chromatography over silica gel eluted with ethyl acetate to give 2-{(S)-2-[4-(4-methoxy-3-methyl-phenyl)-2,5-dioxo-imidazolidin-1-yl]-3-phenyl-propionylamino}-thiazole-4-carboxylic acid methyl ester as an off white foam (0.29 g, 69%).

HRMS: Obs. Mass, 509.1486. Calcd. Mass, 509.1490 (M+H).

EXAMPLE 14

In a Manner Similar as that Described in Example 13, the Following Compounds were Prepared 2-{(S)-2-[4-(3-Isopropyl-4-methoxy-phenyl)-2,5-dioxo-imidazolidin-1-yl]-3-phenyl-propionylamino}-thiazole-4-carboxylic acid methyl ester

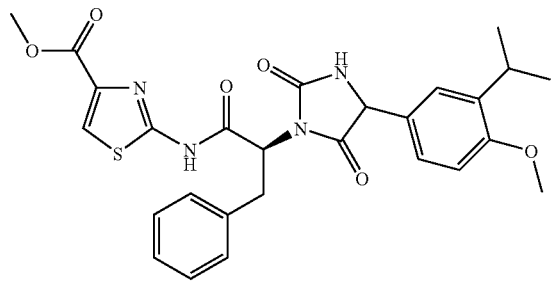

Prepared as described in example 13 except that 2-isopropylanisole was used in place of 2-methylanisole in step 1.

HRMS: Obs. Mass, 537.1802. Calcd. Mass, 537.1803 (M+H).

2-{(S)-2-[4-(3-Ethyl4-methoxy-phenyl)-2,5-dioxo-imidazolidin-1-yl]-3-phenyl-propionylamino}-thiazole-4-carboxylic acid methyl ester

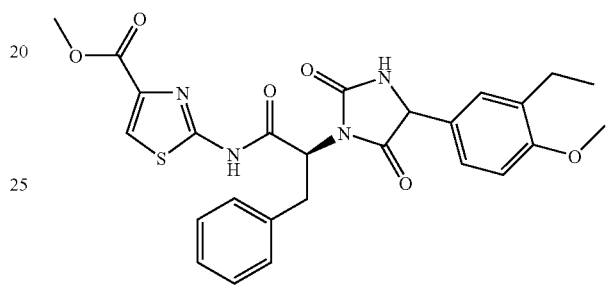

Prepared as described in example 13 except that 2-ethylanisole was used in place of 2-methylanisole in step 1.

HRMS: Obs. Mass, 523.11645. Calcd. Mass, 523.1646 (M+H).

EXAMPLE 15

2-{(S)-2-[(R)-4-(4-Methoxy-phenyl)-2,5-dioxo-imidazolidin-1-yl]-3-phenyl-propionylamino}-thiazole-4-carboxylic acid methoxy-methyl-amide

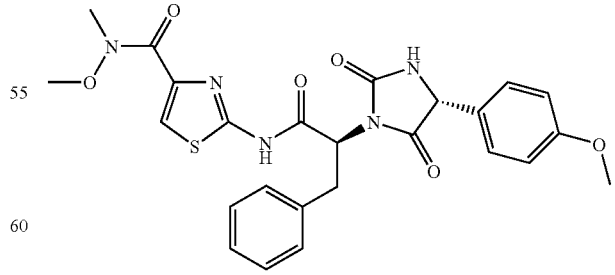

Prepared as described in example 10 except that 2-((S)-2-amino-3-phenyl-propionylamino)-thiazole-4-carboxylic acid methoxy-methyl-amide was used in place of 2-((S)-2-amino-3-phenyl-propionylamino)-thiazole-4-carboxylic acid methyl ester) and (R)—N-(tert-butyloxycarbonyl)-4-methyoxyphenylglycine was used in place of (R)-tert-butoxycarbonylamino-phenylacetic acid in step 1. 2-((S)-2-Amino-3-phenyl-propionylamino)-thiazole-4-carboxylic acid methoxy-methyl-amide was prepared as described in example 3, step 3, except that 2-amino-thiazole-4-carboxylic acid methoxy-methyl-amide was used in place of 2-amino-thiazole-4-carboxylic acid methyl ester. 2-Amino-thiazole-4-carboxylic acid methoxy-methyl-amide was prepared as follows.

To a solution of 2-amino-thiazole-4-carboxylic acid methyl ester (prepared as described in example 3, step 2) (10.0 g, 63.22 mmol) in 1:1 dichloromethane/tetrahydrofuran (200 mL) was added di-tert-butyl dicarbonate (15.2 g, 69.64 mmol) followed by 4-(dimethylamino)-pyridine (1.5 g, 12.30 mmol). The solution was stirred overnight at room temperature. The reaction was partitioned between ethyl acetate and 10% w/v aqueous citric acid. The organic layer was washed with water, brine and dried over sodium sulfate. Solvents were removed and the crude was passed through a plug of silica gel eluted with 2:3 ethyl acetate/hexanes to give 2-tert-butoxycarbonylamino-thiazole-4-carboxylic acid methyl ester as an oil (15.5 g, 95%).

2-tert-Butoxycarbonylamino-thiazole-4-carboxylic acid methyl ester (15.5 g, 60.01 mmol) was dissolved in 4:1 tetrahydrofuran:water (300 mL) followed by the addition of lithium hydroxide monohydrate (5.29 g, 126.07 mmol). The solution was stirred overnight at room temperature. Tetrahydrofuran was removed under vacuum and the salt was neutralized with 2.0 N aqueous hydrochloric acid. The resulting precipitate was filtered and dried to give 2-tert-butoxycarbonylamino-thiazole-4-carboxylic acid (10.4 g, 71%).

2-tert-Butoxycarbonylamino-thiazole-4-carboxylic acid (10.44 g, 42.74 mmol), N,O-dimethylhydroxylamine hydrochloride (5.0 g, 51.26 mmol), 1-[3-(dimethylamino)propyl]-3-ethylcarbodiimide hydrochloride (9.83 g, 51.28 mmol), 1-hydroxybenzotriazole hydrate (6.93 g, 51.28 mmol), triethylamine (7.15 ml, 51.28 mmol) and 4-(dimethylamino) pyridine (1.04 g, 8.52 mmol) were combined in dichloromethane (200 mL) and stirred overnight at room temperature. The resulting solution was poured into ethyl acetate and washed with 0.2 M aqueous hydrochloric acid, water, brine and dried over magnesium sulfate. Solvent was removed and the crude was by purified over silica gel eluted with 80% v/v ethyl acetate in hexane to give [4-(methoxy-methyl-carbamoyl)-thiazol-2-yl]-carbamic acid tert-butyl ester as a foam (17.0 g, 95%).

To a solution of [4-(methoxy-methyl-carbamoyl)-thiazol-2-yl]-carbamic acid tert-butyl ester (1.0 g, 3.48 mmol) in dichloromethane (20 mL) was added trifluoroacetic acid (5.0 mL, 64.9 mmol) at 0° C. The reaction was warmed to ambient temperature and stirred for 4 hours. The solvent was removed under vacuum and the residue was partitioned between ethyl acetate and saturated aqueous sodium bicarbonate. The aqueous layer was extracted with ethyl acetate and the organic extracts were combined, washed with brine and dried over sodium sulfate. The solvent was removed to give 2-amino-thiazole-4-carboxylic acid methoxy-methyl-amide as a foam (585 mg, 90%).

HRMS: Obs. Mass, 524.1599. Calcd. Mass, 524.1599 (M+H).

EXAMPLE 16

(S)—N-(4-Acetyl-thiazol-2-yl)-2-(2,5-dioxo-4-phenyl-imidazolidin-1-yl)-3-phenyl-propionamide

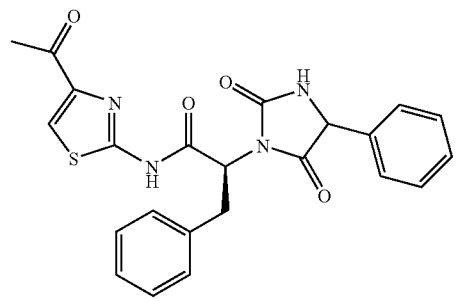

Prepared as described in example 3 except that 1-(2-amino-thiazol-4-yl)-ethanone was used in place of 2-amino-thiazole-4-carboxylic acid methyl ester used in step 3 and tert-butoxycarbonylamino-phenylacetic acid was used in place of tert-butoxycarbonylamino-(3-fluoro-4-methoxy-phenyl)-acetic acid used in step 7 of the synthesis. 1-(2-Amino-thiazol-4-yl)-ethanone was prepared as follows.

To a solution of thiourea (6.79 g, 89.2 mmol) in absolute ethanol (100 mL) was added 1-chloro-butane-2,3-dione (prepared as described by Bonnema, J. et al., *Rec. Trav. Chim. Pays-Bas* 1960, 79, 1137) (10.75 g, 89.2 mmol) and the mixture stirred at room temperature for 72 hours. The dark brown suspension was concentrated in vacuo, the residue taken up in water (350 mL), acidified with 1M aqueous hydrochloric acid (20 mL) and extracted with ethyl acetate (2×100 mL). The aqueous layer was then neutralized with solid sodium bicarbonate to form a light brown solid which was isolated by filtration. The precipitate was washed with 1:1 hexanes/ether (100 mL), 1:1 hexanes/ethyl acetae (100 mL) and then dried in vacuo over potassium hydroxide to give 1-(2-amino-thiazol-4-yl)-ethanone as a light brown solid (9.91 g, 78%).

HRMS: Obs. Mass, 449.1283. Calcd. Mass, 449.1278.

EXAMPLE 17

2-[(S)-2-(2,5-Dioxo-4-phenyl-imidazolidin-1-yl)-3-phenyl-propionylamino]-thiazole-4-carboxylic acid amide

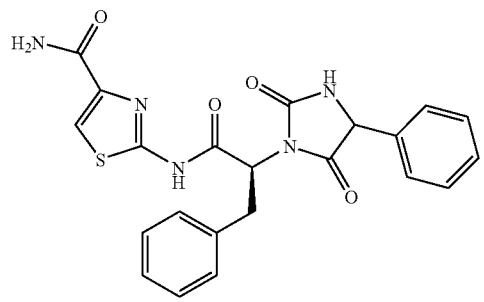

A solution of 2-amino-thiazole-4-carboxylic acid ethyl ester (258 mg, 1.5 mmol) (prepared as described in example 3, step 1) in concentrated aqueous ammonium hydroxide was heated to reflux for 8 hours. The reaction mixture was concentrated to dryness and residual water removed by azeotropic distillation with toluene. The residue was purified by chromatography over silica gel eluted with 2% v/v methanol in ethyl acetate to give 2-amino-thiazole-4-carboxylic acid amide as a colorless solid (149 mg, 69%).

LR-MS: Obs. Mass, 143.0. Calcd. Mass, 143.0153 ($M^+$).

To a solution of (S)-phenylalanine ethyl ester hydrochloride (5.09 g, 22.2 mmol) and tert-butyloxycarbonylphenylglycine (5.06 g, 20.1 mmol) in N,N-dimethylformamide (100 mL) was added diisopropylethylamine (4.2 mL, 24.1 mmol) and O-benzotriazol-1-yl-N,N,N',N'-tetramethyluronium hexafluorophosphate (9.16 g, 24.2 mmol) and the mixture stirred at ambient temperature overnight. The reaction mixture was poured into ethyl acetate (750 mL), washed with 1:1 1M aqueous hydrochloric acid/brine (2×75 mL), 1:1 saturated aqueous sodium bicarbonate solution/brine (2×75 mL), brine (200 mL), dried over sodium sulfate and concentrated in vacuo to give 2-(S)-(2-tert-butoxycarbonylamino-2-phenyl-acetylamino)-3-phenyl-propionic acid ethyl ester as a pale yellow solid which still contained some N,N-dimethylformamide.

LR-MS: Obs. Mass, 427.38. Calcd. Mass, 427.2233 (M+H).

(3) To a solution of 2-(S)-(2-tert-butoxycarbonylamino-2-phenyl-acetylamino)-3-phenyl-propionic acid ethyl ester (≈20 mmol) in 3:1 v/v tetrahydrofuran/water (80 mL total) was added lithium hydroxide monohydrate (1.06 g, 25.3 mmol) and the mixture was stirred at ambient temperature for 5 hours. The reaction mixture was poured into water (300 mL), diluted with brine (100 mL), acidified with 1M aqueous hydrochloric acid (30 mL, 30 mmol) and extracted with ethyl acetate (3×100 mL). the combined organic extracts were washed with brine (2×100 mL), dried with sodium sulfate and concentrated in vacuo to give 2-(S)-(2-tert-butoxycarbonylamino-2-phenyl-acetylamino)-3-phenyl-propionic acid as a colorless solid (8.16 g, 100%).

LR-MS: Obs. Mass, 399.16. Calcd. Mass, 399.1920 (M+H).

To a solution of 2-(S)-(2-tert-butoxycarbonylamino-2-phenyl-acetylamino)-3-phenyl-propionic acid (239 mg, 0.6 mmol) and 2-amino-thiazole-4-carboxylic acid amide (71.5 mg, 0.5 mmol) in N,N-dimethylformamide (5 mL) was added diisopropylethylamine (174 µL, 9.99 mmol) and O-benzotriazol-1-yl-N,N,N',N'-tetramethyluronium hexafluorophosphate (455 mg, 1.2 mmol) and the mixture stirred at ambient temperature overnight. The reaction was quenched with saturated aqueous ammonium chloride solution (10 mL), the mixture poured into water (50 mL) and extracted with ethyl acetate (3×20 mL). The combined organic extracts were washed with water (3×10 mL), brine (20 mL), dried over sodium sulfate and concentrated in vacuo. The residue was purified by chromatography over silica gel eluted with ethyl acetate to give {[1-((S)-4-carbamoyl-thiazol-2-ylcarbamoyl)-2-phenyl-ethylcarbamoyl]-phenyl-methyl}-carbamic acid tert-butyl ester as a glassy solid (31 mg, 12%).

LR-MS: Obs. Mass, 524.25. Calcd. Mass, 524.1967 (M+H).

{[1-((S)-4-Carbamoyl-thiazol-2-ylcarbamoyl)-2-phenyl-ethylcarbamoyl]-phenyl-methyl}-carbamic acid tert-butyl ester (31 mg, 0.059 mmol) was dissolved in dichloromethane (0.5 mL) at 0° C. and trifluoroacetic acid (0.5 mL, 6.5 mmol) added. After stirring at 0° C. for 7 hours the reaction mixture was concentrated in vacuo and the residue neutralized with saturated aqueous sodium bicarbonate (20 mL) and the aqueous mixture was extracted with ethyl acetate (3×10 mL). The combined organic extracts were washed with water (10 mL), brine (10 mL), dried over sodium sulfate and concentrated in vacuo to give 2-[2-(S)-(2-amino-2-phenyl-acetylamino)-3-phenyl-propionylamino]-thiazole-4-carboxylic acid amide as a pale yellow solid which was used without purification (21.5 mg, 86%).

LR-MS: Obs. Mass, 424.20. Calcd. Mass, 424.1443 (M+H).

To a solution of diphosgene (3.7 µL, 0.03 mmol) in a 1:1 v/v mixture of dichloromethane and toluene (0.5 mL total volume) was added dropwise with stirring a solution of 2-[2-(S)-(2-amino-2-phenyl-acetylamino)-3-phenyl-propionylamino]-thiazole-4-carboxylic acid amide (21.5 mg, 0.051 mmol) and diisopropylethylamine (24 µL, 0.14 mmol) in a 1:1 v/v mixture of dichloromethane and toluene (1 mL total volume). After stirring for 30 minutes, methanol (0.1 mL) was added and the reaction mixture concentrated in vacuo. The residue was purified by reverse phase high performance liquid chromatography using a C-18 stationary phase gradient eluted with a water/acetonitrile mixture containing 0.1% v/v trifluoroacetic acid in both components of the solvent system. After lyophilization 2-[(S)-2-(2,5-dioxo-4-phenyl-imidazolidin-1-yl)-3-phenyl-propionylamino]-thiazole-4-carboxylic acid amide was obtained as an amorphous colorless solid (4.0 mg, 18%).

HR-MS: Obs. Mass, 450.1234. Calcd. Mass, 450.1231 (M+H).

EXAMPLE 18

2-[(S)-2-(2,5-Dioxo-4-phenyl-imidazolidin-1-yl)-3-phenyl-propionylamino]-thiazole-4-carboxylic acid dimethylamide

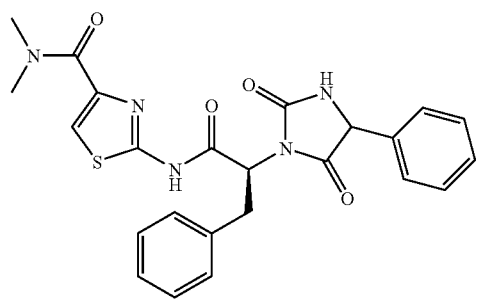

Prepared as described in example 17 except that 2-amino-thiazole-4-carboxylic acid dimethylamide was used in place of 2-amino-thiazole-4-carboxylic acid amide in step 4. 2-Amino-thiazole-4-carboxylic acid dimethylamide was prepared as follows:

To a suspension of 2-tert-butoxycarbonylamino-thiazole-4-carboxylic acid (prepared as described in example 15) (183 mg, 0.75 mmol) in toluene (7 mL) was added thionyl chloride (2.2 mL, 30 mmol) and the mixture heated to reflux under argon for 2.5 hours. The mixture was then concentrated in vacuo, the residue suspended in dichloromethane (7 mL), a 2 M solution of dimethylamine in tetrahydrofuran (0.5 mL, 1 mmol) added and the mixture stirred at ambient temperature under argon overnight. The reaction mixture was concentrated in vacuo, the residue suspended in ethyl acetate and the solid removed by filtration. The filtrate was concentrated in vacuo and the residue purified by chromatography over silica gel eluted with 1% v/v methanol in ethyl acetate to give (4-dimethylcarbamoyl-thiazol-2-yl)-carbamic acid tert-butyl ester as a colorless solid (152 mg, 75%).

To a stirred solution of (4-dimethylcarbamoyl-thiazol-2-yl)-carbamic acid tert-butyl ester (150 mg, 0.53 mmol) in dichloromethane (1 mL) at 0° C. was added trifluoroacetic acid (2.5 mL, 32 mmol) and the mixture stirred at 0° C. until all of the starting material had been consumed. The reaction mixture was concentrated in vacuo, the residue dissolved in ethyl acetate, washed with saturated aqueous sodium bicarbonate (2×), brine, dried over sodium sulfate and concentrated in vacuo to give crude 2-amino-thiazole-4-carboxylic acid dimethylamide as a viscous colorless oil which was used without further purification (85 mg, 90%).

HR-MS: Obs. Mass, 478.1548. Calcd. Mass, 478.1544 (M+H).

Compound $IC_{50}$ Determination in MEK Cascade Assay

The evaluation of the compounds as MEK inhibitor was performed in a bead-based FP assay termed IMAP assay with MEK cascade components. In brief, the assay was performed in a reaction solution containing 10 mM HEPES, pH 7.0, 10 mM $MgCl_2$, 50 mM NaCl, 0.1 mM $NaVO_4$, and 1 mM DTT in the presence of 50 μM ATP, 0.45 nM c-RAF, 11.25 nM MEK, 90.5 nM ERK, and 0.5 μM FITC-labeled ERK (FITC-Aca-Ala-Ala-Ala-Thr-Gly-Pro-Leu-Ser-Pro-Gly-Pro-Phe-Ala-NH2). C-RAF, MEK, ERK and the ERK peptide substrates were added sequentially into the reaction buffer. Activated c-Raf phosphorylates MEK, activated MEK phosphorylates ERK, and subsequently activated ERK phosphrylates its peptide substrate. The FITC-labeled peptide substrates, when phosphorylated by the kinase, bind to nanoparticles derivatized with trivalent metal cations through a metal-phospholigand interaction. The result of this bound fluoresceinated phosphorylated product is an increase in polarization signal caused by a decrease in the molecular mobility of the bound product. Ten-point serial dilutions of the compounds were added into the MEK cascade assays before mixing with ERK and ERK peptide substrates. The reaction was incubated at 37° C. for 20 minutes for MEK activation, 20 minutes for ERK activation, 30 minutes for ERK peptide substrate phosphorylation, then was incubated overnight at room temperature for binding of IMAP beads. The IMAP assay was performed in a 384-well plate format. The changes in fluorescence polarization were measured by LJL instrument at 485 nm for excitation and 530 nm for emission. Polarization value (MP) was calculated as the following:

$$(MP)=1000*(intensity_{vertical}-intensity_{horizontal})/(intensity_{vertical}+intensity_{horizontal}).$$

The $IC_{50}$ values were generated using Excel XLfit3 wizard. Percent activity and percent inhibition of reactions in the presence of a compound were calculated by comparing their MP values to those without a compound (as 100% activity).

The compounds of Examples 1-18 exhibited $IC_{50}$ values of less than 20 μM.

What is claimed is:
1. A compound of the formula

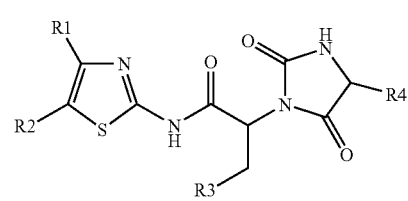

wherein
$R^1$ is $COR^5$;
$R^2$ is hydrogen;
$R^3$ is selected from the group consisting of substituted or unsubstituted alkyl, substituted or unsubstituted alkenyl, substituted or unsubstituted alkynyl, cycloalkyl, substituted or unsubstituted heterocycle, substituted or unsubstituted aryl and substituted or unsubstituted heteroaryl;
$R^4$ is selected from the group consisting of substituted or unsubstituted aryl and substituted or unsubstituted heteroaryl;
$R^5$ is selected the group consisting of lower alkyl, lower alkoxy and amine substituted by hydrogen, lower alkyl or lower alkoxy;
and the pharmaceutically acceptable salts, esters or prodrugs thereof.

2. The compound of claim 1 wherein
$R^1$ is $COR^5$ where $R^5$ is lower alkoxy;
$R^3$ is substituted aryl or substituted heteroaryl; and
$R^4$ is substituted aryl or substituted heteroaryl.

3. The compound of claim 2 wherein $R^5$ is methoxy.

4. A compound selected from the group consisting of
2-[(S)-2-((S)-2,5-dioxo-4-phenyl-imidazolidin-1-yl)-4-methyl-pentanoylamino]-thiazole-4-carboxylic acid methyl ester;
2-[(S)-3-cyclohexyl-2-((S)-2,5-dioxo-4-phenyl-imidazolidin-1-yl)-propionylamino]-thiazole-4-carboxylic acid methyl ester;
2-[(S)-2-((S)-2,5-dioxo-4-phenyl-imidazolidin-1-yl)-hexanoylamino]-thiazole-4-carboxylic acid methyl ester;
2-[(S)-2-((S)-2,5-dioxo-4-phenyl-imidazolidin-1-yl)-2-phenyl-acetylamino]-thiazole-4-carboxylic acid methyl ester;
2-[(R)-2-((S)-2,5-dioxo-4-phenyl-imidazolidin-1-yl)-3-(4-hydroxy-phenyl)-propionylamino]-thiazole-4-carboxylic acid methyl ester;
2-[(S)-2-((S)-2,5-dioxo-4-phenyl-imidazolidin-1-yl)-4-methylsulfanyl-butyrylamino]-thiazole-4-carboxylic acid methyl ester;
2-[(S)-2-((S)-2,5-dioxo-4-phenyl-imidazolidin-1-yl)-3-thiophen-2-yl-propionylamino]-thiazole-4-carboxylic acid methyl ester;
2-[(S)-2-((S)-2,5-dioxo-4-phenyl-imidazolidin-1-yl)-4-phenyl-butyrylamino]-thiazole-4-carboxylic acid methyl ester;
2-[(R)-2-((S)-2,5-dioxo-4-phenyl-imidazolidin-1-yl)-pentanoylamino]-thiazole-4-carboxylic acid methyl ester;
2-[(R)-2-((S)-2,5-dioxo-4-phenyl-imidazolidin-1-yl)-4-methyl-pentanoylamino]-thiazole-4-carboxylic acid methyl ester;

2-[(S)-2-((S)-2,5-dioxo-4-phenyl-imidazolidin-1-yl)-3-phenyl-propionylamino]-thiazole-4-carboxylic acid methyl ester;

2-[(S)-2-((R)-2,5-dioxo-4-phenyl-imidazolidin-1-yl)-4-methyl-pentanoylamino]-thiazole-4-carboxylic acid methyl ester;

2-[(S)-2-((S)-2,5-dioxo-4-phenyl-imidazolidin-1-yl)-3-naphthalen-2-yl-propionylamino]-thiazole-4-carboxylic acid methyl ester;

2-[(S)-3-biphenyl-4-yl-2-((S)-2,5-dioxo-4-phenyl-imidazolidin-1-yl)-propionylamino]-thiazole-4-carboxylic acid methyl ester;

2-[(S)-2-(2,5-dioxo-4-(2-methyl-phenyl)-imidazolidin-1-yl)-4-methyl-pentanoylamino]-thiazole-4-carboxylic acid methyl ester;

2-[(S)-2-(4-furan-2-yl-2,5-dioxo-imidazolidin-1-yl)-3-phenyl-propionylamino]-thiazole-4-carboxylic acid methyl ester;

2-[(S)-2-(4-naphthalen-2-yl-2,5-dioxo-imidazolidin-1-yl)-3-phenyl-propionylamino]-thiazole-4-carboxylic acid methyl ester;

2-{(S)-2-[4-(4-hydroxy-phenyl)-2,5-dioxo-imidazolidin-1-yl]-3-phenyl-propionylamino}-thiazole-4-carboxylic acid methyl ester;

2-{(S)-2-[4-(3-hydroxy-phenyl)-2,5-dioxo-imidazolidin-1-yl]-3-phenyl-propionylamino}-thiazole-4-carboxylic acid methyl ester;

2-{(S)-2-[2,5-dioxo-4-(4-trifluoromethyl-phenyl)-imidazolidin-1-yl]-3-phenyl-propionylamino}-thiazole-4-carboxylic acid methyl ester;

2-{(S)-2-[4-(2-chloro-phenyl)-2,5-dioxo-imidazolidin-1-yl]-3-phenyl-propionylamino}-thiazole-4-carboxylic acid methyl ester;

2-{(S)-2-[4-(3-methoxy-phenyl)-2,5-dioxo-imidazolidin-1-yl]-3-phenyl-propionylamino}-thiazole-4-carboxylic acid methyl ester;

2-[(S)-2-(2,5-dioxo-4-(3-methyl-phenyl)-imidazolidin-1-yl)-3-phenyl-propionylamino]-thiazole-4-carboxylic acid methyl ester;

2-[(S)-2-(2,5-dioxo-4-(4-methyl-phenyl)-imidazolidin-1-yl)-4-methyl-pentanoylamino]-thiazole-4-carboxylic acid methyl ester;

2-{(S)-2-[4-(4-isopropyl-phenyl)-2,5-dioxo-imidazolidin-1-yl]-4-methyl-pentanoylamino}-thiazole-4-carboxylic acid methyl ester;

2-{(S)-2-[4-(4-chloro-phenyl)-2,5-dioxo-imidazolidin-1-yl]-4-methyl-pentanoylamino}-thiazole-4-carboxylic acid methyl ester;

2-{(S)-2-[4-(4-methoxy-phenyl)-2,5-dioxo-imidazolidin-1-yl]-4-methyl-pentanoylamino}-thiazole-4-carboxylic acid methyl ester;

2-[(S)-2-(4-furan-2-yl-2,5-dioxo-imidazolidin-1-yl)-4-methyl-pentanoylamino]-thiazole-4-carboxylic acid methyl ester;

2-[(S)-4-methyl-2-(4-naphthalen-2-yl-2,5-dioxo-imadazolidin-1-yl)-pentanoylamino]-thiazole-4-carboxylic acid methyl ester;

2-[(S)-2-(2,5-dioxo-4-thiophen-3-yl-imidazolidin-1-yl)-4-methyl-pentanoylamino]-thiazole-4-carboxylic acid methyl ester;

2-{(S)-2-[4-(4-fluoro-phenyl)-2,5-dioxo-imidazolidin-1-yl]-4-methyl-pentanoylamino}-thiazole-4-carboxylic acid methyl ester;

2-[(S)-2-(4-benzo[1,3]dioxol-5-yl-2,5-dioxo-imidazolidin-1-yl)-4-methyl-pentanoylamino]-thiazole-4-carboxylic acid methyl ester;

2-{(S)-2-[4-(3-iodo-phenyl)-2,5-dioxo-imidazolidin-1-yl]-4-methyl-pentanoylamino}-thiazole-4-carboxylic acid methyl ester;

2-{(S)-2-[4-(4-hydroxy-phenyl)-2,5-dioxo-imidazolidin-1-yl]-4-methyl-pentanoylamino}-thiazole-4-carboxylic acid methyl ester;

2-{(S)-2-[4-(3-hydroxy-phenyl)-2,5-dioxo-imidazolidin-1-yl]-4-methyl-pentanoylamino}-thiazole-4-carboxylic acid methyl ester;

2-{(S)-2-[2,5-dioxo-4-(3-trifluoromethyl-phenyl)-imidazolidin-1-yl]-4-methyl-pentanoylamino}-thiazole-4-carboxylic acid methyl ester;

2-{(S)-2-[4-(2-methoxy-phenyl)-2,5-dioxo-imidazolidin-1-yl]-4-methyl-pentanoylamino}-thiazole-4-carboxylic acid methyl ester;

2-{(S)-2-[4-(2-chloro-phenyl)-2,5-dioxo-imidazolidin-1-yl]-4-methyl-pentanoylamino}-thiazole-4-carboxylic acid methyl ester;

2-{(S)-2-[4-(2-fluoro-phenyl)-2,5-dioxo-imidazolidin-1-yl]-4-methyl-pentanoylamino}-thiazole-4-carboxylic acid methyl ester;

2-{(S)-2-[4-(3-fluoro-phenyl)-2,5-dioxo-imidazolidin-1-yl]-4-methyl-pentanoylamino}-thiazole-4-carboxylic acid methyl ester;

2-{(S)-2-[4-(3-methoxy-phenyl)-2,5-dioxo-imidazolidin-1-yl]-4-methyl-pentanoylamino}-thiazole-4-carboxylic acid methyl ester;

2-[(S)-2-(2,5-dioxo-4-(3-methyl-phenyl)-imidazolidin-1-yl)-4-methyl-pentanoylamino]-thiazole-4-carboxylic acid methyl ester;

2-[(S)-2-(2,5-dioxo-4-(4-methyl-phenyl)-imidazolidin-1-yl)-3-phenyl-propionylamino]-thiazole-4-carboxylic acid methyl ester;

2-[2-(2,5-dioxo-4-thiophen-3-yl-imidazolidin-1-yl)-3-phenyl-propionylamino]-thiazole-4-carboxylic acid methyl ester;

2-{(S)-2-[4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[4-(2,3-dihydro-benzo[1,4]dioxin-6-yl)-2,5-dioxo-imidazolidin-1-yl]-3-phenyl propionylamino}-thiazole-4-carboxylic acid methyl ester;

2-{(S)-2-[4-(2,3-dihydro-benzo[1,4]dioxin-5-yl)-2,5-dioxo-imidazolidin-1-yl]-3-phenyl-propionylamino}-thiazole-4-carboxylic acid methyl ester;

2-{(S)-2-[4-(2,3-dihydro-benzofuran-5-yl)-2,5-dioxo-imidazolidin-1-yl]-3-phenyl-propionylamino}-thiazole-4-carboxylic acid methyl ester;

2-{(S)-2-[4-(3,4-dimethoxy-phenyl)-2,5-dioxo-imidazolidin-1-yl]-3-phenyl-propionylamino}-thiazole-4-carboxylic acid methyl ester;

2-{(S)-2-[4-(2,3-diflouro-phenyl)-2,5-dioxo-imidazolidin-1-yl]-3-phenyl-propionylamino}-thiazole-4-carboxylic acid methyl ester;

2-{(S)-2-[4-(2,4-difluoro-phenyl)-2,5-dioxo-imidazolidin-1-yl]-3-phenyl-propionylamino}-thiazole-4-carboxylic acid methyl ester;

2-{(S)-2-[4-(3-chloro-4-methoxy-phenyl)-2,5-dioxo-imidazolidin-1-yl]-3-phenyl-propionylamino}-thiazole-4-carboxylic acid methyl ester;

2-{(S)-2-[4-(3,5-difluoro-phenyl)-2,5-dioxo-imidazolidin-1-yl]-3-phenyl-propionylamino}-thiazole-4-carboxylic acid methyl ester;

2-{(S)-2-[4-(2,6-difluoro-phenyl)-2,5-dioxo-imidazolidin-1-yl]-3-phenyl-propionylamino}-thiazole-4-carboxylic acid methyl ester;

2-{(S)-2-[4-(5-fluoro-2-methoxy-phenyl)-2,5-dioxo-imidazolidin-1-yl]-3-phenyl-propionylamino}-thiazole-4-carboxylic acid methyl ester;
2-{(S)-2-[4-(2-fluoro-4-methoxy-phenyl)-2,5-dioxo-imidazolidin-1-yl]-3-phenyl-propionylamino}-thiazole-4-carboxylic acid methyl ester;
2-{(S)-2-[4-(4-dimethylamino-phenyl)-2,5-dioxo-imidazolidin-1-yl]-3-phenyl-propionylamino}-thiazole-4-carboxylic acid methyl ester;
2-[2-(4-benzo[1,3]dioxol-5-yl-2,5-dioxo-imidazolidin-1-yl)-3-(4-cyano-phenyl)-propionylamino]-thiazole-4-carboxylic acid methyl ester;
2-[(S)-2-(4-benzo[1,3]dioxol-5-yl-2,5-dioxo-imidazolidin-1-yl)-3-(4-carbamoyl-phenyl)-propionylamino]-thiazole-4-carboxylic acid methyl ester;
2-((S)-2-{2,5-dioxo-4-[4-(2-pyrrolidin-1-yl-ethoxy)-phenyl]-imidazolidin-1-yl}-3-phenyl-propionylamino)-thiazole-4-carboxylic acid methyl ester;
2-((S)-2-{(R)-4-[4-(3-methoxy-propoxy)-phenyl]-2,5-dioxo-imidazolidin-1-yl}-3-phenyl-propionylamino)-thiazole-4-carboxylic acid methyl ester;
2-{(S)-2-[4-(1-methyl-1H-benzoimidazol-5-yl)-2,5-dioxo-imidazolidin-1-yl]-3-phenyl-propionylamino}-thiazole-4-carboxylic acid methyl ester;
2-[(S)-2-(4-benzo[1,3]dioxol-5-yl-2,5-dioxo-imidazolidin-1-yl)-3-(2-trifluoromethyl-phenyl)-propionylamino]-thiazole-4-carboxylic acid methyl ester;
2-[(S)-2-[4-(4-methylsulfanyl-phenyl)-2,5-dioxo-imidazolidin-1-yl]-3-(2-trifluoromethyl-phenyl)-propionylamino]-thiazole-4-carboxylic acid methyl ester;
2-[(S)-2-[4-(4-methanesulfinyl-phenyl)-2,5-dioxo-imidazolidin-1-yl]-3-(2-trifluoromethyl-phenyl)-propionylamino]-thiazole-4-carboxylic acid methyl ester;
2-[(S)-2-(2,5-dioxo-4-thiophen-2-yl-imidazolidin-1-yl)-3-phenyl-propionylamino]-thiazole-4-carboxylic acid methyl ester;
2-[(S)-2-[4-(2,3-dihydro-benzo[1,4]dioxin-6-yl)-2,5-dioxo-imidazolidin-1-yl]-3-(1H-indol-3-yl)-propionylamino]-thiazole-4-carboxylic acid methyl ester;
2-{(S)-2-[4-(2,2-difluoro-benzo[1,3]dioxol-5-yl)-2,5-dioxo-imidazolidin-1-yl]-3-phenyl-propionylamino}-thiazole-4-carboxylic acid methyl ester;
2-{(S)-2-[4-(3,5-dimethoxy-phenyl)-2,5-dioxo-imidazolidin-1-yl]-3-phenyl-propionylamino}-thiazole-4-carboxylic acid methyl ester;
2-[(S)-2-(4-benzo[1,3]dioxol-5-yl-2,5-dioxo-imidazolidin-1-yl)-3-pyridin-3-yl-propionylamino]-thiazole-4-carboxylic acid methyl ester;
2-[2-(4-benzo[1,3]dioxol-5-yl-2,5-dioxo-imidazolidin-1-yl)-3-(tetrahydro-pyran-4-yl)-propionylamino]-thiazole-4-carboxylic acid methyl ester;
2-[(S)-2-(4-benzo[1,3]dioxol-5-yl-2,5-dioxo-imidazolidin-1-yl)-3-(1-methyl-1H-imidazol-4-yl)-propionylamino]-thiazole-4-carboxylic acid methyl ester;
2-[(S)-2-[4-(2,3-dihydro-benzo[1,4]dioxin-6-yl)-2,5-dioxo-imidazolidin-1-yl]-3-(4-methanesulfonylamino-phenyl)-propionylamino]-thiazole-4-carboxylic acid methyl ester;
2-[(S)-2-(4-benzo[1,3]dioxol-5-yl-2,5-dioxo-imidazolidin-1-yl)-3-phenyl-propionylamino]-thiazole-4-carboxylic acid methyl ester;
2-{(S)-2-[4-(2-fluoro-4-methoxy-phenyl)-2,5-dioxo-imidazolidin-1-yl]-4-methyl-pentanoylamino}-thiazole-4-carboxylic acid methyl ester;
2-{(S)-2-[4-(2,3-difluoro-phenyl)-2,5-dioxo-imidazolidin-1-yl]-4-methyl-pentanoylamino}-thiazole-4-carboxylic acid methyl ester;
2-{(S)-2-[4-(2-fluoro-4-methoxy-phenyl)-2,5-dioxo-imidazolidin-1-yl]-4-methyl-pentanoylamino}-thiazole-4-carboxylic acid methyl ester;
2-{3-cyclopentyl-(S)-2-[4-(3-fluoro-4-methoxy-phenyl)-2,5-dioxo-imidazolidin-1-yl]propionylamino}-thiazole-4-carboxylic acid methyl ester;
(S)-2-[2-(4-benzo[1,3]dioxol-5-yl-2,5-dioxo-imidazolidin-1-yl)-3-cyclopentyl-propionylamino]-thiazole-4-carboxylic acid methyl ester;
(S)-2-[2-(4-benzo[1,3]dioxol-5-yl-2,5-dioxo-imidazolidin-1-yl)-3-cyclopropyl-propionylamino]-thiazole-4-carboxylic acid methyl ester;
(S)-2-[2-(4-benzo[1,3]dioxol-5-yl-2,5-dioxo-imidazolidin-1-yl)-4-methanesulfonyl-butyrylamino]-thiazole-4-carboxylic acid methyl ester;
2-[(S)-2-(4-benzo[1,3]dioxol-5-yl-2,5-dioxo-imidazolidin-1-yl)-3-(3-chloro-phenyl)-propionylamino]-thiazole-4-carboxylic acid methyl ester;
2-[(S)-2-(4-benzol[1,3]dioxol-5-yl-2,5-dioxo-imidazolidin-1-yl)-3-(2-chloro-phenyl)-propionylamino]-thiazole-4-carboxylic acid methyl ester;
2-[(S)-2-[4-(2,3-dihydro-benzo[1,4]dioxin-6-yl)-2,5-dioxo-imidazolidin-1-yl]-3-(2-methoxy-phenyl)-propionylamino]-thiazole-4-carboxylic acid methyl ester;
2-[(S)-2-(4-benzo[1,3]dioxol-5-yl-2,5-dioxo-imidazolidin-1-yl)-3-(3-methoxy-phenyl)propionylamino]-thiazole-4-carboxylic acid methyl ester;
2-[(S)-2-[4-(3-fluoro-4-methoxy-phenyl)-2,5-dioxo-imidazolidin-1-yl]-3-(2-methoxy-phenyl)-propionylamino]-thiazole-4-carboxylic acid methyl ester;
2-[(S)-2-(4-benzo[1,3]dioxol-5-yl-2,5-dioxo-imidazolidin-1-yl)-3-(4-methoxy-phenyl)propionylamino]-thiazole-4-carboxyl ic acid methyl ester;
2-[(S)-2-(4-benzo[1,3]dioxol-5-yl-2,5-dioxo-imidazolidin-1-yl)-3-o-tolyl-propionylamino]-thiazole-4-carboxylic acid methyl ester;
2-{2-[4-(2,3-dihydro-benzo[1,4]dioxin-6-yl)-2,5-dioxo-imidazolidin-1-yl]-3-indan-1-yl-propionylamino}-thiazole-4-carboxylic acid methyl ester;
2-[(S)-2-[4-(2,3-dihydro-benzo[1,4]dioxin-6-yl)-2,5-dioxo-imidazolidin-1-yl]-3-(2-fluoro-phenyl)-propionylamino]-thiazole-4-carboxylic acid methyl ester;
2-[(S)-2-[4-(2,3-dihydro-benzo[1,4]dioxin-6-yl)-2,5-dioxo-imidazolidin-1-yl]-3-(3,4-dimethoxy-phenyl)-propionylamino]-thiazole-4-carboxylic acid methyl ester;
2-[(2-[4-(2,3-dihydro-benzo[1,4]dioxin-6-yl)-2,5-dioxo-imidazolidin-1-yl]-3-(3-methoxycarbonylmethoxy-phenyl)-propionylamino]-thiazole-4-carboxylic acid methyl ester;
2-{(S)-3-benzooxazol-5-yl-2-[4-(2,3-dihydro-benzo[1,4]dioxin-6-yl)-2,5-dioxo-imidazolidin-1-yl]-propionylamino}-thiazole-4-carboxylic acid methyl ester, isomer 1;
2-{(S)-3-benzooxazol-5-yl-2-[4-(2,3-dihydro-benzo[1,4]dioxin-6-yl)-2,5-dioxo-imidazolidin-1-yl]-propionylamino}-thiazole-4-carboxylic acid methyl ester, isomer 2;
2-[(S)-2-[4-(2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester, isomer 1;
2-[(S)-2-[4-2,3-dihydro-benzo[1,4]dioxin-6-yl)-2,5-dioxo-imidazolidin-1-yl]-3-(4-dimethylamino-phenyl)-propionylamino]-thiazole-4-carboxylic acid methyl ester, isomer 2;

2-{(S)-2-[4-(3-fluoro-4-methoxy-phenyl)-2,5-dioxo-imidazolidin-1-yl]-3-thiazol-4-ylpropionylamino}-thiazole-4-carboxylic acid methyl ester;

2-[(S)-2-(4-benzo[1,3]dioxol-5-yl-2,5-dioxo-imidazolidin-1-yl)-3-thiazol-4-yl-propionylamino]-thiazole-4-carboxylic acid methyl ester;

2-{(S)-2-[4-(2,3-dihydro-benzo[1,4]dioxin-6-yl)-2,5-dioxo-imidazolidin-1-yl]-3-thiazol-4-yl-propionylamino}-thiazole-4-carboxylic acid methyl ester;

2-{(S)-2-[4-(3-fluoro-4-methoxy-phenyl)-2,5-dioxo-imidazolidin-1-yl]-3-furan-2-yl-propionylamino}-thiazole-4-carboxylic acid methyl ester;

2-[(S)-2-(4-benzo[1,3]dioxol-5-yl-2,5-dioxo-imidazolidin-1-yl)-3-(3-methyl-3H-imidazol-4-yl)-propionylamino]-thiazole-4-carboxylic acid methyl ester;

2-{(S)-2-[4-(2,3-dihydro-benzo[1,4]dioxin-6-yl)-2,5-dioxo-imidazolidin-1-yl]-3-pyridin-3-yl-propionylamino}-thiazole-4-carboxylic acid methyl ester;

2-{(S)-2-[(R)-4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[(S)-4-(3-fluoro-4-methoxy-phenyl)-2,5-dioxo-imidazolidin-1-yl]-3-phenyl-propionylamino}-thiazole-4-carboxylic acid methyl ester;

2-{(S)-2-[(R)-4-(3-chloro-4-methoxy-phenyl)-2,5-dioxo-imidazolidin-1-yl]-3-phenyl-propionylamino}-thiazole-4-carboxylic acid methyl ester;

2-{(S)-2-[(R)-4-benzo[1,3]dioxol-5-yl-2,5-dioxo-imidazolidin-1-yl]-3-phenyl-propionylamino}-thiazole-4-carboxylic acid methyl ester;

2-{(S)-2-[(R)-4-(3,5-difluoro-phenyl)-2,5-dioxo-imidazolidin-1-yl]-3-phenyl-propionylamino}-thiazole-4-carboxylic acid methyl ester;

2-{(S)-2-[(R)-4-(3-fluoro-4-methoxy-phenyl)-2,5-dioxo-imidazolidin-1-yl]-3-(2-methoxy-phenyl)-propionylamino}-thiazole-4-carboxylic acid methyl ester;

2-[(S)-2-((R)-4-benzo[1,3]dioxol-5-yl-2,5-dioxo-imidazolidin-1-yl)-3-cyclopropyl-propionylamino]-thiazole-4-carboxylic acid methyl ester;

2-[(S)-2-((R)-4-benzo[1,3]dioxol-5-yl-2,5-dioxo-imidazolidin-1-yl)-3-cyclopentyl-propionylamino]-thiazole-4-carboxylic acid methyl ester;

2-{3-cyclopentyl-(S)-2-[(R)-4-(3-fluoro-4-methoxy-phenyl)-2,5-dioxo-imidazolidin-1-yl]-propionylamino}-thiazole-4-carboxylic acid methyl ester;

2-[(S)-2-((S)-2,5-dioxo-4-thiophen-3-yl-imidazolidin-1-yl)-3-phenyl-propionylamino]-thiazole-4-carboxylic acid methyl ester;

2-{(S)-2-[(R)-4-(4-methoxy-phenyl)-2,5-dioxo-imidazolidin-1-yl]-3-thiazol-2-yl-propionylamino}-thiazole-4-carboxylic acid methyl ester;

2-{(S)-2-[(R)-4-(2-fluoro-4-methoxy-phenyl)-2,5-dioxo-imidazolidin-1-yl]-3-phenyl-propionylamino}-thiazole-4-carboxylic acid methyl ester;

2-[(S)-2-(2,5-dioxo-(R)-4-phenyl-imidazolidin-1-yl)-3-phenyl-propionylamino]-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-phenyl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-(4-fluoro-phenyl)-propionylamino}-thiazole-4-carboxylic acid methyl ester;

2-{3-(3,5-difluoro-phenyl)-(S)-2-[(R)-4-(2,3-dihydro-benzo[1,4]dioxin-6-yl)-2,5-dioxo-imidazolidin-1-yl]-propionylamino}-thiazole-4-carboxylic acid methyl ester;

2-[(S)-2-[(R)-4-(2,3-dihydro-benzo[1,4]dioxin-6-yl)-2,5-dioxo-imidazolidin-1-yl]-3-(2-fluoro-phenyl)-propionylamino]-thiazole-4-carboxylic acid methyl ester;

2-{(S)-2-[(R)-4-(4-methoxy-phenyl)-2,5-dioxo-imidazolidin-1-yl]-3-phenyl-propionylamino}-thiazole-4-carboxylic acid methyl ester;

2-{3-(2-methoxy-phenyl)-(S)-2-[(R)-4-(4-methoxy-phenyl)-2,5-dioxo-imidazolidin-1-yl]-propionylamino}-thiazole-4-carboxylic acid methyl ester;

2-[(S)-2-[(R)-4-(2,3-dihydro-benzo[1,4]dioxin-6-yl)-2,5-dioxo-imidazolidin-1-yl]-3-(3-fluoro-phenyl)-propionylamino]-thiazole-4-carboxylic acid methyl ester;

2-{3-(3,4-difluoro-phenyl)-(S)-2-[(R)-4-(2,3-dihydro-benzo[1,4]dioxin-6-yl)-2,5-dioxo-imidazolidin-1-yl]-propionylamino}-thiazole-4-carboxylic acid methyl ester;

2-((S)-2-{(R)-4-[4-(2-hydroxy-ethoxy)-phenyl]-2,5-dioxo-imidazolidin-1-yl}-3-phenyl-propionylamino)-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiophen-2-yl-propionylamino}-thiazole-4-carboxylic acid methyl ester;

2-{(S)-2-[(R)-4-(4-methoxy-phenyl)-2,5-dioxo-imidazolidin-1-yl]-3-thiazol-4-yl-propionylamino}-thiazole-4-carboxylic acid methyl ester;

2-{(S)-2-[(R)-4-(4-methoxy-phenyl)-2,5-dioxo-imidazolidin-1-yl]-3-thiazol-2-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiazol-4-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-thiophen-3-yl-propionylamino}-thiazole-4-carboxylic acid methyl ester;

2-{(S)-2-[(R)-4-(2,3-dihydro-benzo[1,4]dioxin-6-yl)-2,5-dioxo-imidazolidin-1-yl]-3-pyrazol-1-yl-propionylamino}-thiazole-4-carboxylic acid methyl ester;

2-{(R)-2-[(R)-4-(4-methoxy-phenyl)-2,5-dioxo-imidazolidin-1-yl]-3-phenyl-propionylamino}-thiazole-4-carboxylic acid methyl ester;

2-{(S)-2-[(S)-4-(4-methoxy-phenyl)-2,5-dioxo-imidazolidin-1-yl]-3-phenyl-propionylamino}-thiazole-4-carboxylic acid methyl ester;

2-((S)-2-{(R)-4-[4-(2-methoxy-ethoxy)-phenyl]-2,5-dioxo-imidazolidin-1-yl}-3-phenyl-propionylamino)-thiazole-4-carboxylic acid methyl ester;

2-[2-[(R)-4-(4-methoxy-phenyl)-2,5-dioxo-imidazolidin-1-yl]-3-(3-nitro-phenyl)-propionylamino]-thiazole-4-carboxylic acid methyl ester;

2-[(S)-2-[(R)-4-(4-methoxy-phenyl)-2,5-dioxo-imidazolidin-1-yl]-3-(4-nitro-phenyl)-propionylamino]-thiazole-4-carboxylic acid methyl ester;

2-{(S)-3-(4-amino-phenyl)-2-[(R)-4-(4-methoxy-phenyl)-2,5-dioxo-imidazolidin-1-yl]-propionylamino}-thiazole-4-carboxylic acid methyl ester;

2-{(S)-3-(4-dimethylamino-phenyl)-2-[(R)-4-(4-methoxy-phenyl)-2,5-dioxo-imidazolidin-1-yl]-propionylamino}-thiazole-4-carboxylic acid methyl ester;

2-[(S)-2-{4-[4-(2-methoxy-ethoxy)-phenyl]-2,5-dioxo-imidazolidin-1-yl}-3-(2-methoxy-phenyl)-propionylamino]-thiazole-4-carboxylic acid methyl ester;

2-{(S)-3-(2-cyano-phenyl)-2-[(R)-4-(4-methoxy-phenyl)-2,5-dioxo-imidazolidin-1-yl]-propionylamino}-thiazole-4-carboxylic acid methyl ester;

2-((S)-3-(2-cyano-phenyl)-2-{4-[(R)-4-(2-methoxy-ethoxy)-phenyl]-2,5-dioxo-imidazolidin-1-yl}-propionylamino)-thiazole-4-carboxylic acid methyl ester;

2-{(S)-2-[4-((R)-(4-ethoxy-phenyl))-2,5-dioxo-imidazolidin-1-yl]-3-phenyl-propionylamino}-thiazole-4-carboxylic acid methyl ester;

2-((S)-2-{(R)-4-[4-((R)-2,3-dihydroxy-propoxy)-phenyl]-2,5-dioxo-imidazolidin-1-yl}-3-phenyl-propionylamino)-thiazole-4-carboxylic acid methyl ester;

2-{(S)-2-[4-(4-methoxy-3-methyl-phenyl)-2,5-dioxo-imidazolidin-1-yl]-3-phenyl-propionylamino}-thiazole-4-carboxylic acid methyl ester;

2-{(S)-2-[4-(3-isopropyl-4-methoxy-phenyl)-2,5-dioxo-imidazolidin-1-yl]-3-phenyl-propionylamino}-thiazole-4-carboxylic acid methyl ester;

2-{(S)-2-[4-(3-ethyl-4-methoxy-phenyl)-2,5-dioxo-imidazolidin-1-yl]-3-phenyl-propionylamino}-thiazole-4-carboxylic acid methyl ester;

2-{(S)-2-[(R)-4-(4-methoxy-phenyl)-2,5-dioxo-imidazolidin-1-yl]-3-phenyl-propionylamino}-thiazole-4-carboxylic acid methoxy-methyl-amide;

(S)-N-(4-acetyl-thiazol-2-yl)-2-(2,5-dioxo-4-phenyl-imidazolidin-1-yl)-3-phenyl-propionamide;

2-[(S)-2-(2,5-dioxo-4-phenyl-imidazolidin-1-yl)-3-phenyl-propionylamino]-thiazole-4-carboxylic acid amide and 2-[(S)-2-(2,5-dioxo-4-phenyl-imidazolidin-1-yl)-3-phenyl-propionylamino]-thiazole-4-carboxylic acid dimethylamide.

5. A pharmaceutical composition comprising a compound of the formula

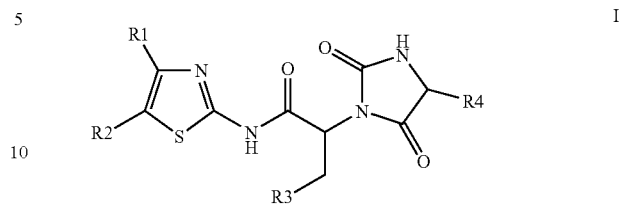

wherein
$R^1$ is $COR^5$;
$R^2$ is hydrogen;
$R^3$ is selected from the group consisting of substituted or unsubstituted alkyl, substituted or unsubstituted alkenyl, substituted or unsubstituted alkynyl, cycloalkyl, substituted or unsubstituted heterocycle, substituted or unsubstituted aryl and substituted or unsubstituted heteroaryl;
$R^4$ is selected from the group consisting of substituted or unsubstituted aryl and substituted or unsubstituted heteroaryl;
$R^5$ is selected the group consisting of lower alkyl, lower alkoxy and amine substituted
by hydrogen, lower alkyl or lower alkoxy;
and the pharmaceutically acceptable salts, esters or prodrugs thereof together with a pharmaceutically acceptable carrier or excipient.

* * * * *